(12) United States Patent (10) Patent No.: US 7,094,536 B2
Kurn (45) Date of Patent: Aug. 22, 2006

(54) METHODS AND COMPOSITIONS FOR AMPLIFICATION OF RNA SEQUENCES

(75) Inventor: Nurith Kurn, Palo Alto, CA (US)

(73) Assignee: NuGEN Technologies, Inc., San Carlos, CA (US)

( * ) Notice: Subject to any disclaimer, the term of this patent is extended or adjusted under 35 U.S.C. 154(b) by 0 days.

(21) Appl. No.: 10/096,221

(22) Filed: Mar. 11, 2002

(65) Prior Publication Data

US 2002/0164628 A1 Nov. 7, 2002

Related U.S. Application Data

(60) Provisional application No. 60/274,236, filed on Mar. 9, 2001.

(51) Int. Cl.
*C12Q 1/68* (2006.01)
*C12P 19/34* (2006.01)

(52) U.S. Cl. .......................... 435/6; 435/91.1; 435/91.2
(58) Field of Classification Search ................ 435/91.1, 435/91.2, 810; 536/23.1, 24.33
See application file for complete search history.

(56) References Cited

U.S. PATENT DOCUMENTS

| | | | |
|---|---|---|---|
| 4,582,788 A | 4/1986 | Erlich | |
| 4,683,194 A | 7/1987 | Saiki et al. | |
| 4,786,600 A | 11/1988 | Kramer et al. | |
| 4,876,187 A | 10/1989 | Duck et al. | |
| 4,908,385 A | 3/1990 | Bar-Tana et al. | |
| 5,011,769 A | 4/1991 | Duck et al. | |
| 5,043,272 A | 8/1991 | Hartley | |
| 5,130,238 A | 7/1992 | Malek et al. | |
| 5,169,766 A * | 12/1992 | Schuster et al. | 435/91.2 |
| 5,185,243 A | 2/1993 | Ullman et al. | |
| 5,194,370 A | 3/1993 | Berninger et al. | |
| 5,399,491 A | 3/1995 | Kacian et al. | |
| 5,403,711 A | 4/1995 | Walder et al. | |
| 5,409,818 A | 4/1995 | Davey et al. | |
| 5,427,911 A | 6/1995 | Ruano | |
| 5,427,929 A | 6/1995 | Richards et al. | |
| 5,437,990 A | 8/1995 | Burg et al. | |
| 5,480,784 A | 1/1996 | Kacian et al. | |
| 5,508,178 A | 4/1996 | Rose et al. | |
| 5,510,270 A | 4/1996 | Fodor et al. | |
| 5,545,522 A | 8/1996 | Van Gelder et al. | |
| 5,554,516 A | 9/1996 | Kacian et al. | |
| 5,554,517 A | 9/1996 | Davey et al. | |
| 5,556,752 A | 9/1996 | Lockhart et al. | |
| 5,578,832 A | 11/1996 | Trulson et al. | |
| 5,589,339 A | 12/1996 | Hampson et al. | |
| 5,595,891 A | 1/1997 | Rose et al. | |
| 5,648,211 A | 7/1997 | Fraiser et al. | |
| 5,654,142 A | 8/1997 | Kievits et al. | |
| 5,660,988 A | 8/1997 | Duck et al. | |
| 5,665,545 A | 9/1997 | Malek et al. | |
| 5,679,512 A | 10/1997 | Laney et al. | |
| 5,683,879 A | 11/1997 | Laney et al. | |
| 5,700,642 A | 12/1997 | Monforte et al. | |
| 5,710,028 A | 1/1998 | Eyal et al. | |
| 5,716,785 A | 2/1998 | Van Gelder et al. | |
| 5,731,146 A | 3/1998 | Duck et al. | |
| 5,744,308 A | 4/1998 | Guillou-Bonnici et al. | |
| 5,744,312 A | 4/1998 | Mamone et al. | |
| 5,763,178 A | 6/1998 | Chirikjian et al. | |
| 5,766,849 A | 6/1998 | McDonough et al. | |
| 5,773,601 A | 6/1998 | Agrawal | |
| 5,824,517 A | 10/1998 | Cleuziat et al. | |
| 5,824,518 A | 10/1998 | Kacian et al. | |
| 5,829,547 A | 11/1998 | Fujii et al. | |
| 5,830,655 A | 11/1998 | Monforte et al. | |
| 5,846,710 A | 12/1998 | Bajaj | |
| 5,849,547 A | 12/1998 | Cleuziat et al. | |
| 5,854,033 A | 12/1998 | Lizardi | |
| 5,858,665 A | 1/1999 | Hepp et al. | |
| 5,871,697 A | 2/1999 | Rothberg et al. | |
| 5,876,976 A | 3/1999 | Richards et al. | |
| 5,882,867 A | 3/1999 | Ullman et al. | |
| 5,888,779 A | 3/1999 | Kacian et al. | |
| 5,888,819 A | 3/1999 | Goelet et al. | |
| 5,916,777 A | 6/1999 | Kacian et al. | |
| 5,932,450 A | 8/1999 | Dattagupta et al. | |
| 5,932,451 A * | 8/1999 | Wang et al. | 435/91.21 |
| 5,958,681 A | 9/1999 | Wetmur et al. | |
| 5,962,271 A | 10/1999 | Chenchik et al. | |
| 5,962,272 A | 10/1999 | Chenchik et al. | |
| 5,965,409 A | 10/1999 | Pardee et al. | |

(Continued)

FOREIGN PATENT DOCUMENTS

| | | |
|---|---|---|
| EP | 0 050 424 | 4/1982 |
| EP | 0 084 796 | 8/1983 |
| EP | 0 201 184 | 12/1986 |

(Continued)

OTHER PUBLICATIONS

Wang et al. (2000. "High–fidelity mRNA amplification for gene profiling," *Nature Biotechnology* 18: 457–459.
U.S. Appl. No. 09/870,433, filed May 29, 2001, Kurn.
U.S. Appl. No. 09/990,531, filed Oct. 9, 2001, Kurn.

(Continued)

*Primary Examiner*—Gary Benzion
(74) *Attorney, Agent, or Firm*—Morrison & Foerster LLP

(57) ABSTRACT

The invention provides methods for linear and exponential amplification of RNA. They are particularly suitable for amplifying a plurality of RNA species in a sample. The methods are based on hybridization of polynucleotide comprising a propromoter sequence to a primer extension product to generate an intermediate polynucleotide capable of driving transcription, whereby multiple copies of RNA products comprising sequences complementary to an RNA sequence of interest are generated. The methods are useful for preparation of nucleic acid libraries and substrates for analysis of gene expression of cells in biological samples. The invention also provides compositions and kits for practicing the amplification methods, as well as methods which use the amplification products.

98 Claims, 5 Drawing Sheets

U.S. PATENT DOCUMENTS

| | | | |
|---|---|---|---|
| 6,004,744 | A | 12/1999 | Goelet et al. |
| 6,004,745 | A | 12/1999 | Arnold, Jr. et al. |
| 6,013,431 | A | 1/2000 | Soderlund et al. |
| 6,027,889 | A | 2/2000 | Barany et al. |
| 6,027,923 | A | 2/2000 | Wallace |
| 6,030,774 | A | 2/2000 | Laney et al. |
| 6,037,152 | A | 3/2000 | Richards et al. |
| 6,090,591 | A | 7/2000 | Burg et al. |
| 6,096,715 | A | 8/2000 | Rossi et al. |
| 6,107,032 | A | 8/2000 | Kilger et al. |
| 6,132,997 | A | 10/2000 | Shannon |
| 6,136,533 | A | 10/2000 | Bekkaoui et al. |
| 6,143,495 | A | 11/2000 | Lizardi et al. |
| 6,218,151 | B1 | 4/2001 | Cleuziat et al. |
| 6,251,600 | B1 | 6/2001 | Winger et al. |
| 6,251,639 | B1 | 6/2001 | Kurn |
| 6,271,002 | B1 | 8/2001 | Linsley et al. |
| 6,291,170 | B1 | 9/2001 | Van Gelder et al. |
| 6,358,712 | B1 | 3/2002 | Jarrell et al. |
| 6,686,156 | B1 | 2/2004 | Kurn |
| 6,692,918 | B1 | 2/2004 | Kurn |
| 2001/0000077 | A1 | 3/2001 | Engelhardt et al. |
| 2001/0034048 | A1 | 10/2001 | Kurn |
| 2001/0041334 | A1 | 11/2001 | Rashtchian et al. |
| 2002/0058270 | A1 | 5/2002 | Kurn |
| 2002/0115088 | A1 | 8/2002 | Kurn |
| 2002/0127575 | A1 | 9/2002 | Hoke et al. |
| 2002/0142309 | A1 | 10/2002 | Dattagupta |
| 2002/0177141 | A1 | 11/2002 | Chee et al. |
| 2003/0017591 | A1 | 1/2003 | Kurn |
| 2003/0073081 | A1 | 4/2003 | Mukai et al. |
| 2003/0087251 | A1 | 5/2003 | Kurn |
| 2003/0104460 | A1 | 6/2003 | Rabbani et al. |
| 2003/0186234 | A1 | 10/2003 | Kurn |
| 2003/0215926 | A1 | 11/2003 | Kurn et al. |
| 2004/0005614 | A1 | 1/2004 | Kurn et al. |
| 2004/0023271 | A1 | 2/2004 | Kurn et al. |
| 2005/0019793 | A1 | 1/2005 | Kurn et al. |
| 2005/0064456 | A1 | 3/2005 | Kurn et al. |

FOREIGN PATENT DOCUMENTS

| | | |
|---|---|---|
| EP | 0 237 362 | 9/1987 |
| EP | 0 258 017 | 3/1988 |
| EP | 0 320 308 | 6/1989 |
| EP | 0 365 627 | 5/1990 |
| EP | 0 395 398 | 10/1990 |
| EP | 0 497 271 | 8/1992 |
| EP | 0 500 224 | 8/1992 |
| EP | 0 505 012 | 9/1992 |
| EP | 0 543 612 | 5/1993 |
| EP | 0 667 393 | 8/1995 |
| EP | 0 878 553 A2 | 11/1998 |
| EP | 0 971 039 A2 | 1/2000 |
| EP | 1 055 736 | 11/2000 |
| EP | 1 167 524 | 1/2002 |
| EP | 1275737 | 1/2003 |
| EP | 1 281 757 | 2/2003 |
| EP | 1 312 682 | 5/2003 |
| JP | 07-023799 | 1/1995 |
| WO | WO 88/02746 A1 | 4/1988 |
| WO | WO 88/10315 | 12/1988 |
| WO | WO 89/01050 | 2/1989 |
| WO | WO 92/15712 A1 | 9/1992 |
| WO | WO 95/03426 | 2/1995 |
| WO | WO 97/04126 | 2/1997 |
| WO | WO 97/32040 A2 | 9/1997 |
| WO | WO 98/01050 A1 | 1/1998 |
| WO | WO 98/28443 | 7/1998 |
| WO | WO 99/18241 | 4/1999 |
| WO | WO-99/25873 A1 | 5/1999 |
| WO | WO 99/29901 | 6/1999 |
| WO | WO 99/37808 | 7/1999 |
| WO | WO 99/40219 | 8/1999 |
| WO | WO 99/42618 A1 | 8/1999 |
| WO | WO 99/55912 A1 | 11/1999 |
| WO | WO 00/08208 | 2/2000 |
| WO | WO 00/09745 A1 | 2/2000 |
| WO | WO 00/28082 | 5/2000 |
| WO | WO 00/40715 | 7/2000 |
| WO | WO 00/52191 | 9/2000 |
| WO | WO 00/56925 A2 | 9/2000 |
| WO | WO 00/70095 A2 | 11/2000 |
| WO | WO 01/20035 A2 | 3/2001 |
| WO | WO 01/23613 | 4/2001 |
| WO | WO 01/64952 | 9/2001 |
| WO | WO 01/73134 | 10/2001 |
| WO | WO 02/00938 | 1/2002 |
| WO | WO 02/29117 | 4/2002 |
| WO | WO 02/29117 A2 | 4/2002 |
| WO | WO 02/028876 | 4/2002 |
| WO | WO 02/48402 | 6/2002 |
| WO | WO 02/057487 | 7/2002 |
| WO | WO 02/072772 | 9/2002 |
| WO | WO 02/072773 | 9/2002 |
| WO | WO 02/103013 | 12/2002 |
| WO | WO 03/012100 | 2/2003 |
| WO | WO 03/012142 | 2/2003 |
| WO | WO 03/078645 | 9/2003 |
| WO | WO 03/083435 | 10/2003 |

OTHER PUBLICATIONS

U.S. Appl. No. 09/974,756, filed Oct. 9, 2001, Kurn.

U.S. Appl. No. 10/017,880, filed Dec. 13, 2001, Kurn.

U.S. Appl. No. 10/100,321, filed Mar. 11, 2002, Kurn.

Blanchard et al. (1996). "High–density oligonucleotide arrays" *Biosensors & Bioelectronics* 11(6/7):687–690.

Caruthers et al. (1987). "Chemical synthesis of deoxyoligonucleotides by the phosphoramidite method" *Methods in Enzymology* 154:287–313.

DeRisi et al. (Dec. 1996) "Use of a cDNA microarray to analyse gene expression patterns in human cancer" *Nature Genetics* 14:457–460.

Flanagan et al. (1999) "A cytosine analog that confers enhanced potency to antisense oligonucleotides" *Proc Natl. Acad. Sci. U.S.A* 96(7):3513–3518.

Fodor et al. (Feb. 15, 1991) "Light–Directed, spatially addressable parallel chemical synthesis" *Science* 251:767–773.

Guatelli et al. (1990). "Isothermal, in vitro amplification of nucleic acids by a multienzyme reaction modeled after retroviral replication" *Proc. Natl. Acad. Sci. U.S.A.* 87:1874–1878.

Gubler and Hoffman (1983). "A simple and very efficient method for generating cDNA libraries" *Gene* 25:263–269.

Khrapko et al. (1991). "A method for DNA sequencing by hybridization witholigonucleotide matrix" *DNA Sequence* 1:375–388.

Kumar et al. (1998). "The first analogues of locked nucleic acids: Phosphorothioate–1.NA and 2'–thio–INA" *Bioorg. Med. Chem. Lett* 8(16):2219–2222.

Lockhart et al. (1996). "Expression monitoring by hybridization to high–density oligonucleotide arrays" *Nature Biotechnology* 14:1675–1680.

Marshall and Hodgson. (Jan. 1998). "DNA chips: An array of possibilities" *Nature Biotechnol.* 16:27–31.

Maskos and Southern. (1992). "Oligonucleotide hybridisations on glass supports: a novel linker for oligonucleotide synthesis and hybridisation properties of oligonucleotides synthesised in situ" *Nucl. Acids. Res*. 20(7):1679–1684.

Matson et al. (1995). "Bioploymer synthesis on polypropylene supports: Oligonucleotides arrays" *Anal Biochem*. 224(1):110–116.

Mullis et al. (1987). "Specific synthesis of DNA in vitro via a polymerase–catalyzed chain reaction" *Methods in Enzymology* 155:335–350.

Okayama and Berg (1982) "High Efficiency Cloning of Full–Length cDNA" *Molecular and Cell Biology* 2:161–170.

Patel et al. (1996). "Formation of chimeric DNA primer extension products by template switching onto an annealed downstream oligonucleotide" *Proc. Natl. Acad. Sci. U.S.A*. 93:2969–2974.

Pease et al. (May 1994). "Light–generated oligonucleotide arrays for rapid DNA sequence analysis" *Proc. Natl. Acad. Sci U.S.A. Biochemistry*, 91:5022–5026.

Ramsay, (Jan. 1998). "DNA chips: State–of–the–art" *Nature Biotechnol*. 16:40–44.

Saiki et al. (1988). "Primer–directed enzymatic amplification of DNA with a termostable DNA polymerase" *Science* 239:487–491.

Sasaki et al. (Mar. 1998). "Transcriptional sequencing: A method for DNA sequencing using RNA polymerase" *Biochemistry* 95:3455–3460.

Scaringe et al. (1998). "Novel RNA synthesis method using 5'–0–silyl–2'–0–orthoester protecting groups" *J. Am. Chem. Soc*. 120:11820–11821.

Scaringe. "Advanced 5'–silyl2'–orthoester approach to RNA oligonucleotide synthesis" *Methods in Enzymology* 317:3–18.

Schena et al. (Oct. 20. 1995) "Quantitative monitoring of gene expression patterns with a complementary DNA microarray" *Science* 270:467–470.

Schena et al. (Oct. 1996). "Parallel human genome analysis: Microarray–based expression monitoring of 1000 genes" *Proc. Natl. Acad. Sci. U.S.A. Biochemistry* 93:10614–10619.

Shalon et al. (1996) "A DNA microarray system for analyzing complex DNA samples using two–color fluorescent probe hybridization" *Genome Res*. 6:639–645.

Wahlestedt et al. (2000). "Potent and nontoxic antisense oligonucleotides containing locked nucleic acids" *Proc. Natl. Acad. Sci*. 97(10):5633–5638.

Walker et al. (1992). "Isothermal in vitro amplification of DNA by a restriction enzyme DNA polymerase system" *Proc. Natl. Acad. Sci U.S.A*. 89:392–396.

U.S. Appl. No. 10/824,829, filed Apr. 14, 2004, Kurn et al.

U.S. Appl. No. 10/857,160, filed May 28, 2004, Kurn.

Fu, D.–J. et al., (1997) "Sequencing double–stranded DNA by strand displacment" *Nucleic Acids Research* 25(3):677–679.

Gasparini et al. (1996). "Scanning the First Part of the Neurofibromatosis Type 1 Gene by RNA–SSCP: Identification of Three Novel Mutations and of Two New Polymorphisms," *Hum. Genet*. 97:492–495.

Kwoh et al. (1989). "Transcription–Based Amplification System and Detection Amplified Human Immunodeficiency Virus Type 1 with a Bead–Based Sandwich Hybridization Format," *Proc. Natl. Acad. Sci. USA* 86:1173–1177.

Lishanski, A. et al. (2000). "Branch Migration Inhibition in PCR–Amplified DNA: Homogeneous Mutation Detection," *Nucl. Acids Res*. 28(9):E42, pp. i–vii.

Orita, M. et al. (1989). "Detection of Polymorphisms of Human DNA by Gel Electrophoresis as Single–Strand Conformation Polymorphisms," *Proc. Natl. Acad. Sci. USA* 86(8):2766–2770.

Orita, M. et al. (1989). "Rapid and sensitive detection of point mutations and DNA polymorphisms using the polymerase chain reaction," *Genomics* 5(4):874–879.

Sarkar et al. (1992). "Screening for Mutations by RNA Single–Strand Conformation Polymorphism (rSSCP): Comparison with DNA–SSCP," *Nucl. Acids Res*. 20(4):871–878.

Suzuki, Y. et al. (1990). "Detection of ras Gene Mutations in Human Lung Cancers by Single–Strand Conformation Polymorphism Analysis of Polymerase Chain Reaction Products," *Oncogene* 5(7):1037–1043.

Wu et al. (1989). "The Ligation Amplification Reaction (LAR)—Amplification of Specific DNA Sequences Using Sequential Rounds of Template–Dependent Ligation," *Genomics* 4:560–569.

European Search Report (Supplementary partial) mailed Dec. 22, 2005 for European Patent Application No. 02731119.0, six pages.

* cited by examiner

Exponential isothermal amplification

Exponential isothermal amplification

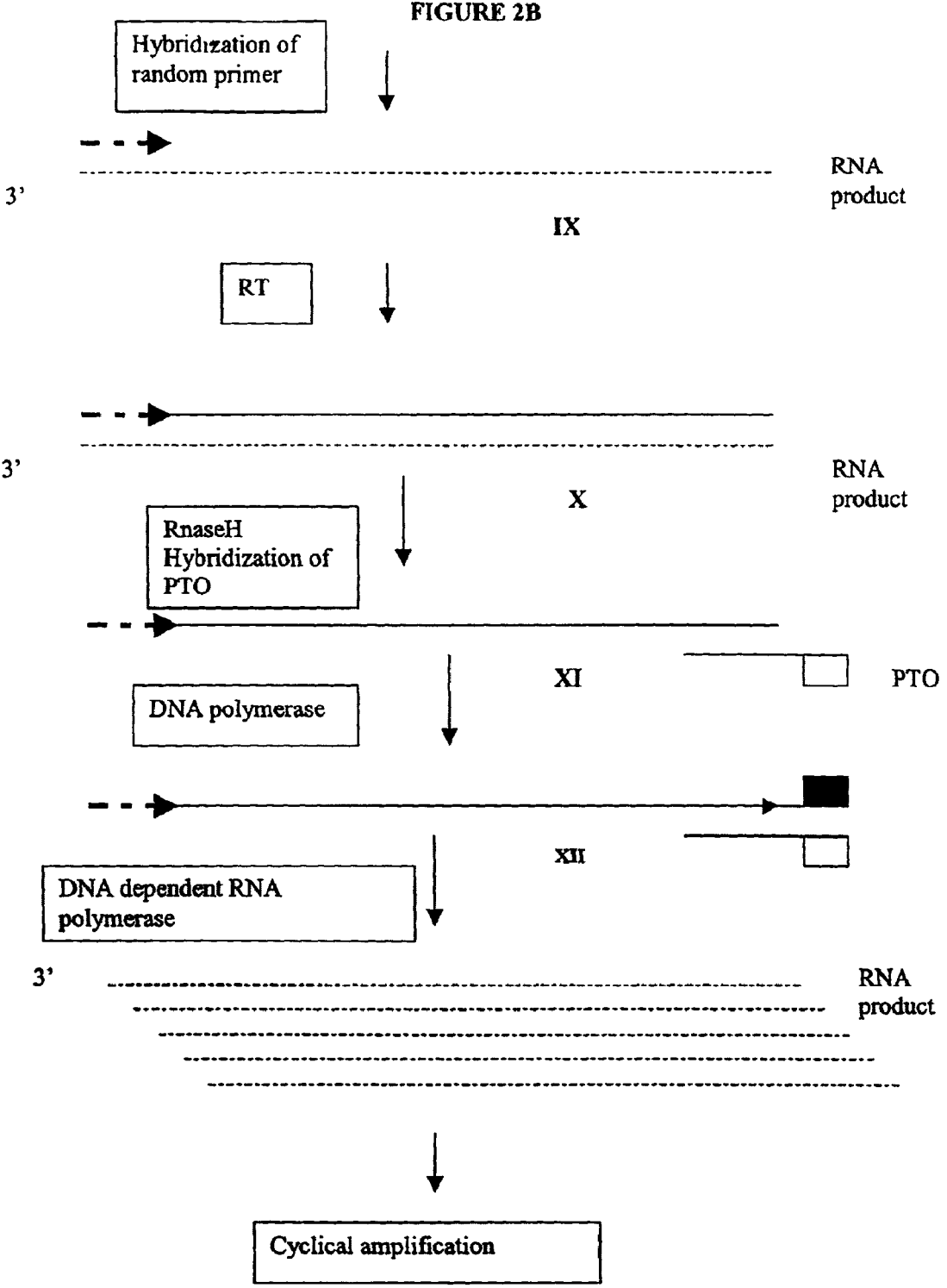

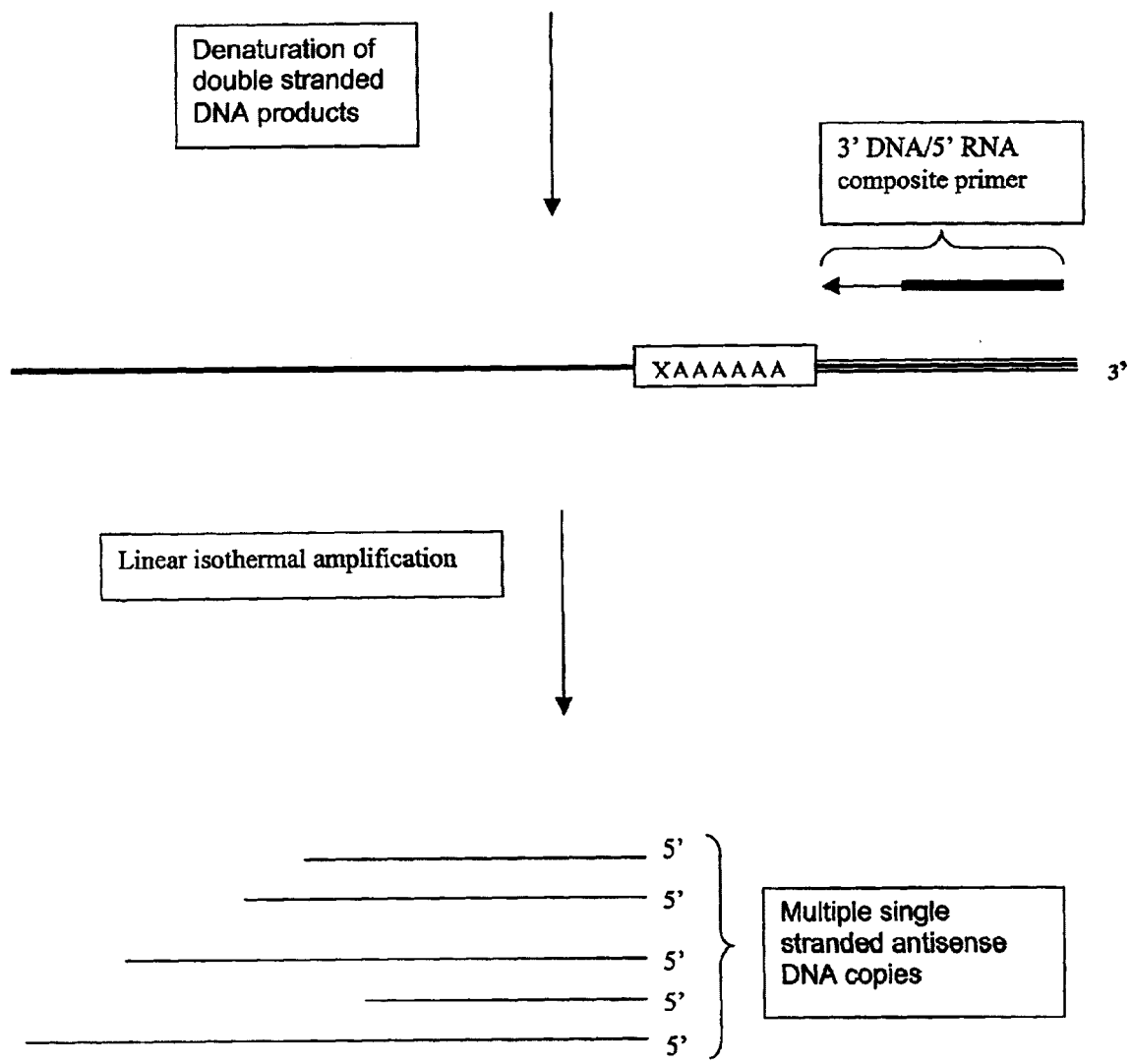

US 7,094,536 B2

METHODS AND COMPOSITIONS FOR AMPLIFICATION OF RNA SEQUENCES

CROSS-REFERENCE TO RELATED APPLICATIONS

This application claims the priority benefit of the provisional patent application U.S. Ser. No. 60/274,236, filed Mar. 9, 2001, which is incorporated by reference in its entirety.

TECHNICAL FIELD

The invention relates to the field of polynucleotide amplification. More particularly, the invention provides methods, compositions and kits for amplifying (i.e., making multiple copies) RNA sequences of interest which employ a polynucleotide comprising a propromoter and RNA transcription.

BACKGROUND ART

The ability to amplify ribonucleic acid (RNA) is an important aspect of efforts to elucidate biological processes. To date, RNA (generally, mRNA) amplification is most commonly performed using the reverse transcriptase-polymerase chain reaction (RT-PCR) method and variations thereof. These methods are based on replication of RNA by reverse transcriptase to form single stranded DNA complementary to the RNA (cDNA), which is followed by polymerase chain reaction (PCR) amplification to produce multiple copies of double stranded DNA. Although these methods are most commonly used, they have some significant drawbacks: a) the reactions require thermocycling; b) the products are double stranded, thus rendering them less accessible to binding to probes; c) the reactions are prone to contamination with products of prior amplification, thus requiring strict containment of reaction mixtures; and d) the exponential nature of amplification of these methods renders them prone to generate pools of products which do not truly reflect the representation of the various RNA sequences in the input total RNA sample, due to unequal efficiency of amplification of different sequences, and the nature of exponential amplification which is based on replication of amplification products rather than on continued replication of the input target RNAs.

The total cellular mRNA represents gene expression activity at a defined time. Gene expression is affected by cell cycle progression, developmental regulation, response to internal and external stimuli and the like. The profile of expressed genes for any cell type in an organism reflects normal or disease states, response to various stimuli, developmental stages, cell differentiation, and the like.

Various methods for the analysis of gene expression have be developed in recent years. See, for example, U.S. Pat. Nos. 5,744,308; 6,143,495; 5,824,517; 5,829,547; 5,888,779; 5,545,522; 5,716,785; 5,409,818; EP 0971039A2; EP 0878553A2. These include quantification of specific mRNAs, and the simultaneous quantification of a large number of mRNAs, as well as the detection and quantification of patterns of expression of known and unknown genes. The analysis of gene expression profiles is currently one of the most powerful tools in the study of cellular differentiation and cellular development, and in the investigation of normal and disease states of various organisms, in particular in human. This analysis is crucial for gene discovery, molecular medicine and drug discovery processes.

Essential for gene expression profiling is the ability to randomly amplify the total cellular mRNAs prepared from any cell or tissue. Although analysis of non-amplified mRNA is feasible, a significant amount of starting mRNA would be required. However, the total amount of sample mRNA that is available is frequently limited by the amount of biological sample from which it is derived. Biological samples are often limited in amount and precious. Moreover, the amount of the various mRNA species is not equal; some species are more abundant than others, and these are more likely and easier, to analyze. The ability to amplify mRNA sequences enables the analysis of less abundant, rare mRNA species. The ability to analyze small samples, by means of nucleic acid amplification, is also advantageous for design parameters of large scale screening of effector molecule libraries, for which reduction in sample volume is a major concern both for the ability to perform very large scale screening or ultra high throughput screening, and in view of the limiting amounts of library components.

Therefore, there is a need for improved RNA amplification methods that overcome drawbacks in existing methods. The invention provided herein fulfills this need and provides additional benefits.

All references cited herein, including patent applications and publications, are incorporated by reference in their entirety.

DISCLOSURE OF THE INVENTION

The invention provides methods, compositions, and kits for polynucleotide, specifically ribonucleic acid, amplification, as well as applications of the amplification methods.

In one aspect, the invention provides methods of generating multiple copies of the complementary sequence of an RNA sequence of interest, said method comprising the steps of: (a) extending a first primer hybridized to a target RNA with an RNA-dependent DNA polymerase, whereby a complex comprising a first primer extension product and the target RNA is produced; (b) cleaving RNA in the complex of step (b) with an enzyme that cleaves RNA from an RNA/DNA hybrid; (c) extending a second primer hybridized to the first primer extension product with a DNA-dependent DNA polymerase, whereby a complex comprising the first primer extension product and a second primer extension product is produced; (d) denaturing the complex of step (c); and (e) hybridizing to the second primer extension product a propromoter polynucleotide comprising a propromoter and a region which hybridizes to the second primer extension product under conditions which allow transcription to occur by RNA polymerase, such that RNA transcripts are produced comprising sequences complementary to the target RNA; whereby multiple copies of the complementary sequence of the RNA sequence of interest are generated.

In one aspect, the invention provides methods of generating multiple copies of (amplifying) the complementary sequence of an RNA sequence of interest, said method comprising the steps of: (a) hybridizing a first primer to a target ribonucleic acid; (b) extending the first primer with an RNA-dependent DNA polymerase, whereby a complex comprising a first primer extension product and the target ribonucleic acid is produced; (c) cleaving ribonucleic acid in the complex of step (b) with an enzyme that cleaves RNA from an RNA/DNA hybrid; (d) hybridizing a second primer to the first primer extension product; (e) extending the second primer with a DNA-dependent DNA polymerase, whereby a complex comprising the first primer extension product and a second primer extension product is produced; (f) denaturing the complex of step (e); (g) hybridizing to the second primer extension product a polynucleotide comprising a propromoter and a region which hybridizes to the second primer extension product under conditions which allow transcription to occur by RNA polymerase, such that RNA transcripts are produced comprising sequences complementary to the target ribonucleic acid, whereby multiple copies of the complementary sequence of the RNA sequence of interest are generated. In some embodiments, the polynucleotide comprising a propromoter is a propromoter template oligonucleotide (PTO). In some embodiments, the invention provides methods of generating multiple copies of the complementary sequence of an RNA sequence of interest, said methods comprising the steps of: (a) combining: a single stranded second primer extension product resulting from step (f) of the aspect of the invention described above; a propromoter polynucleotide comprising a propromoter and a region which is hybridizable to a single stranded second primer extension product; and an RNA polymerase; and (b) incubating the mixture of step (a) under conditions (which includes necessary substrates and buffer conditions) that permit propromoter polynucleotide hybridization and RNA transcription, whereby multiple copies of the complementary sequence of the RNA sequence of interest are generated. It is understood that any combination of these incubation steps, and any single incubation step, to the extent that the incubation is performed as part of any of the methods described herein, fall within the scope of the invention. It is also understood that methods that comprise one or more incubation steps do not require a separate combination step, as such combinations are implicit in incubating the reaction mixture(s).

In another aspect, the invention provides methods of generating multiple copies of the complementary sequence of an RNA sequence of interest, said method comprising the steps of: (a) extending a first primer hybridized to a target RNA with an RNA-dependent DNA polymerase, whereby a complex comprising a first primer extension product and the target RNA is produced; (b) cleaving RNA in the complex of step (a) with an enzyme that cleaves RNA from an RNA/DNA hybrid; (c) extending a second primer hybridized to the first primer extension product with a DNA-dependent DNA polymerase, whereby a complex comprising the first primer extension product and a second primer extension product is produced; (d) denaturing the complex of step (c); (e) hybridizing to the second primer extension product a propromoter polynucleotide comprising a propromoter and a region which hybridizes to the second primer extension product under conditions which allow transcription to occur by RNA polymerase, such that RNA transcripts are produced comprising sequences complementary to the target RNA; (f) extending a third primer hybridized to said RNA transcripts with an RNA-dependent DNA polymerase, whereby a complex comprising a third primer extension product and an RNA transcript is produced; (g) cleaving RNA in the complex of step (f) with an enzyme that cleaves RNA from an RNA/DNA hybrid; (h) hybridizing a propromoter polynucleotide comprising a propromoter and a region which hybridizes to a single stranded third primer extension product under conditions which allow transcription to occur by RNA polymerase, such that RNA transcripts are produced comprising sequences complementary to the target RNA; (i) optionally repeating steps (f) to (h); whereby multiple copies of the complementary sequence of the RNA sequence of interest are produced.

In another aspect, the invention provides methods of generating multiple copies of (amplifying) the complementary sequence of an RNA sequence of interest, said method comprising the steps of: (a) hybridizing a first primer to a target ribonucleic acid; (b) extending the first primer with an RNA-dependent DNA polymerase, whereby a complex comprising a first primer extension product and the target ribonucleic acid is produced; (c) cleaving ribonucleic acid in the complex of step (b) with an enzyme that cleaves RNA from an RNA/DNA hybrid; (d) hybridizing a second primer to the first primer extension product; (e) extending the second primer with a DNA-dependent DNA polymerase, whereby a complex comprising the first primer extension product and a second primer extension product is produced; (f) denaturing the complex of step (e); (g) hybridizing to the second primer extension product a propromoter and a region which hybridizes to the second primer extension product under conditions which allow transcription to occur by RNA polymerase, such that RNA transcripts are produced comprising sequences complementary to the target ribonucleic acid; (h) hybridizing a third primer to said RNA transcripts; (i) extending the third primer with an RNA-dependent DNA polymerase, whereby a complex comprising a third primer extension product and an RNA transcript is produced; (j) cleaving RNA in the complex of step (i) with an enzyme that cleaves RNA from an RNA/DNA hybrid; (k) hybridizing a propromoter polynucleotide comprising a propromoter and a region which hybridizes to a single stranded third primer extension product under conditions which allow transcription to occur by RNA polymerase, such that RNA transcripts are produced comprising sequences complementary to the target ribonucleic acid; (l) optionally repeating steps (h) to (k), whereby multiple copies of the complementary sequence of the RNA sequence of interest are produced. In some embodiments, the polynucleotide comprising a propromoter is a propromoter template oligonucleotide (PTO). In some embodiments, the invention provides methods of generating multiple copies of the complementary sequence of an RNA sequence of interest, said methods comprising the steps of: (a) combining: a single stranded second primer extension product resulting from step (f) described above in this paragraph; a third primer comprising a sequence hybridizable to an RNA transcript comprising a sequence complementary to the target RNA; a propromoter polynucleotide comprising a propromoter and a region which is hybridizable to a single stranded second primer extension product; a propromoter polynucleotide comprising a propromoter and a region which is hybridizable to a single stranded third primer extension product; an enzyme that cleaves RNA from an RNA/DNA hybrid; and an RNA polymerase; and (b) incubating the mixture of step (a) under conditions (which includes necessary substrates and buffers) that permit primer extension, RNA cleavage, propromoter polynucleotide hybridization and RNA transcription, whereby multiple copies of the complementary sequence of the RNA sequence of interest are generated. In yet another embodiment, the invention provides methods of generating multiple copies of the complementary sequence of an RNA sequence of interest, said methods comprising the steps of: (a) combining: an RNA transcript from step (g) described above in this paragraph; a third primer comprising a sequence hybridizable to the RNA transcript; a propromoter polynucleotide comprising a propromoter and a region which is hybridizable to a single stranded third primer extension product; an enzyme that cleaves RNA from an RNA/DNA hybrid; and an RNA polymerase; and (b) incubating the mixture of step (a) under conditions (which includes necessary substrates and buffers) that permit primer extension, RNA cleavage, propromoter polynucleotide hybridization and RNA transcription, whereby multiple copies of the complementary sequence of the RNA sequence of interest are generated.

In still another aspect, the invention provides methods of generating multiple copies of (amplifying) the complementary sequence of an RNA sequence of interest, said method comprising the steps of: (a) combining: a target ribonucleic acid; a first primer comprising a sequence that is hybridizable to the target ribonucleic acid; a second primer comprising a sequence hybridizable to an extension product of the first primer; a propromoter polynucleotide comprising a propromoter and a region which is hybridizable to a single stranded second primer extension product; an RNA-dependent DNA polymerase; a DNA-dependent DNA polymerase; an RNA polymerase; and an enzyme that cleaves RNA from an RNA/DNA hybrid; and (b) incubating the mixture of step (a) under conditions (which includes necessary substrates and buffer conditions) that permit primer hybridization, primer extension, RNA cleavage, propromoter polynucleotide hybridization, and RNA transcription. In some embodiments, the polynucleotide comprising a propromoter is a propromoter template oligonucleotide (PTO).

In yet another aspect, the invention provides methods of generating multiple copies of (amplifying) the complementary sequence of an RNA sequence of interest, said method comprising the steps of: (a) combining: a target ribonucleic acid; a first primer comprising a sequence that is hybridizable to the target ribonucleic acid; a second primer comprising a sequence hybridizable to an extension product of the first primer; a third primer comprising a sequence hybridizable to an RNA transcript comprising a sequence complementary to the target ribonucleic acid; a propromoter polynucleotide comprising a propromoter and a region which is hybridizable to a single stranded second primer extension product; a propromoter polynucleotide comprising a propromoter and a region which is hybridizable to a single stranded third primer extension product; an RNA-dependent DNA polymerase; a DNA-dependent DNA polymerase; an RNA polymerase; and an enzyme that cleaves RNA from an RNA/DNA hybrid; and (b) incubating the mixture of step (a) under conditions (which includes necessary substrates and buffer conditions) that permit primer hybridization, primer extension, RNA cleavage, propromoter polynucleotide hybridization, and RNA transcription. In some embodiments, the polynucleotide comprising a propromoter is a propromoter template oligonucleotide (PTO).

In another aspect, the invention provides methods of generating multiple copies of the complementary sequence of an RNA sequence of interest, said method comprising the steps of: (a) extending a first primer hybridized to a target RNA with an RNA-dependent DNA polymerase, whereby a complex comprising a first primer extension product and the target RNA is produced; (b) cleaving RNA in the complex of step (b) with an enzyme that cleaves RNA from an RNA/DNA hybrid; (c) extending a second primer hybridized to the first primer extension product with a DNA-dependent DNA polymerase, whereby a complex comprising the first primer extension product and a second primer extension product is produced; (d) denaturing the complex of step (c); and (e) hybridizing to the second primer extension product a propromoter polynucleotide comprising a propromoter and a region which hybridizes to the second primer extension product under conditions which allow transcription to occur by RNA polymerase, such that RNA transcripts are produced comprising sequences complementary to the target RNA; whereby multiple copies of the complementary sequence of the RNA sequence of interest are generated.

In another aspect, the invention provides methods of generating multiple copies of the complementary sequence of an RNA sequence of interest, said method comprising the steps of: (a) extending a first primer hybridized to a target RNA with an RNA-dependent DNA polymerase, whereby a complex comprising a first primer extension product and the target RNA is produced; (b) cleaving RNA in the complex of step (a) with an enzyme that cleaves RNA from an RNA/DNA hybrid; (c) extending a second primer hybridized to the first primer extension product with a DNA-dependent DNA polymerase, whereby a complex comprising the first primer extension product and a second primer extension product is produced; (d) denaturing the complex of step (c); (e) hybridizing to the second primer extension product a propromoter polynucleotide comprising a propromoter and a region which hybridizes to the second primer extension product under conditions which allow transcription to occur by RNA polymerase, such that RNA transcripts are produced comprising sequences complementary to the target RNA; (f) extending a third primer hybridized to said RNA transcripts with an RNA-dependent DNA polymerase, whereby a complex comprising a third primer extension product and an RNA transcript is produced; (g) cleaving RNA in the complex of step (f) with an enzyme that cleaves RNA from an RNA/DNA hybrid; (h) hybridizing a propromoter polynucleotide comprising a propromoter and a region which hybridizes to a single stranded third primer extension product under conditions which allow transcription to occur by RNA polymerase, such that RNA transcripts are produced comprising sequences complementary to the target RNA; (i) optionally repeating steps (f) to (h); whereby multiple copies of the complementary sequence of the RNA sequence of interest are produced.

In another aspect, the invention provides a method of generating multiple copies of the complementary sequence of an RNA sequence of interest comprising incubating a reaction mixture, said reaction mixture comprising: (a) a single stranded second primer extension product resulting from step (d) above; (b) a propromoter polynucleotide comprising a propromoter and a region which is hybridizable to a single stranded second primer extension product; and an RNA polymerase; wherein the incubation is under conditions that permit propromoter polynucleotide hybridization and RNA transcription, whereby multiple copies of the complementary sequence of the RNA sequence of interest are generated.

In another aspect, the invention provides methods of generating multiple copies of the complementary sequence of an RNA sequence of interest comprising incubating a reaction mixture, said reaction mixture comprising: (a) a single stranded second primer extension product resulting from step (d) above; (b) a third primer comprising a sequence hybridizable to an RNA transcript comprising a sequence complementary to the target RNA; (c) a propromoter polynucleotide comprising a propromoter and a region which is hybridizable to a single stranded second primer extension product; (d) a propromoter polynucleotide comprising a propromoter and a region which is hybridizable to a single stranded third primer extension product; (e) an enzyme that cleaves RNA from an RNA/DNA hybrid; and (f) an RNA polymerase; wherein the incubation is under conditions that permit primer extension, RNA cleavage, propromoter polynucleotide hybridization and RNA transcription, whereby multiple copies of the complementary sequence of the RNA sequence of interest are generated.

In another aspect, the invention provides methods of generating multiple copies of the complementary sequence of an RNA sequence of interest, said method comprising incubating a reaction mixture, said reaction mixture comprising: (a) an RNA transcript from step (e) above, (b) a third primer comprising a sequence hybridizable to the RNA transcript; (c) a propromoter polynucleotide comprising a propromoter and a region which is hybridizable to a single stranded third primer extension product; (d) an enzyme that cleaves RNA from an RNA/DNA hybrid; and (e) an RNA polymerase; wherein the incubation is under conditions that permit primer extension, RNA cleavage, propromoter polynucleotide hybridization and RNA transcription, whereby multiple copies of the complementary sequence of the RNA sequence of interest are generated.

In another aspect, the invention provides methods of generating multiple copies of the complementary sequence of an RNA sequence of interest, said method comprising incubating a reaction mixture, said reaction mixture comprising: (a) a target RNA; (b) a first primer comprising a sequence that is hybridizable to the target RNA; (c) a second primer comprising a sequence hybridizable to an extension product of the first primer; (d) a propromoter polynucleotide comprising a propromoter and a region which is hybridizable to a single stranded second primer extension product; (e) an RNA-dependent DNA polymerase; (f) a DNA-dependent DNA polymerase; (g) an RNA polymerase; and (h) an enzyme that cleaves RNA from an RNA/DNA hybrid; wherein the incubation is under conditions that permit primer hybridization, primer extension, RNA cleavage, propromoter polynucleotide hybridization, and RNA transcription, whereby multiple copies of the complementary sequence of the RNA sequence of interest are generated.

In another aspect, invention provides methods of generating multiple copies of the complementary sequence of an RNA sequence of interest, said method comprising incubating a reaction mixture, said reaction mixture comprising: (a) a target RNA; (b) a first primer comprising a sequence that is hybridizable to the target RNA; (c) a second primer comprising a sequence hybridizable to an extension product of the first primer; (d) a third primer comprising a sequence hybridizable to an RNA transcript comprising a sequence complementary to the target RNA; (e) a propromoter polynucleotide comprising a propromoter and a region which is hybridizable to a single stranded second primer extension product; (f) a propromoter polynucleotide comprising a propromoter and a region which is hybridizable to a single stranded third primer extension product; (g) an RNA-dependent DNA polymerase;(h) a DNA-dependent DNA polymerase; (i) an RNA polymerase; and (j) an enzyme that cleaves RNA from an RNA/DNA hybrid; wherein the incubation is conditions that permit primer hybridization, primer extension, RNA cleavage, propromoter polynucleotide hybridization, and RNA transcription, whereby multiple copies of the complementary sequence of the RNA sequence of interest are generated.

In another aspect, the invention provides methods of generating multiple copies of the complementary sequence of an RNA sequence of interest, said method comprising: (a) hybridizing a composite primer to a single stranded second primer extension product resulting from step (d) above, wherein the composite primer comprises an RNA portion and a 3' DNA portion; (b) extending the composite primer with a DNA-dependent DNA polymerase, whereby a complex comprising a primer extension product and the second primer extension product is formed; (c) cleaving RNA in the complex of step (b) with an enzyme that cleaves RNA from an RNA/DNA hybrid, such that another composite primer hybridizes to the second primer extension product and repeats primer extension by strand displacement, whereby multiple copies of the complement of the RNA sequence of interest are produced.

In another aspect, the invention provides methods of generating multiple copies of a polynucleotide sequence complementary to an RNA sequence of interest, said method comprising the steps of: (a) extending a composite primer hybridized to a second primer extension product, wherein said primer extension product comprises a complement of a first primer extension product generated by extension of a first primer hybridized to template RNA by any of the methods described herein; whereby said first primer extension product is displaced, and whereby multiple copies of a polynucleotide sequence complementary to the RNA sequence of interest are generated.

In another aspect, the invention provides methods of generating multiple copies of the complementary sequence of an RNA sequence of interest, said method comprising incubating a reaction mixture, said reaction mixture comprising: (a) a single stranded second primer extension product resulting from step (d) above; (b) a composite primer which is hybridizable to the single stranded second primer extension product, wherein the composite primer comprises an RNA portion and a 3' DNA portion; (c) DNA-dependent DNA polymerase; (d) an enzyme that cleaves RNA from an RNA/DNA hybrid; wherein the incubation is made under conditions that permit composite primer hybridization, RNA cleavage, and displacement of the primer extension product from the complex of step (a) described above when its RNA is cleaved and a composite primer binds to the primer extension product in the complex, whereby multiple copies of the complement of the RNA sequence of interest are produced.

In another aspect, the invention provides methods of generating multiple copies of an RNA sequence of interest, said method comprising the steps of: (a) extending a composite primer hybridized to a second primer extension product, wherein said primer extension product comprises a complement of a first primer extension product generated by extension of a first primer hybridized to template RNA by any of the methods described herein; whereby said first primer extension product is displaced, (b) hybridizing the displaced first primer extension product with a polynucleotide comprising a propromoter and a region which is hybridizable to the displaced first primer extension product under conditions which allow transcription to occur by RNA polymerase, such that RNA transcripts are produced comprising sequences complementary to the displaced primer extension products, whereby multiple copies of the RNA sequence of interest are generated.

As is clear to one skilled in the art, reference to production of copies of an RNA or DNA sequence of interest or copies of a polynucleotide sequence complementary to an RNA or DNA sequence of interest refers to products that may contain, comprise or consist of such sequences. As is evident to one skilled in the art, aspects that refer to combining and incubating the resultant mixture also encompasses method embodiments which comprise incubating the various mixtures (in various combinations and/or subcombinations) so that the desired products are formed. It is understood that any combination of these incubation steps, and any single incubation step, to the extent that the incubation is performed as part of any of the methods described herein, fall within the scope of the invention. It is also understood that methods that comprise one or more incubation steps do not require a separate combination step, as such combinations are implicit in incubating the reaction mixture(s)

Various embodiments of the primers are used in the methods of the invention. For example, in some embodiments, the first primer comprises a 5' portion that is not hybridizable (under a given set of conditions) to a target ribonucleic acid. In some of these embodiments, the 5' portion comprises a sequence the complement of which is hybridizable by a propromoter polynucleotide under a given set of conditions. In one example, the presence of said 5' portion in the first primer results in generation of a second primer extension product that is hybridizable (under a given set of conditions) by a propromoter polynucleotide. In another example, the presence of said 5' portion in the first primer results in generation of a third primer extension product that is hybridizable (under a given set of conditions) by a propromoter polynucleotide. In some embodiments wherein a target RNA is mRNA, the first primer may comprise a poly-T sequence. In other embodiments, the second primer and the third primer are the same. In still another embodiment, the second primer and the third primer are different. In yet another embodiment, the second primer and the third primer hybridize to different complementary sequences. In some embodiments, the second and/or third primer comprises a sequence (for example, a 3' sequence) that is a random sequence. In yet other embodiments, the second and/or third primer is a random primer. In yet other embodiments, the third primer is a composite primer. In some embodiments, the RNA portion of a composite primer is 5' with respect to the 3' DNA portion. In still other embodiments, the 5' RNA portion is adjacent to the 3' DNA portion. In other embodiments, the composite primer comprises the sequence of a first primer.

The enzymes which may be used in the methods and compositions are described herein. For example, the enzyme that cleaves RNA may be an RNase H, and the RNA-dependent DNA polymerase may be reverse transcriptase. The RNA-dependent DNA polymerase may comprise an RNase H enzyme activity. Similarly, a DNA polymerase may comprise both RNA-dependent and DNA-dependent DNA polymerase enzyme activities. A DNA-dependent DNA polymerase and an enzyme that cleaves RNA may also be the same enzyme. A DNA-dependent DNA polymerase, an RNA-dependent DNA polymerase, and the enzyme that cleaves RNA can also be the same enzyme.

In some embodiments, methods of the invention are used to generate labeled polynucleotide products (generally DNA or RNA products). In some embodiments of methods for generating labeled DNA products, at least one type of dNTP used is a labeled dNTP. In some embodiments of methods for generating labeled RNA products, at least one type of rNTP used is a labeled rNTP. In other embodiments of methods for generating labeled DNA products, a labeled composite primer is used.

In some embodiments, the methods of the invention employ a propromoter polynucleotide (for example, a PTO) that comprises a region at the 3' end which hybridizes to the second or third primer extension products, whereby DNA polymerase extension of the extension products produces a double stranded promoter from which transcription occurs.

The methods are applicable to amplifying any RNA target, including, for example, mRNA and ribosomal RNA. One or more steps may be combined and/or performed sequentially (often in any order, as long as the requisite product(s) are able to be formed). It is also evident, and is described herein, that the invention encompasses methods in which the initial, or first, step is any of the steps described herein. For example, the methods of the invention do not require that the first step be production of the first primer extension product from the RNA template. Methods of the invention encompass embodiments in which later, "downstream" steps are an initial step.

The invention also provides methods which employ (usually, analyze) the products of the amplification methods of the invention, such as sequencing, detection of sequence alteration(s) (e.g., genotyping or nucleic acid mutation detection); determining presence or absence of a sequence of interest; gene expression profiling; subtractive hybridization; preparation of a subtractive hybridization probe; differential amplification; preparation of libraries (including cDNA and differential expression libraries); preparation of an immobilized nucleic acid (which can be a nucleic acid immobilized on a microarray), and characterizing (including detecting and/or quantifying) amplified nucleic acid products generated by the methods of the invention.

In one aspect, the invention provides methods of sequencing an RNA sequence of interest, said method comprising (a) amplifying a target ribonucleic acid containing the sequence of interest by the methods described herein in the presence of a mixture of rNTPs and rNTP analogs such that transcription is terminated upon incorporation of an rNTP analog; and (b) analyzing the amplification products to determine sequence.

In another aspect, the invention provides methods of sequencing an RNA sequence of interest, said method comprising (a) amplifying a target ribonucleic acid containing the sequence of interest by the methods described herein, wherein RNA transcripts generated from the second primer extension product are amplified in the presence of a mixture of rNTPs and rNTP analogs such that transcription is terminated upon incorporation of an rNTP analog; and (b) analyzing the amplification products to determine sequence.

In some aspects, the invention provides methods of sequencing an RNA sequence of interest, said methods comprising amplifying a target RNA containing the sequence of interest by the amplification methods of the invention in the presence of a mixture of dNTPs and dNTP analogs (which may be labeled or unlabeled), such that primer extension is terminated upon incorporation of a dNTP analog which may be labeled or unlabeled, and analyzing the amplification products to determine sequence.

In some aspects, the invention provides methods of detecting a mutation (or, in some aspects, characterizing a sequence) in a target ribonucleic acid, comprising (a) amplifying the target ribonucleic acid by a method described herein; and (b) analyzing the amplification products of the method for single stranded conformation, wherein a difference in conformation as compared to a reference single stranded polynucleotide indicates a mutation in the target ribonucleic acid. In other embodiments, the invention provides methods of detecting a mutation (or, in some aspects, characterizing a sequence) in a target ribonucleic acid comprising analyzing amplification products of any of the methods described herein for single stranded conformation, wherein a difference in conformation as compared to a reference single stranded polynucleotide indicates a mutation in the target ribonucleic acid (or, in some aspects, characterizes the target sequence).

In another aspect, the invention provides methods of producing a nucleic acid immobilized to a substrate (which includes methods of producing a microarray), comprising (a) amplifying a target RNA by any of the methods described herein; and (b) immobilizing the amplification products on a substrate. The amplification products can be labeled or unlabeled. In other aspects, the invention provides methods of producing a microarray, comprising (a) amplifying a target RNA by an amplification method described herein; and (b) immobilizing the amplification products on a substrate (which can be solid or semi-solid). In some embodiments, microarrays are produced by immobilizing amplification products onto a substrate to make a microarray of amplification products. In other embodiments, microarrays are produced by immobilizing amplification products by any of the methods described herein onto a solid substrate to make a microarray of amplification products. The microarray can comprise at least one amplification product immobilized on a solid or semi-solid substrate fabricated from a material selected from the group consisting of paper, glass, ceramic, plastic, polypropylene, nylon, polyacrylamide, nitrocellulose, silicon an other metals, and optical fiber. An amplification product can be immobilized on the solid or semi-solid substrate in a two-dimensional configuration or a three-dimensional configuration comprising pins, rods, fibers, tapes, threads, beads, particles, microtiter wells, capillaries, and cylinders.

Any of the methods of the invention can be used to generate polynucleotide (generally, RNA or DNA) products that are suitable for characterization of an RNA sequence of interest in a sample. In one embodiment, the invention provides methods for characterizing (for example, detecting and/or quantifying and/or determining presence or absence of) an RNA sequence of interest comprising: (a) amplifying a target RNA by any of the methods described herein; and (b) analyzing the amplification products. Step (b) of analyzing the amplification products can be performed by any method known in the art or described herein, for example by detecting and/or quantifying and/or determining present or absence of amplification products that are hybridized to a probe. These amplification products may or may not be labeled. Any of the methods of the invention can be used to generate polynucleotide (generally, RNA or DNA) products that are labeled by incorporating labeled nucleotides into appropriate step(s) of the methods. These labeled products are particularly suitable for quantification and/or identification and/or determining presence or absence of by methods known in the art, which include the use of arrays such as cDNA microarrays and oligonucleotide arrays. In one aspect, the invention provides a method of characterizing an RNA sequence of interest, comprising (a) amplifying a target RNA by a method described herein to generate labeled products; and (b) analyzing the labeled products. In some embodiments, the step of analyzing RNA products comprises determining amount of said products, whereby the amount of the RNA sequence of interest present in a sample is quantified. The polynucleotide products can be analyzed by, for example, contacting them with at least one probe. In some embodiments, the at least one probe is provided as a microarray. The microarray can comprise at least one probe immobilized on a solid or semi-solid substrate fabricated from a material selected from the group consisting of paper, glass, plastic, polypropylene, nylon, polyacrylamide, nitrocellulose, silicon, and optical fiber. A probe can be immobilized on the solid or semi-solid substrate in a two-dimensional configuration or a three-dimensional configuration comprising pins, rods, fibers, tapes, threads, beads, particles, microtiter wells, capillaries, and cylinders.

In another aspect, the invention provides methods of determining gene expression profile in a sample, the methods comprising: (a) amplifying at least one RNA sequence of interest in the sample using any of the methods described herein; and (b) determining amount of amplification products of each RNA sequence of interest, wherein each said amount is indicative of amount of each RNA sequence of interest in the sample, whereby the gene expression profile of the sample is determined.

In another aspect, the invention provides methods of preparing a subtractive hybridization probe, said methods comprising generating multiple single stranded polynucleotide, preferably DNA, copies of the complement of at least one RNA sequences of interest from a first RNA population using any of the methods described herein.

In another aspect, the invention provides methods of performing subtractive hybridization, said methods comprising: (a) generating multiple copies of the complement of at least one RNA sequence of interest from a first RNA population using any of the methods described herein; and (b) hybridizing the multiple copies to a second mRNA population, whereby a subpopulation of the second mRNA population forms a complex with a copy of the complement of at least one RNA sequence of interest. In embodiments in which DNA copies are generated, the methods further comprise: (c) cleaving RNA in the complex of step (b) with an enzyme that cleaves RNA from an RNA/DNA hybrid; and (d) amplifying an unhybridized subpopulation of the second mRNA population (using any method, including the methods described herein), whereby multiple copies of single stranded DNA complementary to the unhybridized subpopulation of the second mRNA population are generated.

In another aspect, the invention provides methods for differential amplification, the methods comprising: (a) generating multiple nucleic acid (generally DNA) copies of the complement of at least one RNA sequence of interest from a first RNA population using any of the methods described herein; (b) hybridizing the multiple copies to a second mRNA population, whereby a subpopulation of the second mRNA population forms a complex with a DNA copy; (c) cleaving RNA in the complex of step (b) with an enzyme that cleaves RNA from an RNA/DNA hybrid; and (d) amplifying an unhybridized subpopulation of the second mRNA population using any method, including those described herein, whereby multiple copies of single stranded DNA complementary to the unhybridized subpopulation of the second mRNA population are generated. These methods encompass steps (b), (c) and (d) if the copies used in the subtractive hybridization are generated using any of the methods described herein.

In another aspect, the invention provides methods for making a library, said method comprising preparing a subtractive hybridization probe as described herein, or differential amplification as described herein. Any of these applications can use any of the amplification methods (including various components and various embodiments of any of the components) as described herein.

The invention also provides compositions, kits, complexes, reaction mixtures and systems comprising various components (and various combinations of the components) used in the amplification methods described herein. The compositions may be any component(s), reaction mixture and/or intermediate described herein, as well as any combination thereof.

In some embodiments, the invention provides a composition comprising: (a) a first primer (which can be a random primer); (b) a second primer (which can be a random primer); and (c) a propromoter polynucleotide (which in some embodiments is a PTO). In some embodiments, these compositions may further comprise: (d) a third primer (which can be a random primer). In some of these embodiments, the first primer comprises a sequence that is not hybridizable to a target RNA. In some of these embodiments, the second primer comprises a sequence that is not hybridizable to a first primer extension product. In some embodiments, the third primer comprises a sequence that is not hybridizable to an RNA transcript. In some embodiments, the propromoter polynucleotide ((c), above) is capable of hybridizing to the complement of the 5' portion of the first primer.

The invention also provides compositions comprising a propromoter polynucleotide (such as a PTO) capable of hybridizing to a 3' portion of a second primer extension that is complement of a 5' portion of a first primer used to create first primer extension product.

The invention also provides compositions comprising (a) a first primer; (b) a second primer (which can be a random primer); and (c) a composite primer, wherein the composite primer comprises a 5' RNA portion and a DNA portion. In some embodiments, the invention provides a composition comprising: (a) a first primer (which can be a random primer) hybridizable to target RNA; (b) a second primer (which can be a random primer); and (c) a composite primer hybridizable to a second primer extension product. In some embodiments, the composition further comprises one or more of the following: DNA-dependent DNA polymerase, RNA-dependent DNA polymerase, and an agent (generally an enzyme) that cleaves RNA from an RNA/DNA heteroduplex.

The invention also provides compositions comprising the amplification products described herein. Accordingly, the invention provides a population of anti-sense RNA molecules which are copies of a target sequence, which are produced by any of the methods described herein. The invention also provides a population of anti-sense polynucleotides (generally DNA) molecules, which are produced by any of the methods described herein.

In another aspect, the invention provides compositions comprising any of the complexes (which are generally considered as intermediates with respect to the final amplification products) described herein (see also the figures for schematic depictions of examples of these various complexes). For example, the invention provides compositions comprising a complex of (a) a first primer extension product; and (b) a target RNA strand. In yet another aspect, the invention provides compositions comprising a complex of: (a) a first primer extension product; and (b) a second primer extension product. In another example, the invention provides compositions comprising a complex of (a) a second primer extension product; and (b) a propromoter polynucleotide (which can be a PTO). In some embodiments, the propromoter polynucleotide hybridizes to a sequence in the second primer extension product comprising the complement of the 5' portion of a first prime, wherein the first primer is extended to form the first primer extension product. In yet another example, the invention provides compositions comprising a complex of (a) a third primer extension product; and (b) a propromoter polynucleotide (which can be a PTO). In yet another example, the invention provides compositions comprising a complex of (a) a second primer extension product, generated by denaturation of a hybridized first and second primer extension product; and (b) a composite primer hybridizable to the second primer extension product.

In another aspect, the invention includes any one or more products (including intermediates) and compositions comprising the products (including intermediates) produced by any aspect of the methods of the invention. The products include libraries and any other population produced, which are generally based on the nature of the primer(s) used in the methods described herein.

In another aspect, the invention provides reaction mixtures (or compositions comprising reaction mixtures) which contain various combinations of components described herein. For example, the invention provides reaction mixtures comprising (a) a target RNA; (b) a first primer; (c) a second primer (which can be a random primer); (d) an RNA polymerase; and (e) a DNA polymerase. The reaction mixture could also further comprise an enzyme which cleaves RNA from an RNA/DNA hybrid, such as RNase H. A reaction mixture of the invention can also comprise a propromoter polynucleotide (which in some embodiments is a PTO).

In another aspect, the invention provides reaction mixtures comprising (a) a target RNA; (b) a first primer; (c) a second primer (which can be a random primer); (d) an RNA polymerase; (e) a DNA polymerase; and (f) a composite primer. The reaction mixture could also further comprise an enzyme which cleaves RNA from an RNA/DNA hybrid, such as RNase H.

In another aspect, the invention provides kits for conducting the methods described herein. These kits, in suitable packaging and generally (but not necessarily) containing suitable instructions for performing any of the methods of the invention described herein, including sequencing, detection of sequence alteration(s) (e.g., genotyping or nucleic acid mutation detection); determining presence or absence of a sequence of interest; gene expression profiling; subtractive hybridization; preparation of a subtractive hybridization probe; differential amplification; preparation of libraries (including cDNA and differential expression libraries); preparation of an immobilized nucleic acid (which can be a nucleic acid immobilized on a microarray), and characterizing (including detecting and/or quantifying and/or determining presence or absence of) amplified nucleic acid products generated by the methods of the invention. The kits further comprise one or more components used in the methods of the invention. For example, the invention provides kits that comprise a first primer that comprises a sequence the complement of which is hybridizable by a propromoter polynucleotide, and instructions for using the primer to amplify RNA. The invention also provides kits that further comprise a second primer and/or a third primer, and optionally instructions for using the primers to amplify RNA. The kits can contain further components, such as any of (a) a propromoter polynucleotide (such as a PTO); and (b) any of the enzymes described herein, such as an enzyme which cleaves RNA from an RNA/DNA hybrid (for example, RNaseH), DNA polymerase (RNA-dependent or DNA-dependent) and RNA polymerase. In another example, a kit can comprise (a) a composite primer; and (b) instructions for using the composite primer to amplify target RNA using the methods of the invention provided herein. The kit can comprise further components, including any of the enzymes described herein, such as an enzyme which cleaves RNA from an RNA/DNA hybrid (for example, RNaseH), and DNA polymerase (RNA-dependent or DNA-dependent). In another example, a kit comprises a first primer that comprises a sequence the complement of which is hybridizable by a propromoter polynucleotide, and instructions for using the primer to amplify RNA using any of the methods described herein. In another embodiment, the kit further comprises a second primer.

In another aspect, the invention provides systems for effecting the amplification methods described herein. For example, the invention provides systems for amplifying a target ribonucleic acid, comprising: (a) a first primer; (b) a second primer (which can be a random primer); (c) an RNA-dependent DNA polymerase; (d) a DNA-dependent DNA polymerase; (e) a propromoter polynucleotide (such as a PTO); and (f) an enzyme which cleaves RNA from an RNA/DNA hybrid (such as RNaseH). The systems may also comprise: (g) a third primer (which can be a random primer). As described herein, systems of the invention generally comprise one or more apparatuses appropriate for carrying out methods of the invention.

BRIEF DESCRIPTION OF THE DRAWINGS

FIG. 1 shows amplification of a target RNA using a polynucleotide comprising a propromoter to produces multiple copies of RNA transcripts complementary to the target RNA.

FIGS. 2A–B show further amplification of the RNA transcripts from the process of FIG. 1 to generate more RNA transcripts complementary to the target RNA.

FIGS. 3A–B show a diagrammatic representation of a linear RNA amplification process using a third primer that is a composite primer to generate single stranded DNA strands complementary to the target RNA.

MODES FOR CARRYING OUT THE INVENTION

Figure 1:
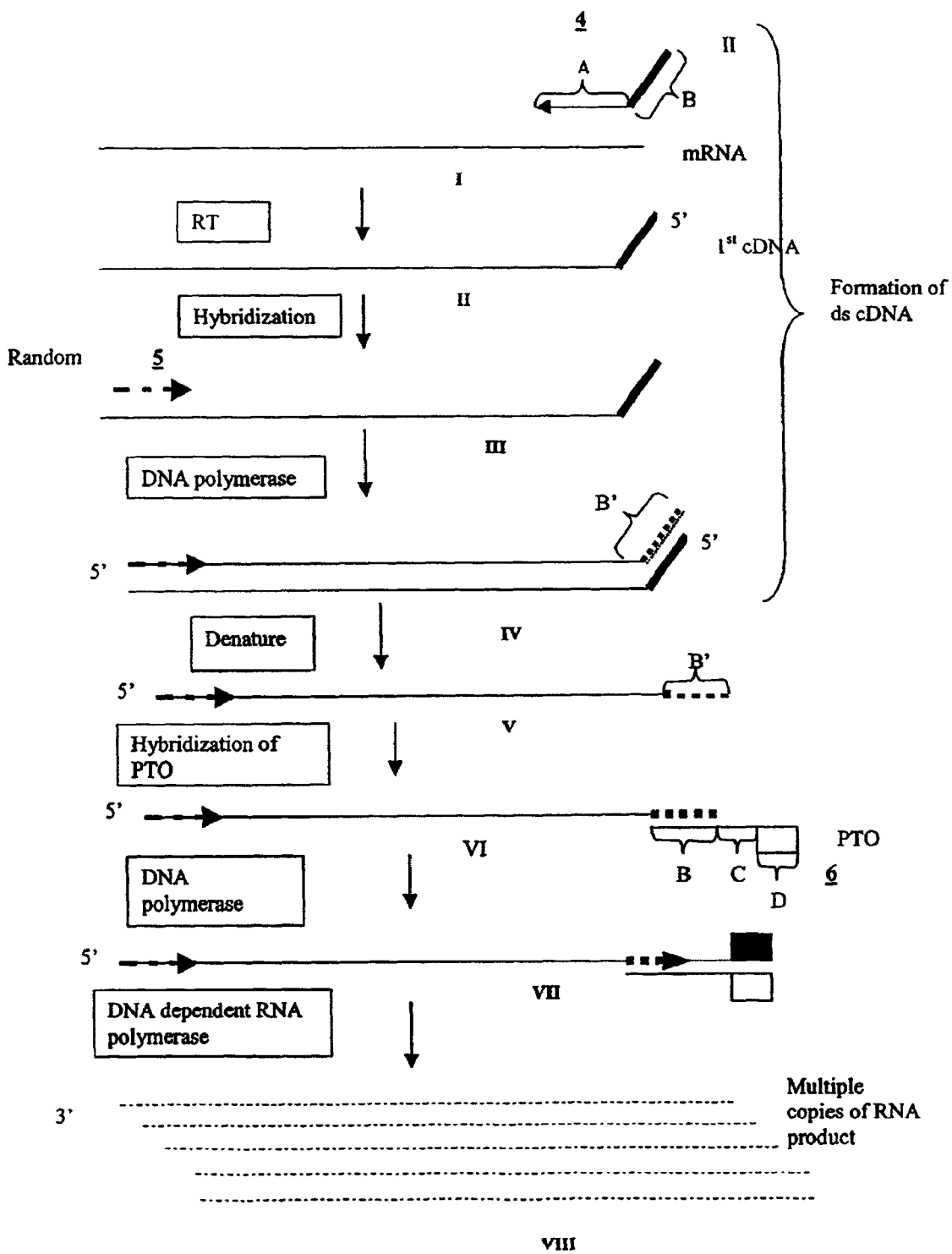
FIG. 1 is a diagrammatic representation of a linear RNA amplification process.

The invention provides methods, compositions and kits for amplifying polynucleotide sequences, specifically ribonucleic acid (RNA) sequences. The methods provide for amplification of a single RNA species or pool of RNA species. The methods can achieve exponential amplification, which would be particularly useful for amplification of very low amounts of RNA sequences in a biological sample. The methods are suitable for, for example, generation of libraries, including cDNA libraries. They generate single stranded RNA or, in some embodiments, single stranded DNA products, which are readily suitable for multiplex analysis by microarray technologies, as well as electrophoresis-based technologies such as differential display. The methods are amenable to automation and do not require thermal cycling. The methods generally comprise hybridizing a polynucleotide comprising a propromoter sequence to a primer extension product to generate an intermediate product capable of driving transcription, whereby RNA transcripts comprising sequences complementary to an RNA sequence of interest are produced. In another aspect, the methods comprise isothermal linear amplification of DNA copies complementary to the RNA sequence of interest using a denaturation step, a composite primer and strand displacement. See Kurn, U.S. Pat. No. 6,251,639 B1.

The methods of the invention are directed to the amplification of one or more species of RNA, such as a pool of RNA sequences, and is most particularly suitable for the amplification of all RNA (such as mRNA) sequences in a preparation of total RNA from a biological sample. Thus, one of the major advantages of the methods of the invention is the ability to amplify an entire pool of sequences, which is essential for the ability to analyze the gene expression profile in cells, such as the cells in a biological of interest sample. The methods of the invention have the potential of amplifying a multiplicity, more preferably a large multiplicity, and most preferably all RNA (such as mRNA) sequences in a sample.

Insofar as many mRNAs have a unique polyA 3'-end, the amplification initiated from the 3'-end sequence of mRNAs is most common for preparation of cDNA libraries and subsequent sequence analysis for determination of gene expression profiling or other applications. The methods of the invention are similarly suited for preparation of libraries of amplified 3'-portions of mRNAs. The sequence of the first primer used in the methods of invention can be designed to be complementary to a multiplicity, or all, of the mRNA species in the sample by using random sequences, according to methods known in the art.

Various methods for mRNA amplification have been described. U.S. Pat. Nos. 744,308; 6,143,495; EP 0971039A2; EP 0878553A2. Most of these methods are transcription based, wherein a promoter for RNA polymerase is incorporated into a double stranded cDNA by a primer comprising a propromoter sequence at the 5'-end which hybridizes to target RNA. These primers can non-specifically bind to template RNA. Insofar as a DNA polymerase has a high affinity for primer hybridized to a template nucleic acid with a free 3' end, i.e. a substrate for primer extension by the polymerase, it is highly probable that a primer comprising a propromoter sequence at the 5' end may non-specifically incorporate the promoter sequence into an amplification product. This results in uncontrolled production of transcription products. The appending of a double stranded promoter by a propromoter polynucleotide, as described herein, provides for increased specificity and control of the transcription-based generation of amplification product.

In one aspect, the invention works as follows: generation of multiple copies of the complementary sequence of an RNA sequence of interest is achieved by using a first primer (which can be a specific or random primer) that comprises a sequence (generally, in its 5' portion) the complement of which is hybridizable by a polynucleotide comprising a propromoter. In some embodiments, the sequence the complement of which is hybridizable by a polynucleotide comprising a propromoter is a sequence that is hybridizable to a target RNA when the primer is hybridized to the target RNA. In other embodiments, the sequence the complement of which is hybridizable by a polynucleotide comprising a propromoter is a sequence that is not hybridizable to a target RNA when the primer is hybridized to the target RNA (thus forming a tail when the primer is hybridized to a target). The extension of the first primer along a target RNA by an RNA-dependent DNA polymerase results in the generation of an intermediate polynucleotide (first primer extension product) that has at least one defined end (the first primer end). After cleavage of the template RNA from a complex comprising the target RNA and first primer extension product, a second primer (which can be a specific or random primer) is then hybridized to the first DNA strand (first primer extension product) and extended to form a complex of first and second primer extension products that at one end comprises a sequence to which a polynucleotide comprising a propromoter is hybridizable. The second primer is any sequence that is hybridized to the first DNA strand such that it is capable of being extended by a DNA polymerase along a first DNA strand to generate a second DNA strand. Thus, in some embodiments, the second primer is an oligonucleotide (that is separately provided). In other embodiments, it is or comprises a sequence of the first DNA strand (generally at the 3' end) that is hybridized to a sequence in the first DNA strand (for example, a hairpin or self-annealed structure). Following denaturation of the complex, a polynucleotide comprising a propromoter is hybridized to the second primer extension product and the 3' end of the primer extension product is extended along the propromoter oligonucleotide (if there is any overhang) to generate a double stranded promoter region. RNA transcription driven by this promoter results in generation of multiple copies of RNA transcripts comprising the complementary sequence of the RNA sequence of interest. In some embodiments involving cyclical amplification (also referred to herein as "exponential" amplification), these RNA transcripts, and optionally RNA transcripts generated in subsequent steps, are hybridized with a third primer (which may or may not be the same as the second primer, and which may be a specific or random primer). The third primer is extended to form a complex comprising the RNA transcript and a third primer extension product (which constitutes a DNA/RNA heteroduplex). Cleavage of the RNA transcript results in a single stranded third primer extension product to which a propromoter polynucleotide hybridizes. If necessary (i.e., if there is an overhang), the third primer extension product is extended along the propromoter polynucleotide to generate a double stranded promoter region. RNA transcription driven by this promoter results in generation of multiple copies of RNA transcripts comprising the complementary sequences of the RNA sequence of interest. Hybridization of third primers to these RNA transcripts initiates a cyclical process leading to further amplification.

Accordingly, the invention provides methods of producing at least one copy of the complementary sequence of an RNA sequence of interest, said method comprising combining and reacting the following: (a) a target RNA comprising an RNA sequence of interest; (b) a first primer that hybridizes to the target RNA; (c) a second primer that is hybridizable to an extension product of the first primer; (d) an RNA-dependent DNA polymerase; (e) a DNA-dependent DNA polymerase; (f) an enzyme that cleaves RNA from an RNA/DNA hybrid; (g) a propromoter polynucleotide comprising a propromoter and a region which hybridizes to an extension product of the second primer; (h) deoxyribonucleoside triphosphates or suitable analogs; (i) ribonucleoside triphosphates and suitable analogs; and (j) an RNA polymerase. In embodiments involving cyclical amplification (interchangeably termed "exponential" amplification, herein), the following are also included in the amplification reaction (either at the same time as the components listed above or added separately): (k) optionally a third primer (which may or may not be the same as the second primer) that hybridizes to an RNA transcript comprising sequences complementary to the sequence of the target RNA; and (l) optionally a second polynucleotide comprising a propromoter and a region which hybridizes to a single stranded third primer extension product (this polynucleotide may or may not be the same as the polynucleotide described in (g) above).

As is evident to one skilled in the art, by this disclosure, the reactions described may be simultaneous or sequential, as such, the invention includes these various embodiments and combinations.

In some embodiments, the invention provides methods of producing at least one copy of the complementary sequence of an RNA sequence of interest, said method comprising combining and reacting the following: (a) a single stranded second primer extension product resulting from denaturation of a complex of first and second primer extension products as described herein; (b) a propromoter polynucleotide comprising a propromoter and a region which hybridizes to a second primer extension product; (c) ribonucleoside triphosphates and suitable analogs; and (d) an RNA polymerase.

In embodiments involving cyclical amplification ("exponential" amplification), the following may also included in the amplification reaction (either at the same time as the components listed above or added separately): (e) optionally a third primer (which may or may not be the same as the second primer) that hybridizes to an RNA transcript comprising sequences complementary to the sequence of the target RNA; and (f) optionally a second polynucleotide comprising a propromoter and a region which hybridizes to a single stranded third primer extension product (this polynucleotide may or may not be the same as the polynucleotide described in (b) above). In some embodiments involving cyclical amplification, said method comprises combining and reacting (under suitable conditions and reagent such that multiple copies of a polynucleotide sequence complementary to an RNA sequence of interest are produced) the following: (a) an RNA transcript generated from the complex of the first propromoter polynucleotide and second primer extension product; (b) a third primer (which may or may not be the same as the second primer) that hybridizes to the RNA transcript; (c) a second polynucleotide comprising a propromoter and a region which hybridizes to a single stranded third primer extension product (this polynucleotide may or may not be the same as the propromoter polynucleotide in the complex from which the RNA transcript in step (a) is generated).

In another aspect, the invention provides a method of generating multiple copies of a polynucleotide sequence complementary to an RNA sequence of interest as follows: generation of multiple copies of the complementary sequence of an RNA sequence of interest is achieved by using a first primer (which can be a specific or random primer) that comprises a sequence in its 5' portion that is not hybridizable to target RNA (thus forming a tail when the primer is hybridized to a target under conditions when the first primer hybridizes to template RNA). The extension of the first primer along a target RNA by an RNA-dependent DNA polymerase results in the generation of an intermediate polynucleotide (first strand cDNA) that has at least one defined end comprising the complement of the first primer sequence. After cleavage of the template RNA from a complex comprising the target RNA and first strand cDNA, a second primer (which can be a specific or random primer) is then hybridized to the first strand cDNA) and extended to form a complex of first and second strand cDNAs that at (at least) one end has a defined end comprising the first primer sequence and the complement of the first primer sequence. The second primer is any sequence that is hybridized to the first DNA strand such that it is capable of being extended by a DNA polymerase along a first DNA strand to generate a second DNA strand. Thus, in some embodiments, the second primer is an oligonucleotide (that is separately provided). In other embodiments, it comprises a sequence of the first DNA strand (generally at the 3' end) that is hybridized to a sequence in the first DNA strand (for example, a hairpin or self-annealed structure). In other embodiment, the second primer comprises one or more fragments of the target RNA sequence that remains hybridized to the first primer extension product (after cleavage of the initial complex comprising the target RNA and first primer extension product). The complex of first and second strand cDNAs (wherein the second strand cDNA comprises a 3' end portion that is the complement of the first primer sequence) is then denatured to form single stranded first strand cDNA and second strand cDNA.

The single stranded second strand cDNA is the substrate for isothermal linear amplification using a composite primer and strand displacement as follows: a composite primer comprising a 5'-RNA portion and a DNA portion hybridizes to the 3'-portion of the second strand cDNA, generally to the 3'-portion of the second strand cDNA, and is extended along the second strand cDNA by a DNA polymerase to form a double stranded complex comprising an RNA/DNA hybrid portion at one end of the complex. An enzyme which cleaves RNA from an RNA/DNA hybrid (such as RNase H) cleaves RNA sequence from the hybrid, leaving a sequence on the second strand cDNA available for binding by another composite primer. Another first (composite) strand cDNA is produced by DNA polymerase, which displaces the previously bound cleaved first strand cDNA, resulting in displaced cleaved first strand cDNA. The displaced cleaved first strand cDNA product comprises single stranded DNA complementary to the RNA sequence of interest. Kurn, U.S. Pat. No. 6,251,639 B1.

Any of the methods of the invention can be used to generate polynucleotide (generally, RNA or DNA) products that are labeled by incorporating labeled nucleotides into appropriate steps of the methods. These labeled products are particularly suitable for quantification and/or identification by methods known in the art, which include the use of arrays such as cDNA microarrays and oligonucleotide arrays.

In some embodiments, the invention provides methods of sequencing RNA sequences. For sequencing methods based on methods described herein, the appropriate rNTPs, or analogs thereof, which may be labeled or unlabeled, are used. Accordingly, the invention provides methods of sequencing a target RNA comprising a sequence of interest based on the methods described above, wherein rNTPs and rNTP analogs which are primer elongation terminators, which may be labeled or unlabeled, are used, and the amplification product is analyzed for sequence information, as described below. For sequencing methods based on methods described herein wherein the amplified product is DNA, the appropriate dNTPs, or analogs thereof, which may be labeled or unlabeled, are used.

In other embodiments, the invention provides methods of detecting nucleic acid sequence mutations. In one embodiment, the amplification products are used to detect and/or identify single strand conformation polymorphisms in a target RNA.

The invention provides methods to characterize (for example, detect and/or quantify and/or determine presence or absence of) an RNA sequence of interest by generating polynucleotide (generally RNA or DNA) products using amplification methods of the invention, and analyzing the products by detection/quantification methods such as those based on array technologies or solution phase technologies. Generally, but not necessarily, these amplified products are labeled.

In another aspect, the invention provides a method of characterizing an RNA sequence of interest, comprising (a) amplifying a target RNA by a method described herein to generate labeled products; and (b) analyzing the labeled polynucleotide (generally, RNA or DNA) products. In some embodiments, the step of analyzing products comprises determining amount of said products, whereby the amount of the RNA sequence of interest present in a sample is quantified. The polynucleotide (generally, DNA or RNA) products can be analyzed by, for example, contacting them with at least one probe. In some embodiments, the at least one probe is provided as a microarray. The microarray can comprise at least one probe immobilized on a solid or semi-solid substrate fabricated from a material selected from the group consisting of: paper, glass, ceramics, plastic, polypropylene, polystyrene, nylon, polyacrylamide, nitrocellulose, silicon, other metals, and optical fiber. A probe can be immobilized on the solid or semi-solid substrate in a two-dimensional configuration or a three-dimensional configuration comprising pins, rods, fibers, tapes, threads, beads, particles, microtiter wells, capillaries, and cylinders.

In another aspect, the invention provides methods of determining gene expression profile in a sample, the methods comprising: (a) amplifying at least one RNA sequence of interest in the sample using any of the methods described herein; and (b) determining amount of amplification products of each RNA sequence of interest, wherein each said amount is indicative of amount of each RNA sequence of interest in the sample, whereby the gene expression profile of the sample is determined.

In another embodiment, the invention provides methods of generating libraries (including cDNA libraries and subtractive hybridization libraries), said methods comprising: amplifying at least one RNA sequences of interest using any of the methods described herein to generate single stranded nucleic acid product, and methods of generating and using subtractive hybridization probes, methods for subtractive hybridization, methods for differential amplification, and methods of generating subtractive hybridization libraries.

Various methods for the detection and quantification of gene expression levels have been developed in recent years. For example, microarrays, in which either defined cDNAs or oligonucleotides are immobilized at discrete locations on, for example, solid or semi-solid substrates, or on defined particles, enables the detection and/or quantification of the expression of a multitude of genes in a given specimen.

Using these previously known methods to detect and/or quantify multiple mRNA species in a sample, which in turn is a measure of gene expression profiling, generally requires direct labeling of cDNA, which requires a large amount of input total RNA, in part because mRNA represents only a small subset of the total RNA pool. Thus, when using total RNA preparations from a given cell or tissue sample, the analysis of gene expression in the sample using methods such as arrays requires a substantial amount of input RNA, which generally ranges from 50 to 200 µg. Similarly, 2 to 5 µg of mRNA purified from a total RNA preparation would generally be required for a single analysis of gene expression profiling using array technologies. This is a clear limitation of methods such as those based on array technology, insofar as the number of cells, or size of tissue specimen required is very large, and these cells or tissue specimens are often scarcely available for testing or are too precious. This limitation is especially severe in the study of clinical specimens, where the cells to be studied are rare and/or difficult to cultivate in vitro, and in high throughput screening of libraries of effector molecules.

General Techniques

The practice of the invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the invention can be generated using standard techniques known in the art.

Definitions

A "target sequence," "target nucleic acid," or "target RNA," as used herein, is a polynucleotide comprising a sequence of interest, for which amplification is desired. The target sequence may be known or not known, in terms of its actual sequence. In some instances, the terms "target" and "template", and variations thereof, are used interchangeably.

"Amplification," as used herein, generally refers to the process of producing multiple copies of a desired sequence. "Multiple copies" mean at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template, or a non-target sequence introduced through a primer), and/or sequence errors that occur during amplification. "Amplifying" a sequence may generally refer to making copies of a sequence or its complement, with the understanding that, as stated above, copying does not necessarily mean perfect sequence complementarity or identity with respect to the template sequence.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O) R, P(O)OR', CO or CH$_2$ ("formacetal"), in which each R or R' is independently H or substituted or unsubstituted alkyl (1–20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "labeled dNTP," or "labeled rNTP," as used herein, refers, respectively, to a dNTP or rNTP, or analogs thereof, that is directly or indirectly attached with a label. For example, a "labeled" dNTP or rNTP, may be directly labeled with, for example, a dye and/or a detectable moiety, such as a member of a specific binding pair (such as biotin-avidin). A "labeled" dNTP or rNTP, may also be indirectly labeled by its attachment to, for example, a moiety to which a label is/can be attached. A dNTP or rNTP, may comprise a moiety (for example, an amine group) to which a label may be attached following incorporation of the dNTP or rNTP into an extension product. Useful labels in the present invention include fluorescent dyes (e.g., fluorescein isothiocyanate, Texas red, rhodamine, green fluorescent protein and the like), radioisotopes (e.g., $^3$H, $^{35}$S, $^{32}$P, $^{33}$P, $^{125}$I, or $^{14}$C), enzymes (e.g., LacZ, horseradish peroxidase, alkaline phosphatase), digoxigenin, and colorimetric labels such as colloidal gold or colored glass or plastic (e.g., polystyrene, polypropylene, latex, etc.) beads. Various anti-ligands and ligands can be used (as labels themselves or as a means for attaching a label). In the case of a ligand that has a natural anti-ligand, such as biotin, thyroxine and cortisol, the ligand can be used in conjunction with labeled anti-ligands.

The "type" of dNTP or rNTP, as used herein, refers to the particular base of a nucleotide, namely adenine, cytosine, thymine, uridine, or guanine.

"Oligonucleotide," as used herein, generally refers to short, generally single stranded, generally synthetic polynucleotides that are generally, but not necessarily, less than about 200 nucleotides in length. Oligonucleotides in the invention include the first, second, and third primers, and propromoter polynucleotide (such as the PTO). The terms "oligonucleotide" and "polynucleotide" are not mutually exclusive. The description above for polynucleotides is equally and fully applicable to oligonucleotides.

A "primer" is generally a nucleotide sequence (i.e. a polynucleotide), generally with a free 3'-OH group, that hybridizes with a template sequence (such as a target RNA, or a primer extension product) and is capable of promoting polymerization of a polynucleotide complementary to the template. A "primer" can be, for example, an oligonucleotide. It can also be, for example, a sequence of the template (such as a primer extension product or a fragment of the template created following RNase cleavage of a template-DNA complex) that is hybridized to a sequence in the template itself (for example, as a hairpin loop), and that is capable of promoting nucleotide polymerization. Thus, a primer can be an exogenous (e.g., added) primer or an endogenous (e.g., template fragment) primer.

A "random primer," as used herein, is a primer that comprises a sequence that is designed not necessarily based on a particular or specific sequence in a sample, but rather is based on a statistical expectation (or an empirical observation) that the sequence of the random primer is hybridizable (under a given set of conditions) to one or more sequences in the sample. The sequence of a random primer (or its complement) may or may not be naturally-occurring, or may or may not be present in a pool of sequences in a sample of interest. The amplification of a plurality of RNA species in a single reaction mixture would generally, but not necessarily, employ a multiplicity, preferably a large multiplicity, of random primers. As is well understood in the art, a "random primer" can also refer to a primer that is a member of a population of primers (a plurality of random primers) which collectively are designed to hybridize to a desired and/or a significant number of target sequences. A random primer may hybridize at a plurality of sites on a nucleic acid sequence. The use of random primers provides a method for generating primer extension products complementary to a target polynucleotide which does not require prior knowledge of the exact sequence of the target.

"Protopromoter sequence," and "propromoter sequence," as used herein, refer to a single-stranded DNA sequence region which, in double-stranded form is capable of mediating RNA transcription. In some contexts, "protopromoter sequence," "protopromoter," "propromoter sequence," "propromoter," "promoter sequence," and "promoter" are used interchangeably.

A "propromoter polynucleotide," as used herein, refers to a polynucleotide comprising a propromoter sequence. Example of a propromoter polynucleotide is a propromoter template oligonucleotide (PTO).

"Propromoter template oligonucleotide (PTO)" and "promoter template oligionucleotide (PTO)" as used herein, refer to an oligonucleotide that comprises a propromoter sequence and a portion, generally a 3' portion, that is hybridizable (under a given set of conditions) to the 3' region of a primer extension product. The propromoter sequence and the hybridizable portion may be the same, distinct or overlapping nucleotides of an oligonucleotide.

To "inhibit" is to decrease or reduce an activity, function, and/or amount as compared to a reference.

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final amplification product(s). An example of a complex is a nucleic acid duplex comprising a first primer extension product and a second primer extension product.

"Denaturing," or "denaturation of" a complex comprising two polynucleotides (such as a first primer extension product and a second primer extension product) refers to dissociation of two hybridized polynucleotide sequences in the complex. The dissociation may involve a portion or the whole of each polynucleotide. Thus, denaturing or denaturation of a complex comprising two polynucleotides can result in complete dissociation (thus generating two single stranded polynucleotides), or partial dissociation (thus generating a mixture of single stranded and hybridized portions in a previously double stranded region of the complex).

A "portion" or "region," used interchangeably herein, of a polynucleotide or oligonucleotide is a contiguous sequence of 2 or more bases. In other embodiments, a region or portion is at least about any of 3, 5, 10, 15, 20, 25 contiguous nucleotides.

A region, portion, or sequence which is "adjacent" to another sequence directly abuts that region, portion, or sequence.

A "reaction mixture" is an assemblage of components, which, under suitable conditions, react to form a complex (which may be an intermediate) and/or a product(s).

"A", "an" and "the", and the like, unless otherwise indicated include plural forms.

"Comprising" means including.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in a sequence of interest in comparison to a reference sequence. A reference sequence can be a wild type sequence or a sequence to which one wishes to compare a sequence of interest. A sequence mutation includes single nucleotide changes, or alterations of more than one nucleotide in a sequence, due to mechanisms such as substitution, deletion or insertion. Single nucleotide polymorphism (SNP) is also a sequence mutation as used herein.

"Single stranded conformation polymorphism," and "SSCP," as used herein, generally refer to the specific conformation of a single stranded nucleic acid as is affected by its specific nucleic acid sequence. Alteration of the sequence of the single stranded polynucleotide, such as single nucleotide substitution, deletions or insertions, result in change, or polymorphism, of the conformation of the single stranded polynucleotide. The conformation of the polynucleotide is generally detectable, identifiable and/or distinguishable using methods known in the art, such as electrophoretic mobility as measured by gel electrophoresis, capillary electrophoresis, and/or susceptibility to endonuclease digestion.

"Microarray" and "array," as used interchangeably herein, comprise a surface with an array, preferably ordered array, of putative binding (e.g., by hybridization) sites for a biochemical sample (target) which often has undetermined characteristics. In a preferred embodiment, a microarray refers to an assembly of distinct polynucleotide or oligonucleotide probes immobilized at defined positions on a substrate. Arrays are formed on substrates fabricated with materials such as paper, glass, ceramic, plastic (e.g., polypropylene, nylon, polystyrene), polyacrylamide, nitrocellulose, silicon or other metals, optical fiber or any other suitable solid or semisolid support, and configured in a planar (e.g., glass plates, silicon chips) or three-dimensional (e.g., pins, fibers, beads, particles, microtiter wells, capillaries) configuration. Probes forming the arrays may be attached to the substrate by any number of ways including (i) in situ synthesis (e.g., high-density oligonucleotide arrays) using photolithographic techniques (see, Fodor et al., *Science* (1991), 251:767–773; Pease et al., *Proc. Natl. Acad. Sci. U.S.A.* (1994), 91:5022–5026; Lockhart et al., *Nature Biotechnology* (1996), 14:1675; U.S. Pat. Nos. 5,578,832; 5,556,752; and 5,510,270); (ii) spotting/printing at medium to low-density (e.g., cDNA probes) on glass, nylon or nitrocellulose (Schena et al, *Science* (1995), 270:467–470, DeRisi et al, *Nature Genetics* (1996), 14:457–460; Shalon et al., *Genome Res.* (1996), 6:639–645; and Schena et al., *Proc. Natl. Acad. Sci. U.S.A.* (1995), 93:10539–11286); (iii) by masking (Maskos and Southern, Nuc. Acids. Res. (1992), 20:1679–1684) and (iv) by dot-blotting on a nylon or nitrocellulose hybridization membrane (see, e.g., Sambrook et al., Eds., 1989, Molecular Cloning: A Laboratory Manual, 2nd ed., Vol. 1–3, Cold Spring Harbor Laboratory (Cold Spring Harbor, N.Y.)). Probes may also be noncovalently immobilized on the substrate by hybridization to anchors, by means of magnetic beads, or in a fluid phase such as in microtiter wells or capillaries. The probe molecules are generally nucleic acids such as DNA, RNA, PNA, and cDNA but may also include proteins, polypeptides, oligosaccharides, cells, tissues and any permutations thereof which can specifically bind the target molecules.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The 3' most nucleotide(s) can be preferably from about 1 to about 20, more preferably from about 3 to about 18, even more preferably from about 5 to about 15 nucleotides.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. The 5' most nucleotide(s) can be preferably from about 1 to about 20, more preferably from about 3 to about 18, even more preferably from about 5 to about 15 nucleotides.

As is well understood by those skilled in the art, a "tail" sequence of a primer is a sequence not hybridizable to the target sequence under conditions in which other region(s) or portion(s) of the primer hybridizes to the target.

Amplifcation Methods of the Invention

The following are examples of the amplification methods of the invention. It is understood that various other embodiments may be practiced, given the general description provided above.

Methods of generating multiple copies of (amplifying) an RNA sequence complementary to an RNA sequence of interest are provided. In some aspect, the amplification methods of the invention include a transcription step. In a first embodiment of these methods, linear nucleic acid amplification is achieved based on hybridizing a propromoter polynucleotide to a primer extension product to generate an intermediate product capable of driving transcription, whereby RNA transcripts comprising sequences complementary to an RNA sequence of interest are produced. In a second embodiment of these methods, exponential amplification is achieved by subjecting amplified RNA products generated in the process of the first embodiment of this method and in subsequent amplification to cyclical amplification.

In embodiments of the amplification methods of the invention which include a transcription step generally provide as follows: if a primer extension product that is to be transcribed comprises a propromoter sequence, a double stranded promoter region is generally generated by hybridizing a polynucleotide comprising a propromoter (also referred to herein as "propromoter polynucleotide") to the primer extension product. If a primer extension product does not comprise a desired propromoter sequence, the transcription step is generally dependent on the incorporation of an RNA polymerase propromoter sequence, by use of a propromoter polynucleotide such as a promoter sequence oligonucleotide (PTO). A propromoter polynucleotide such as the PTO can serve as a template for extension of a single stranded primer extension product and formation of a partial duplex comprising a double stranded promoter at one end. The ability to hybridize a single stranded primer extension product to the propromoter polynucleotide (such as a PTO) is generally achieved by creating a primer extension product with a defined 3' end sequence, which is complementary to the 3' end sequence of the propromoter polynucleotide.

In another aspect, the invention provides a method for generating multiple copies (amplifying) of a polynucleotide (DNA) sequence complementary to an RNA sequence of interest using a first primer and a composite primer.

One aspect of the methods of the invention includes the design of primers which are able to hybridize to RNA sequences, such as a plurality of RNA sequences, for initiation of primer extension and production of amplification substrates and products.

Methods of Amplifying an RNA Sequence of Interest

Nucleic Acid Sequence Amplification Using a First Primer and a Propromoter Polynucleotide, and a Propromoter Polynucleotide The invention provides methods of generating multiple copies of the complementary sequence of an RNA sequence of interest by using a primer that comprises a sequence that when introduced into the amplification steps result in generation of an intermediate polynucleotide to which a propromoter polynucleotide can hybridize. The primer is designed to comprise a sequence the complement of which is hybridizable by a propromoter polynucleotide. Generally, this sequence is in the 5' portion of the primer. The sequence can be a sequence (the complement of which is hybridizable by the propromoter polynucleotide used) that is hybridizable to a target RNA, or a sequence (the complement of which is hybridizable by the propromoter polynucleotide used) that is not hybridizable to a target RNA. In some embodiments, linear amplification is achieved. In other embodiments wherein amplified RNA products are subjected to further rounds of amplification, cyclical, and thus exponential, amplification is achieved.

A schematic exemplary depiction of one embodiment of the linear methods of the invention is provided in FIG. 1. A schematic depiction of one embodiment of the exponential amplification methods of the invention is provided in FIG. 2. An embodiment of the linear amplification method of the invention illustrated in FIG. 1 employs two oligonucleotides which are combined with the sample as shown in the figure: a) a first primer (labeled "4"), which can be composed of two portions, a 3' portion (labeled "A"), and a 5' portion (labeled "B"); and b) a second primer (labeled 5). The exponential method of the invention as illustrated in FIGS. 2A–B employs three oligonucleotides which are combined with the sample as shown in the figure: a) a first primer (labeled "4") which can be composed of two portions, a 3' portion (labeled "A"); and a 5' portion (labeled "B"); b) a second primer (labeled "5"); and c) a propromoter polynucleotide, such as a promoter template oligonucleotide (PTO), (labeled "6").

Figure 2A:
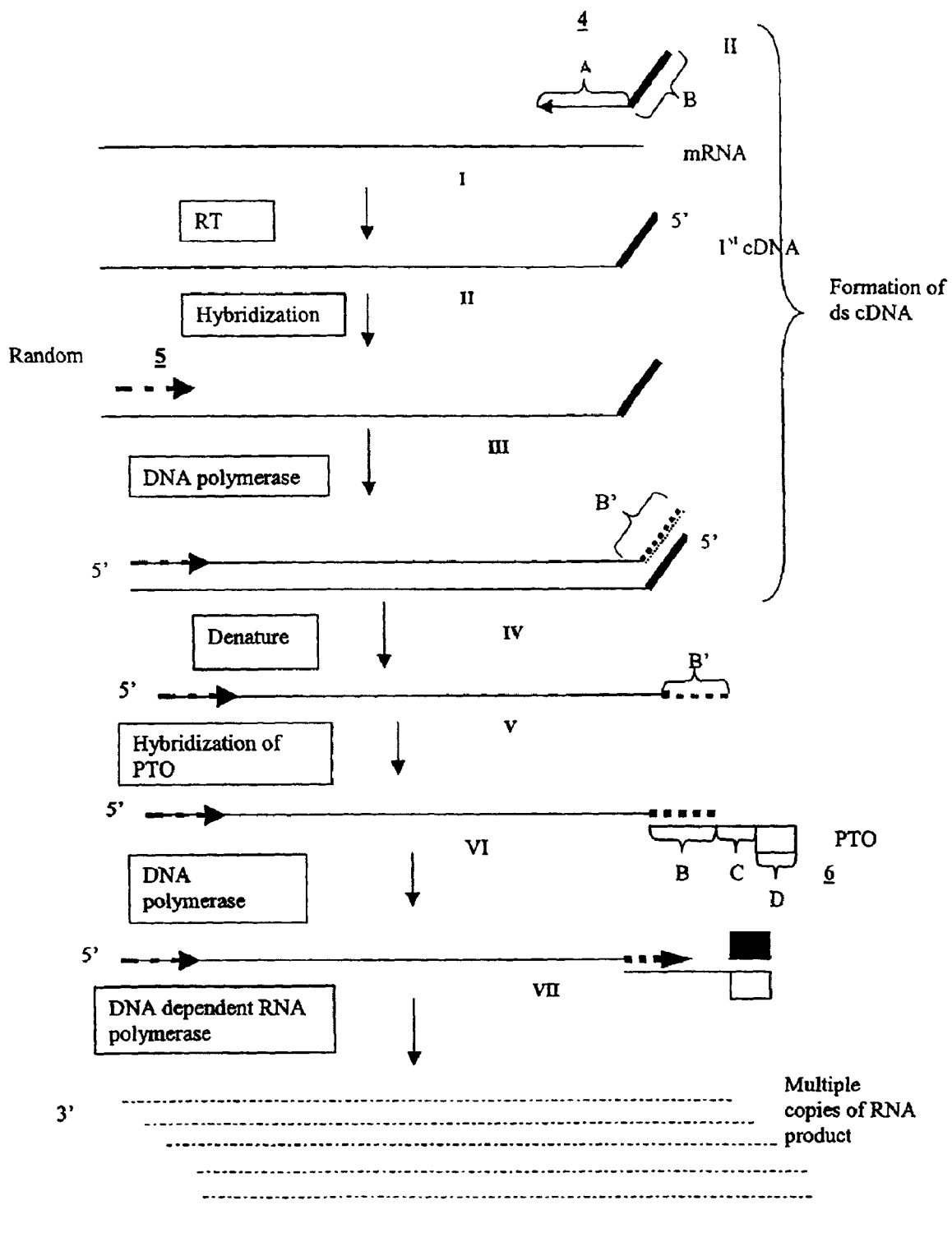

The 3' portion of the first primer illustrated in FIGS. 1 and 2A can be designed in any of a number of ways (in terms of sequence), depending on which type, class, population, and/or species of RNA is desired to be amplified. In some embodiments, the 3' portion of the first primer, as illustrated in FIGS. 1 and 2A, comprises a sequence complementary to the poly-A tail of mRNA, and may further comprise additional random sequences (generally not complementary to a poly-A sequence) at the 3' end of the 3' portion. In other embodiments, the 3' portion of the first primer is a random primer comprising sequences which are hybridizable to a multiplicity of RNA species (which may range from 2 or more to many hundred or thousands or more). Random primers are known in the art, for example, they have been used extensively in the preparation of cDNA libraries using PCR-based procedures. As is well understood in the art, a "random primer" can refer to a primer that is a member of a population of primers (a plurality of random primers) which collectively are designed to hybridize to a desired and/or a significant number of target sequences. A random primer may hybridize at a plurality of sites on a nucleic acid sequence.

In other embodiments, the 3' portion of the first primer can comprise a sequence complementary or hybridizable to a specific RNA or family of RNAs (or portions thereof).

In some embodiments as illustrated in FIGS. 1 and 2A, the 5' portion of the first primer can be a sequence not hybridizable to the target sequence (under conditions in which the 3' portion hybridizes to RNA target), e.g., a sequence forming a "tail" when the primer is hybridized to a target. This "tail" sequence generally is incorporated into the first primer extension product (first strand cDNA), and the complement of this tail will be incorporated at the 3' end of the second primer extension product (second strand EDNA). Accordingly, in some embodiments, the first primer is a mixture of first primers which comprise the same 5' DNA portion and a multiplicity of 3' DNA portions selected to amplify a multiplicity (which can be small to very large) of RNA sequences of interest. In other embodiments, the 5' portion of the first primer can be hybridizable to the target RNA.

The second primer as illustrated in FIGS. 1 and 2A may comprise random sequences, which are known in the art, and that are complementary to sequences of a plurality of the first cDNA strands produced. The 3' end of the propromoter polynucleotide is preferably, but not necessarily, non-extendable. The 3' portion of the PTO generally comprises a sequence that is typically identical to the B sequence of the first primer 4.

Primer 2 as illustrated in FIGS. 1 and 2A can be, but is not necessarily, composed of DNA and can comprise two sections (interchangeably called "portions" or "regions"). The 3' portion of primer 2 can be selected for random priming of many, most and/or all possible mRNA sequences in a biological sample. Random primers are known in the art, for example, they have been used extensively in the preparation of cDNA libraries using PCR-based procedures. In some embodiments, the hybridizable sequence of the second primer is designed based on a known sequence of the desired binding site on a first strand cDNA. In other embodiments, the second primer comprises a strand switch oligonucleotide, described in U.S. Pat. Nos. 5,962,271 and 5,962,272, which is hybridizable to the Cap sequences present on mRNA and causes the reverse transcriptase to switch from the mRNA template to the switch oligonucleotide, permitting generation of a second strand cDNA primed by the "switch oligonucleotide".

Alternatively, a homopolymeric tail is added to the 3'terminus of the first primer extension product, and the second primer comprises the complement of the homopolymeric tail.

In some embodiments, the second primer comprises DNA. In other embodiments, the second primer consists of DNA. In other embodiments, as described herein, the second primer is a fragment of the target RNA, with the fragment being generated by cleavage of the RNA target.

The 5' portion of primer 2 can be a sequence which is not complementary and not substantially hybridizable to a specific target sequence, i.e., it would not hybridize (under conditions in which the 3' portion hybridizes to RNA target) and would constitute a tail. The "tail" sequence would generally be incorporated into the second primer extension product.

A promoter template oligonucleotide, 3 (PTO), can be designed as follows: the 3' end of the propromoter polynucleotide is preferably, but not necessarily, non-extendable. The 3' portion of the PTO generally comprises a sequence that is typically identical to the B sequence of the first primer 4. The 5'-most portion of the PTO is a promoter sequence for a DNA-dependent RNA polymerase, which, as described above, is used in certain embodiments of the amplification methods of the invention. Generally, the sequence between these two sections is designed for optimal transcription by the polymerase of choice. Criteria for selection and design of this sequence are known in the art.

As illustrated in FIG. 1, one embodiment of the process of the linear amplification methods of the invention is as follows:

A) Formation of Double Stranded cDNA Substrate from Target RNA

1. Primer 4 binds to a target RNA by hybridization of its 3' end to the target to form complex I. The most commonly used initiation site for binding of the first primer to generate first strand cDNA is the 3' end poly-A sequence of mRNA and the immediate adjacent nucleotides. Binding of the primer to these immediate adjacent nucleotides can be achieved by including partially random sequences (other than sequence complementary to poly-A sequence of a target mRNA) at the 3' end of the primer. Criteria for primer designs for this purpose are known in the art, for example in the selection of primer sequences in the generation of libraries (including cDNA libraries). In cases where it is desired to produce libraries of sequences of a pre-defined family of mRNA, such as for example preparation of libraries from an immunoglobulin chain, the A sequence of the first primer could comprise a sequence which is well preserved in all members of the family of RNA from the immunoglobulin chain.

2. Primer extension along the RNA strand of complex I is carried out by an RNA-dependent DNA polymerase such as reverse transcriptase (labeled "RT"), to form an RNA/DNA hybrid duplex. RNase H degrades the RNA strand of the hybrid duplex to produce a first cDNA strand (labeled "I"). The RNase H activity may be supplied by the RNA-dependent DNA polymerase (such as reverse transcriptase) or may be provided in a separate enzyme. Reverse transcriptases useful for this method may or may not have RNase H activity.

3. A second primer (labeled "5") binds to II at a complementary site to form complex III. In the case where a plurality of RNA species are being amplified simultaneously, the second primers could be random primers that bind to II at random complementary sites of a plurality of cDNA species. When it is desired to generate a library of a known mRNA family, such as for example a library of a specific immunoglobulin chain, primer 5 may comprise a sequence which is complementary to a well conserved sequence in this family.

4. Primer extension along the first cDNA strand is carried out by a DNA-dependent DNA polymerase to generate a double stranded cDNA (labeled "IV") comprising at one end a duplex of sequence B (of the first primer) and its complement. The cDNAs are substrates for amplification according to the methods of the invention.

5. The double stranded products IV are denatured (for example, by heat) to separate the two DNA strands. Various methods for strand separation could be employed for carrying out the methods of the invention. Strand V, which is of the same sense as the input (target) RNA, is a substrate for amplification, and comprises at its 5' end the sequence of the second primer (primer 5), and at its 3' end the sequence complementary to sequence B of the first primer (primer 4).

B) Linear Isothermal Amplification

1. A propromoter oligonucleotide (such as a PTO) binds to the 3' end of strand V by hybridization of its 3' end sequence B to its complementary sequence at the 3' end of V, to form complex VI.

2. A DNA-dependent DNA polymerase extends the 3' end of the sense cDNA strand (strand V) in complex VI to form the partial duplex VII, comprising a double stranded RNA polymerase promoter at one end.

3. An RNA polymerase binds to the double stranded promoter and transcribes the cDNA strand of complex VII to produce multiple copies of single stranded antisense RNA products, VIII. These antisense RNA products can also serve as substrates for exponential amplification.

One embodiment of the exponential amplification methods of the invention is illustrated in FIGS. 2A–B. In this embodiment, subsequent to the generation of antisense RNA products in the linear amplification steps, the following steps are performed.

C) Exponential Isothermal Amplification

1. Primer 5 binds to the 3' end of the RNA products VIII to form complex IX.

2. Primer extension along the RNA strand is carried out by an RNA-dependent DNA polymerase to form an RNA/DNA hybrid duplex, X.

3. RNase H degrades the RNA strand of complex X to produce single stranded DNA copies of the RNA products. A propromoter polynucleotide such as a PTO hybridizes to the 3' end of the single stranded DNA to form complex XI.

4. The 3' end of the DNA strand in complex XI is extended along the propromoter polynucleotide (PTO) to form a partial duplex XII, comprising a double stranded promoter sequence at one end. This product is the same as VII, and is a substrate for RNA polymerase for the generation of multiple copies of the RNA products, as in step b(3) above, thus producing a cyclical process for the exponential amplification of a target RNA.

Nucleic Acid Sequence Amplification Using a First Primer, a Composite Primer, Denaturation and Strand Displacement The invention provides methods of amplifying an RNA sequence of interest by using a first primer and a composite primer, denaturation, and strand displacement. Amplification can be achieved isothermally, though every step is not necessarily conducted at the same temperature. Amplified products are single stranded DNA comprising sequences complementary to the RNA sequence of interest in the target RNA.

Figure 3A:
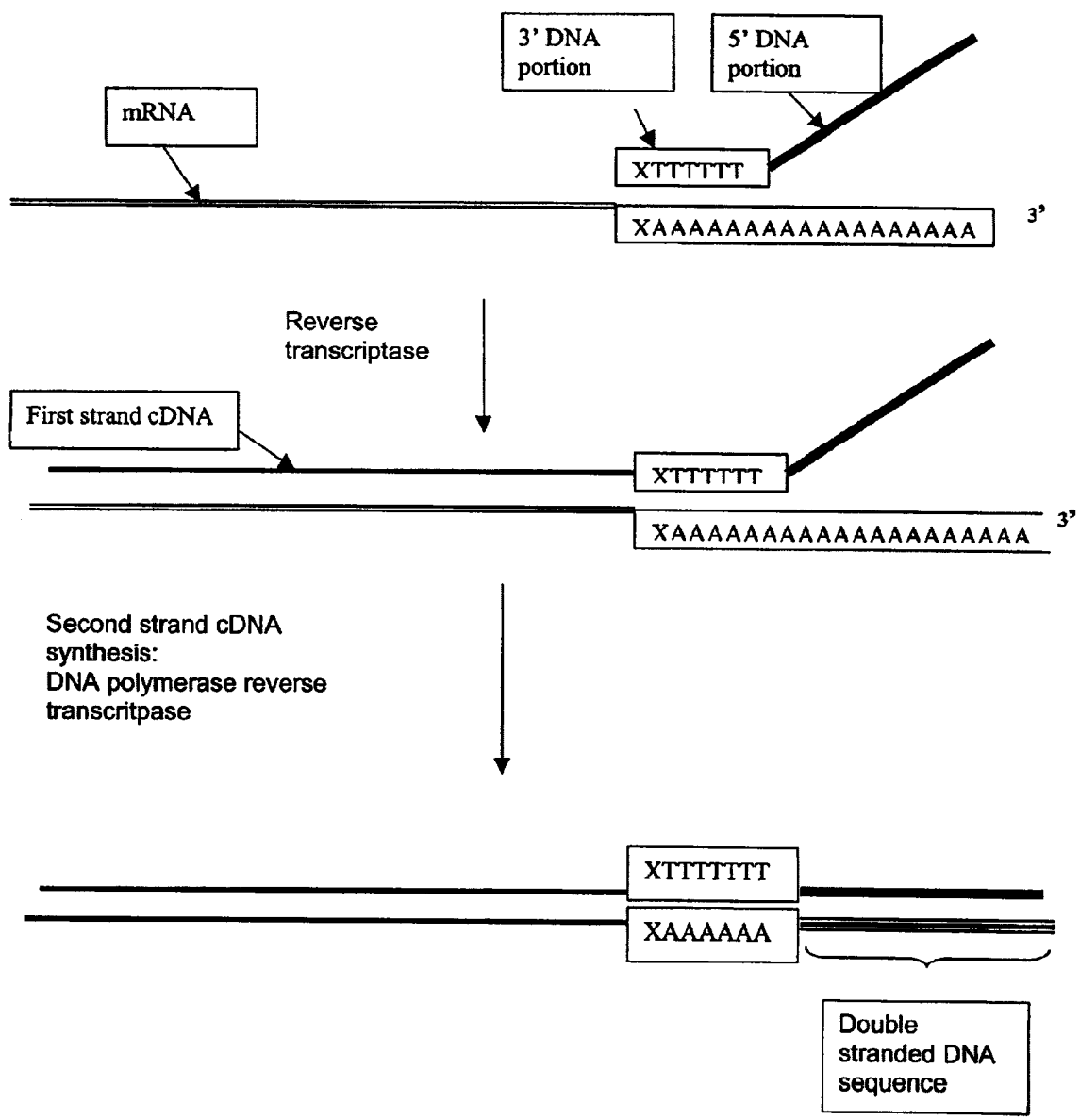

A schematic description of one embodiment of the composite primer, second primer and strand displacement-based methods of the invention is given in FIGS. 3A and B. The methods involve the following steps: (a) formation of a second strand cDNA which is the same sense as the input RNA (as described herein, and one embodiment of which is illustrated in FIG. 1); and (b) linear amplification of the complement of a second strand cDNA strand by primer extension from a composite primer along the second strand cDNA and strand displacement. See Kurn, U.S. Pat. No. 6,251,639 B1.

The embodiment illustrated in FIGS. 3A and 3B employs three oligonucleotides: a first primer which can be composed of two portions, a 3' portion (labeled "A"); and a 5' portion (labeled "B"), (labeled 1), used for formation of first strand cDNA; a second primer, used for the formation of the second strand cDNA (which may be an exogenously added second primer or one or more fragments of target RNA that remains hybridized to the first strand cDNA following RNase H treatment); and a composite primer used for linear isothermal amplification. The composite primer comprises a 5' RNA portion and a DNA portion. The first and second primers used in this aspect of the invention may comprise any first and second primer described herein (including a second primer comprising one or more fragments.

The composite primer illustrated in FIG. 3A and B comprises a sequence capable of hybridizing to the second strand cDNA, and most often comprises a sequence hybridizable to the defined 3'-portion of the second strand cDNA (that is the complement of the first primer sequence). The composite primer may additionally comprise sequences not hybridizable to the second strand cDNA under conditions which the composite primer hybridizes, such that a tail is formed.

As illustrated in FIGS. 3A and B, the composite primer comprises a DNA portion at its 3' end, and an RNA portion at its 5' end. As discussed herein, it is also possible to employ a composite primer in which the 3' DNA portion is followed, in the direction of its 5', by an RNA portion, which is followed by a portion which is DNA. The length of each of these sections is generally determined for maximum efficiency of the amplification. Only the two-portion (i.e., 3'-DNA-RNA-5') composite primer is shown in FIGS. 3A and B.

As illustrated in FIGS. 3A and B, in one embodiment, the process of the amplification methods of the invention resulting in generation of DNA products comprising sequences complementary to an RNA sequence(s) of interest based on RNA is as follows:

A) Formation of a Single Stranded cDNA Substrate for Amplification Using a Composite Primer 1. A primer binds to a target RNA by hybridization of its 3' end to the target.

2. Primer extension along the RNA strand is carried out by an RNA-dependent DNA polymerase such as reverse transcriptase, to form an RNA/DNA hybrid duplex. RNase H degrades the RNA strand of the hybrid duplex to produce a first cDNA strand (labeled "I"). The RNase H activity may be supplied by the RNA-dependent DNA polymerase (such as reverse transcriptase) or may be provided in a separate enzyme. Reverse transcriptases useful for this method may or may not have RNase H activity.

3. Primer extension along the first cDNA strand is carried out by a DNA-dependent DNA polymerase (not illustrated in FIG. 3A) to generate a double stranded cDNA, forming a complex of first and second strand cDNAs (wherein the second strand cDNA comprises a 3' end portion that is the complement of the first primer sequence), as shown in FIG. 3A.
4. The complex of first and second strand cDNAs is then denatured to form single stranded first strand cDNA and second strand cDNA, as shown in FIG. 3B. The single stranded second strand cDNA is the substrate for isothermal amplification using a composite primer and strand displacement as follows.

B) Generation of Bouble Stranded cDNA Comprising an RNA/DNA Heteroduplex

1. A composite primer comprising a 5'-RNA portion and a DNA portion hybridizes to the 3'-portion of the second strand cDNA, generally to the 3'-portion of the second strand cDNA, and is extended along the second strand cDNA by a DNA polymerase to form a double stranded complex comprising an RNA/DNA hybrid portion at one end of the complex.

C) Isothermal Linear Amplification

1. An agent, such as an enzyme, which cleaves RNA from an RNA/DNA hybrid (such as RNase H) cleaves RNA sequence from the hybrid, leaving a sequence on the second strand cDNA available for binding by another composite primer.
2. Composite primer binds by hybridization of the RNA portion to the single stranded DNA end on the second strand cDNA, which is complementary to it. The 3' DNA sequence of primer is not hybridized.
3. The 3' end of bound composite primer, and the 5' end of the DNA strand immediately upstream are the same, and would compete for hybridization to the opposite strand. Without wishing to be bound by theory, the high affinity of the DNA polymerase to hybridized 3' end of a primer would be expected to push the equilibrium of the two competing structures towards hybridization of the 3' end of the new primer and displacement of the 5' end of the previous primer extension product. Primer extension along the second strand (sense) cDNA strand results in displacement of the previous second strand cDNA, and formation of a double stranded cDNA having, at one end, an RNA/DNA hybrid composed of sequence B and its complement
4. The RNA segment of the hybrid is degraded by agent, such as RNase H, which results in the formation of a single stranded 3' end to which a new composite primer can be bound by its 5' portion.
5. The process of hybridization of the 3' end sequence of the bound composite primer, by displacement of the 5'-most end of the previous primer extension product in the duplex, primer extension and displacement of the previous product continues, and results in the accumulation of multiple copies of anti-sense single stranded DNA products.

In some embodiments, subsequent to the generation of antisense RNA products in the linear amplification steps, the following steps are performed:

D) Exponential Isothermal Amplification

1. A propromoter oligonucleotide (such as a PTO) binds to the 3' end of anti-sense single stranded DNA products.
2. Primer extension along the RNA strand is carried out by an RNA-dependent DNA polymerase to form an RNA/DNA hybrid duplex. This product is the same is a substrate for RNA polymerase for the generation of multiple copies of sense RNA products. As described herein, extension of the propromoter polynucleotide may or may not be required to effect creation of a propromoter for transcription.

Components and Reaction Conditions Used in the Methods of the Invention

Template Nucleic Acid

The RNA target to be amplified includes RNAs from any source in purified or unpurified form, which can be RNA such as total RNA, tRNA, mRNA, rRNA, mitochondrial RNA, chloroplast RNA, DNA-RNA hybrids, or mixtures thereof, from any source and/or species, including human, animals, plants, and microorganisms such as bacteria, yeasts, viruses, viroids, molds, fungi, plants, and fragments thereof. RNAs can be obtained and purified using standard techniques in the art. Amplification of a DNA target would require initial transcription of the DNA target into RNA form, which can be achieved by techniques (such as expression systems) known in the art. Amplification of a DNA-RNA hybrid would require denaturation of the hybrid to obtain a ssRNA, or denaturation followed by transcription of the DNA strand to obtain an RNA. The target RNA can be only a minor fraction of a complex mixture such as a biological sample and can be obtained from various biological material by procedures well known in the art.

The target RNA can be known or unknown and may contain more than one desired specific nucleic acid sequence of interest, each of which may be the same or different from each other. Therefore, the amplification process is useful not only for producing large amounts of one specific nucleic acid sequence, but also for amplifying simultaneously more than one different specific nucleic acid sequence located on the same or different nucleic acid molecules.

The initial step of the amplification of a target RNA sequence is rendering the target single stranded. Denaturation may be carried out to remove secondary structure present in a RNA target molecule. The denaturation step may be thermal denaturation or any other method known in the art.

First Primer

The first primer is a primer that comprises a sequence (which may or may not be the whole of the primer) that is hybridizable (under a given set of conditions) to the target RNA. This sequence can be based on a specific sequence of the target, or a random sequence (in some embodiments, the first primer is a random primer). It can also be based on a general, more universal sequence known to be present in an RNA species of interest, such as the poly-A sequence found in mRNA. In some embodiments, the primer may comprise a sequence complementary to a poly-A sequence, and may further comprise a random sequence 3' to said sequence complementary to a poly-A sequence. In some embodiments, the primer comprises a sequence, preferably at the 5' end, that is not hybridizable (under a given set of conditions) to a target RNA. In addition, the sequence that is capable of hybridizing to the target RNA may comprise a sequence complementary to the poly-A tail of mRNA, and may further comprise additional random sequences (generally not complementary to a poly-A sequence) at the 3' end of the 3' portion.

Random primers are well known in the art, and include at least the following: primers hybridizable to two or more sequences in a sample; and primers comprising poly-T sequences that are hybridizable to a multiplicity of RNAs in a sample (such as all mRNA). For convenience, a single random composite primer is discussed above. However, it is understood that the term "random primer" can refer to a primer that is a member of a population of primers which are collectively designed to a desired and/or significant population of target sequences.

It is also understood that the amplification of a plurality of mRNA species in a single reaction mixture may, but not necessarily, employ a multiplicity, or a large multiplicity of primers. Thus, the invention contemplates the use of a multiplicity of different composite primers (random or non-random) when amplifying a plurality of mRNA species in a single reaction mixture.

To achieve hybridization to a target nucleic acid (which, as is well known and understood in the art, depends on other factors such as, for example, ionic strength and temperature), the sequence of the primer that is hybridizable to the target RNA is preferably of at least about 60%, more preferably at least about 75%, even more preferably at least about 90%, and most preferably at least about 95% complementarily to the target nucleic acid.

In some embodiments, the first primer comprises a 5' sequence (which generally includes the 5' most nucleotide) the complement of which is hybridizable by a propromoter polynucleotide. This sequence enables the creation of a defined end sequence for the 5' end of the first primer extension product (and thus, subsequently the 3' end of the second/third primer extension product). Having a defined end sequence is particularly advantageous with respect to hybridization of a propromoter polynucleotide to the 3' end of the second and third primer extension products in subsequent steps. Thus, in these embodiments, the first primer comprises a sequence that when introduced into the amplification steps of the methods of the invention results in generation of an intermediate polynucleotide to which a propromoter polynucleotide can hybridize. In some of these embodiments, the 5' sequence the complement of which is hybridizable by a propromoter polynucleotide is hybridizable (under a given set of conditions) to a target RNA when the primer is hybridized to the target RNA. In other embodiments, the 5' sequence the complement of which is hybridizable by a propomoter polynucleotide is not hybridizable (under a given set of conditions) to a target RNA when the primer is hybridized to the target RNA (thus constituting a tail when the 3' sequence of the primer is hybridized to the target).

In one embodiment, the first primer comprises DNA. In another embodiment, the first primer comprises RNA. In yet another embodiment, the first primer comprises DNA and RNA.

Second Primer

The second primer in the methods of the invention comprises a sequence (which may or may not be the whole of the primer) that is hybridizable (under a given set of conditions) to a first primer extension product at a site on the first primer extension product such that the second primer extension product would include the RNA sequence of interest. In some embodiments, the hybridizable sequence of the second primer is designed based on a known sequence of the desired binding site on a first primer extension product. In other embodiments, the hybridizable sequence is based on random sequences known in the art to be suitable for random priming of a plurality of RNA species. In some embodiments, a second primer comprises a sequence, preferably at the 5' end, that is not hybridizable (under a given set of conditions) to a first primer extension product. In other embodiments, the second primer comprises a strand switch oligonucleotide, described in U.S. Pat. Nos. 5,962,271 and 5,962,272, which is hybridizable to the Cap sequences present on mRNA and causes the reverse transcriptase to switch from the mRNA template to the switch oligonucleotide, permitting generation of a second strand cDNA primed by the "switch oligonucleotide". Alternatively, a homopolymeric tail is added to the 3' terminus of the first primer extension product, and the second primer comprises the complement of the homopolymeric tail.

In one embodiment, the second primer comprises DNA. In another embodiment, the second primer consists of DNA. In another embodiment, the second primer comprises RNA. In yet another embodiment, the second primer comprises DNA and RNA.

In some embodiments, the second primer is provided by self priming (for example, by a hairpin loop) at the 3' end of the first primer extension product. In these embodiments, a sequence at the 3' end of the first primer extension product hybridizes to another sequence in the first primer extension product, for example as described in U.S. Pat. No. 6,132, 997. In these embodiments, said sequence at the 3' of the first primer extension product is generally cleaved (for example, with an S1 nuclease) following its hybridization to the first primer extension product and/or its extension along the first primer extension product. See U.S. Pat. No. 6,132,997.

In some embodiments, the second primer is provided by a target RNA fragment. Such a target RNA fragment can be generated as a result of incomplete degradation of a target RNA in a complex of target RNA and first primer extension product by an enzyme that cleaves RNA in an RNA/DNA hybrid, such that one or more RNA fragments remain bound to the first primer extension product.

To achieve hybridization to a first primer extension product (which, as is well known and understood in the art, depends on other factors such as, for example, ionic strength and temperature), the sequence of the second primer that is hybridizable to the first primer extension product is preferably of at least about 60%, more preferably at least about 75%, even more preferably at least about 90%, and most preferably at least about 95% complementarity to the first primer extension product.

Third Primer

The third primer in the methods of the invention comprises a sequence (which may or may not be the whole of the primer) that is hybridizable (under a given set of conditions) to the RNA transcript generated from the second primer extension product (as the template) at a site on the RNA transcript such that the third primer extension product would include the RNA sequence of interest, if present. In some embodiments, the hybridizable sequence of the third primer is designed based on a known sequence of the desired binding site on an RNA transcript. In other embodiments, the hybridizable sequence is based on random sequences known in the art to be suitable for random priming of a plurality of RNA species. In some embodiments, the third primer comprises a sequence, preferably at the 5' end, that is not hybridizable (under a given set of conditions) to an RNA transcript.

To achieve hybridization to an RNA transcript (which, as is well known and understood in the art, depends on other factors such as, for example, ionic strength and temperature), the sequence of the third primer that is hybridizable to the RNA transcript is preferably of at least about 60%, more preferably at least about 75%, even more preferably at least about 90%, and most preferably at least about 95% complementarity to the RNA transcript.

In one embodiment, the third primer comprises DNA. In another embodiment, the third primer comprises RNA. In yet another embodiment, the third primer comprises DNA and RNA.

In some embodiments, the third primer is provided by self priming (for example, by a hairpin loop) at the 3' end of an RNA transcript. In these embodiments, a sequence at the 3' end of the RNA transcript hybridizes to another sequence in the RNA transcript itself. In these embodiments, said sequence at the 3' of the RNA transcript is generally cleaved following its hybridization to the RNA transcript and/or its extension along the RNA transcript.

Composite Primer

In some embodiments, the methods of the invention employ a composite primer that is composed of RNA and DNA portions. The composite primer is designed such that subsequent displacement of the primer extension product by binding of a new (additional) composite primer and the extension of the new primer by the polymerase can be achieved. In addition, cleavage of the RNA portion of the primer extension product leads to generation of amplification product which is not a substrate for amplification by the composite primer.

The composite primer illustrated in FIG. 3 comprises sequences capable of hybridizing to the second strand cDNA, and most often comprises sequences hybridizable to the defined 3'-portion of the second strand cDNA (that is the complement of the first primer sequence). The composite primer may comprise all or a portion of the sequence of the first primer. The composite primer may additionally comprise sequences not hybridizable to the second strand cDNA such that a tail is formed.

It is also understood that the amplification of a plurality of mRNA species in a single reaction mixture may, but not necessarily, employ a multiplicity, or a large multiplicity of primers. Thus, the invention contemplates the use of a multiplicity of different composite primers (random or non-random) when amplifying a plurality of mRNA species in a single reaction mixture.

A composite primer comprises at least one RNA portion that is capable of (a) binding (hybridizing) to a sequence on the second strand cDNA product independent of hybridization of the DNA portion(s) to a sequence on the same extension product; and (b) being cleaved with a ribonuclease when hybridized to the second strand cDNA. The composite primers bind to the second strand cDNA to form a partial heteroduplex in which only the RNA portion of the primer is cleaved upon contact with a ribonuclease such as RNase H, while the second strand cDNA remains intact, thus enabling annealing of another composite primer.

The composite primers also comprise a 3' DNA portion that is capable of hybridization to a sequence on the second strand cDNA such that its hybridization to the cDNA is favored over that of the nucleic acid strand that is displaced from the second strand cDNA by the DNA polymerase. Such primers can be rationally designed based on well known factors that influence nucleic acid binding affinity, such as sequence length and/or identity, as well as hybridization conditions. In a preferred embodiment, hybridization of the 3' DNA portion of the composite primer to its complementary sequence in the second strand cDNA is favored over the hybridization of the homologous sequence in the 5' end of the displaced strand to the second strand cDNA.

Generation of primers suitable for extension by polymerization is well known in the art, such as described in PCT Pub. No. WO 99/42618 (and references cited therein). The composite primer comprises a combination of RNA and DNA (see definition above), with the 3'-end nucleotide being a nucleotide suitable for nucleic acid extension. The 3'-end nucleotide can be any nucleotide or analog that when present in a primer, is extendable by a DNA polymerase. Generally, the 3'-end nucleotide has a 3'-OH. Suitable primers include those that comprise at least one portion of RNA and at least one portion of DNA. For example, composite primers can comprise a 5'-RNA portion and a 3'-DNA portion (in which the RNA portion is adjacent to the 3'-DNA portion); or 5'- and 3'-DNA portions with an intervening RNA portion. Accordingly, in one embodiment, the composite primer comprises a 5' RNA portion and a 3'-DNA portion, preferably wherein the RNA portion is adjacent to the 3'-DNA portion. In another embodiment, the composite primer comprises 5' and 3'-DNA portions with at least one intervening RNA portion (i.e., an RNA portion between the two DNA portions). In yet another embodiment, the composite primer of the invention comprises a 3'-DNA portion and at least one intervening RNA portion (i.e., an RNA portion between DNA portions).

The length of an RNA portion in a composite primer comprising a 3'-DNA portion and an RNA portion can be preferably from about 1 to about 50, more preferably from about 3 to about 20, even more preferably from about 4 to about 15, and most preferably from about 5 to about 10 nucleotides. In some embodiments of a composite primer comprising a 3'-DNA portion and an RNA portion, an RNA portion can be at least about any of 1, 3, 4, 5 nucleotides, with an upper limit of about any of 10, 15, 20, 25, 3, 50 nucleotides.

The length of the 5'-RNA portion in a composite primer comprising a 5'-RNA portion and a 3'-DNA portion can be preferably from about 3 to about 50 nucleotides, more preferably from about 5 to about 20 nucleotides, even more preferably from about 7 to about 18 nucleotides, preferably from about 8 to about 17 nucleotides, and most preferably from about 10 to about 15 nucleotides. In other embodiments of a composite primer comprising a 5'-RNA portion and a 3'-DNA portion, the 5'-RNA portion can be at least about any of 3, 5, 7, 8, 10 nucleotides, with an upper limit of about any of 15, 17, 18, 20, 50 nucleotides.

In embodiments of a composite primer comprising a 5'-RNA portion and a 3'-DNA portion further comprising non-5'-RNA portion(s), a non-5'-RNA portion can be preferably from about 1 to about 7 nucleotides, more preferably from about 2 to about 6 nucleotides, and most preferably from about 3 to about 5 nucleotides. In certain embodiments of a composite primer comprising a 5'-RNA portion and a 3'-DNA portion further comprising non-5'-RNA portion(s), a non-5'-RNA portion can be at least about any of 1, 2, 3, 5, with an upper limit of about any of 5, 6, 7, 10 nucleotides.

In embodiments of a composite primer comprising a 5'-RNA portion and a 3'-DNA portion, in which the 5'-RNA portion is adjacent to the 3'-DNA portion, the length of the 5'-RNA portion can be preferably from about 3 to about 50 nucleotides, more preferably from about 5 to about 20 nucleotides, even more preferably from about 7 to about 18 nucleotides, preferably from about 8 to about 17 nucleotides, and most preferably from about 10 to about 15 nucleotides. In certain embodiments of a composite primer comprising a 5'-RNA portion and a 3'-DNA portion, in which the 5'-RNA portion is adjacent to the 3'-DNA portion, the 5'-RNA portion can be at least about any of 3, 5, 7, 8, 10 nucleotides, with an upper limit of about any of 15, 17, 18, 20, 50 nucleotides.

The length of an intervening RNA portion in a composite primer comprising 5'- and 3'-DNA portions with at least one intervening RNA portion can be preferably from about 1 to about 7 nucleotides, more preferably from about 2 to about 6 nucleotides, and most preferably from about 3 to about 5 nucleotides. In some embodiments of a composite primer comprising 5'- and 3'-DNA portions with at least one intervening RNA portion, an intervening RNA portion can be at least about any of 1, 2, 3, 5 nucleotides, with an upper limit of about any of 5, 6, 7, 10 nucleotides. The length of an intervening RNA portion in a composite primer comprising a 3'-DNA portion and at least one intervening RNA portion can be preferably from about 1 to about 7 nucleotides, more preferably from about 2 to about 6 nucleotides, and most preferably from about 3 to about 5 nucleotides. In some embodiments of a composite primer comprising a 3'-DNA portion and at least one intervening RNA portion, an intervening RNA portion can be at least about any of 1, 2, 3, 5 nucleotides, with an upper limit of about any of 5, 6, 7, 10 nucleotides. In a composite primer comprising a 3'-DNA portion and at least one intervening RNA portion, further comprising a 5'-RNA portion, the 5'-RNA portion can be preferably from about 3 to about 25 nucleotides, more preferably from about 5 to about 20 nucleotides, even more preferably from about 7 to about 18 nucleotides, preferably from about 8 to about 17 nucleotides, and most preferably from about 10 to about 15 nucleotides. In some embodiments of a composite primer comprising a 3'-DNA portion and at least one intervening RNA portion, further comprising a 5'-RNA portion, the 5'-RNA portion can be at least about any of 3, 5, 7, 8, 10 nucleotides, with an upper limit of about any of 15, 17, 18, 20 nucleotides.

The length of the 3'-DNA portion in a composite primer comprising a 3'-DNA portion and an RNA portion can be preferably from about 1 to about 20, more preferably from about 3 to about 18, even more preferably from about 5 to about 15, and most preferably from about 7 to about 12 nucleotides. In some embodiments of a composite primer comprising a 3'-DNA portion and an RNA portion, the 3'-DNA portion can be at least about any of 1, 3, 5, 7, 10 nucleotides, with an upper limit of about any of 10, 12, 15, 18, 20, 22 nucleotides.

The length of the 3'-DNA portion in a composite primer comprising a 5'-RNA portion and a 3'-DNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 5'-RNA portion and a 3'-DNA portion, the 3' DNA portion can be at least about any of 1, 3, 5, 7, 10 nucleotides, with an upper limit of about any of 10, 12, 15, 18, 20, 22 nucleotides.

In embodiments of a composite primer comprising a 5'-RNA portion and a 3'-DNA portion, further comprising non-3'-DNA portion(s), a non-3'-DNA portion can be preferably from about 1 to about 10 nucleotides, more preferably from about 2 to about 8 nucleotides, and most preferably from about 3 to about 6 nucleotides. In some embodiments of a composite primer comprising a 5'-RNA portion and a 3'-DNA portion, further comprising non-3'-DNA portion(s), a non-3'-DNA portion can be at least about any of 1, 2, 3, 5 nucleotides, with an upper limit of about any of 6, 8, 10, 12 nucleotides.

In embodiments of a composite primer comprising a 5'-RNA portion and a 3'-DNA portion in which the 5'-RNA portion is adjacent to the 3'-DNA portion, the length of the 3'-DNA portion can be preferably from about 1 to about 20 nucleotides, more preferably from about 3 to about 18 nucleotides, even more preferably from about 5 to about 15 nucleotides, and most preferably from about 7 to about 12 nucleotides. In certain embodiments of the primer comprising a 5'-RNA portion and a 3'-DNA portion in which the 5'-RNA portion is adjacent to the 3'-DNA portion, the 3'-DNA portion can be at least about any of 1, 3, 5, 7, 10 nucleotides, with an upper limit of about any of 10, 12, 15, 18, 20, 22 nucleotides.

The length of a non-3'-DNA portion in a composite primer comprising 5'- and 3'-DNA portions with at least one intervening RNA portion can be preferably from about 1 to about 10 nucleotides, more preferably from about 2 to about 8 nucleotides, and most preferably from about 3 to about 6 nucleotides. In some embodiments of a primer comprising 5'- and 3'-DNA portions with at least one intervening RNA portion, a non-3'-DNA portion can be at least about any of 1, 2, 3, 5 nucleotides, with an upper limit of about any of 6, 8, 10, 12 nucleotides.

The length of the 3'-DNA portion in a composite primer comprising 5'- and 3'-DNA portions with at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising 5'- and 3'-DNA portions with at least one intervening RNA portion, the 3'-DNA portion can be at least about any of 1, 3, 5, 7, 10 nucleotides, with an upper limit of about any of 10, 12, 15, 18, 20, 22 nucleotides.

The length of a non-3'-DNA portion (i.e., any DNA portion other than the 3'-DNA portion) in a composite primer comprising a 3'-DNA portion and at least one intervening RNA portion can be preferably from about 1 to about 10 nucleotides, more preferably from about 2 to about 8 nucleotides, and most preferably from about 3 to about 6 nucleotides. In some embodiments of a composite primer comprising a 3'-DNA portion and at least one intervening RNA portion, a non-3'-DNA portion can be at least about any of 1, 3, 5, 7, 10 nucleotides, with an upper limit of about any of 6, 8, 10, 12 nucleotides. The length of the 3'-DNA portion in a composite primer comprising a 3'-DNA portion and at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 3'-DNA portion and at least one intervening RNA portion, the 3'-DNA portion can be at least about any of 1, 3, 5, 7, 10 nucleotides, with an upper limit of about any of 10, 12, 15, 18, 20, 22 nucleotides. It is understood that the lengths for the various portions can be greater or less, as appropriate under the reaction conditions of the methods of this invention.

In some embodiments, the 5'-DNA portion of a composite primer includes the 5'-most nucleotide of the primer. In some embodiments, the 5'-RNA portion of a composite primer includes the 5' most nucleotide of the primer. In other embodiments, the 3'-DNA portion of a composite primer includes the 3' most nucleotide of the primer. In other embodiments, the 3'-DNA portion is adjacent to the 5'-RNA portion and includes the 3' most nucleotide of the primer (and the 5'-RNA portion includes the 5' most nucleotide of the primer).

The total length of the composite primer can be preferably from about 10 to about 50 nucleotides, more preferably from about 15 to about 30 nucleotides, and most preferably from about 20 to about 25 nucleotides. In some embodiments, the length can be at least about any of 10, 15, 20, 25 nucleotides, with an upper limit of about any of 25, 30, 50, 60 nucleotides. It is understood that the length can be greater or less, as appropriate under the reaction conditions of the methods of this invention.

To achieve hybridization to a target nucleic acid (which, as is well known and understood in the art, depends on other factors such as, for example, ionic strength and temperature), the portion of the primer that is hybridizable to the target RNA is preferably of at least about 60%, more preferably at least about 75%, even more preferably at least about 90%, and most preferably at least about 95% complementarity to the target nucleic acid.

Polynucleotide Comprising a Propromoter and a Region Which Hybridizes to a Primer Extension Product The methods of the invention employ a propromoter polynucleotide comprising a propromoter and a region which hybridizes to a primer extension product. In some embodiments, the propromoter polynucleotide is provided as a PTO, as described in greater detail below.

Propromoter Template Oligonucleotide

In some embodiments, the methods employ a promoter sequence for transcription which is provided by a propromoter template oligonucleotide (PTO).

A PTO for use in the methods and compositions of the invention is a single-stranded polynucleotide, generally DNA, comprising a propromoter sequence that is designed for formation of a double stranded promoter of an RNA polymerase, and a portion capable of hybridizing to the 3' end of a primer extension product. In a preferred embodiment, the propromoter sequence is located in the 5' portion of the oligonucleotide and the hybridizing sequence is located in the 3' portion of the oligonucleotide. In one embodiment, and most typically, the promoter and hybridizing sequences are different sequences. In another embodiment, the promoter and hybridizing sequences overlap in sequence identity. In yet another embodiment, the promoter and hybridizing sequences are the same sequence, and thus are in the same location on the PTO. In the embodiments wherein hybridization of the PTO to the primer extension product results in a duplex comprising an overhang (the 5' end of the PTO that does not hybridize to the primer extension product, typically comprising all or part of the propromoter sequence), DNA polymerase fills in the overhang to create a double stranded promoter capable of effecting transcription by a suitable RNA polymerase.

Promoter sequences that allow transcription of a template DNA are known in the art and have been discussed above. Preferably, the promoter sequence is selected to provide optimal transcriptional activity of the particular RNA polymerase used. Criteria for such selection, i.e., a particular promoter sequence particularly favored by a particular RNA polymerase, is also known in the art. For example, the sequences of the promoters for transcription by T7 DNA dependent RNA polymerase and SP6 are known in the art. The promoter sequence can be from a prokaryotic or eukaryotic source.

In some embodiments, the PTO comprises an intervening sequence between a propromoter sequence and a portion capable of hybridizing to the 3' end of the primer extension product. Suitable length of the intervening sequence can be empirically determined, and can be at least about 1, 2, 4, 6, 8, 10, 12, 15 nucleotides. Suitable sequence identity of the intervening sequence can also be empirically determined, and the sequence is designed to preferably, but not necessarily, enhance degree of amplification as compared to omission of the sequence. In one embodiment, the intervening sequence is a sequence that is designed to provide for enhanced, or more optimal, transcription by the RNA polymerase used. Generally, the sequence is not related (i.e., it does not substantially hybridize) to a primer extension product. More optimal transcription occurs when transcriptional activity of the polymerase from a promoter that is operatively linked to said sequence is greater than from a promoter that is not so linked. The sequence requirements for optimal transcription are generally known in the art as previously described for various DNA dependent RNA polymerases, such as in U.S. Pat. Nos. 5,766,849 and 5,654,142, and can also be empirically determined.

In another embodiment, the PTO comprises a sequence that is 5' to the propromoter sequence, i.e., the PTO comprises additional nucleotides (which may or may not be transcriptional regulatory sequences) located 5' to the propromoter sequence. Generally, but not necessarily, the sequence is not hybridizable (under a given set of conditions) to the primer extension product.

In one embodiment, the PTO cannot function efficiently as a primer for nucleic acid extension. Techniques for blocking the primer function of the PTO include any that prevent addition of nucleotides to the 3' end of the PTO by a DNA polymerase. Such techniques are known in the art, including, for example, substitution or modification of the 3' hydroxyl group, or incorporation of a modified nucleotide, such as a dideoxynucleotide, in the 3'-most position of the PTO that is not capable of anchoring addition of nucleotides by a DNA polymerase. It is possible to block the 3' end using a label, or a small molecule which is a member of a specific binding pair, such as biotin. It is also possible to render the 3' end non-extendable by addition of nucleotides which cannot hybridize to a primer extension product, either due to non-complementarity or due to structural modifications which do not support hydrogen bonding. In other embodiments, the PTO is not blocked.

The length of the portion of the PTO that hybridizes to a primer extension product of interest is preferably from about 5 to about 50 nucleotides, more preferably from about 10 to about 40 nucleotides, even more preferably from about 15 to about 35 nucleotides, and most preferably from about 20 to 30 nucleotides. In some embodiments, the hybridizing portion is at least about any of the following: 3, 5, 10, 15, 20; and less than about any of the following: 30, 40, 50, 60. The complementarity of the hybridizing portion is preferably at least about 25%, more preferably at least about 50%, even more preferably at least about 75%, and most preferably at least about 90%, to its intended binding sequence on the primer extension product of interest.

DNA Polymerase, Ribonuclease and RNA Polymerase

The amplification methods of the invention employ the following enzymes: an RNA-dependent DNA polymerase, a DNA-dependent DNA polymerase, a ribonuclease such as RNase H, and a DNA-dependent RNA polymerase. One or more of these activities may be found and used in a single enzyme. For example, RNase H activity may be supplied by an RNA-dependent DNA polymerase (such as reverse transcriptase) or may be provided in a separate enzyme. Reverse transcriptases useful for this method may or may not have RNase H activity.

One aspect of the invention is the formation of double stranded cDNA from a primer-RNA complex. This process generally utilizes the enzymatic activities of an RNA-dependent DNA polymerase, a DNA-dependent DNA polymerase and a ribonuclease activity.

RNA-dependent DNA polymerases for use in the methods and compositions of the invention are capable of effecting extension of a primer according to the methods of the invention. Accordingly, a preferred RNA-dependent RNA polymerase is one that is capable of extending a nucleic acid primer along a nucleic acid template that is comprised at least predominantly of ribonucleotides. Suitable RNA-dependent DNA polymerases for use in the methods and compositions of the invention include reverse transcriptase. Many reverse transcriptases, such as those from avian myeoloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a reverse transcriptase which lacks the RNase H activity. Reverse transcriptase devoid of RNase H activity are known in the art, including those comprising a mutation of the wild type reverse transcriptase where the mutation eliminates the RNase H activity. In these cases, the addition of an RNase H from other sources, such as that isolated from E. coli, can be employed for the formation of the double stranded cDNA.

DNA-dependent DNA polymerases for use in the methods and compositions of the invention are capable of effecting extension of a primer according to the methods of the invention. Accordingly, a preferred polymerase is one that is capable of extending a nucleic acid primer along a nucleic acid template that is comprised at least predominantly of deoxynucleotides. The formation of the double stranded cDNA can be carried out by reverse transcriptase which comprises both RNA-dependent DNA polymerase and DNA-dependent DNA polymerase activities. Preferably, the DNA polymerase has high affinity for binding at the 3'-end of an oligonucleotide hybridized to a nucleic acid strand. Preferably, the DNA polymerase does not possess substantial nicking activity. Preferably, the polymerase has little or no 5'->3' exonuclease activity so as to minimize degradation of primer, or primer extension polynucleotides. Generally, this exonuclease activity is dependent on factors such as pH, salt concentration, whether the template is double stranded or single stranded, and so forth, all of which are familiar to one skilled in the art. Mutant DNA polymerases in which the 5'->3' exonuclease activity has been deleted, are known in the art and are suitable for the amplification methods described herein. Preferably, the DNA polymerase has little to no proofreading activity.

Suitable DNA polymerases for use in the methods and compositions of the invention include those disclosed in U.S. Pat. Nos. 5,648,211 and 5,744,312, which include exo⁻ Vent (New England Biolabs), exo⁻ Deep Vent (New England Biolabs), Bst (BioRad), exo⁻ Pfu (Stratagene), Bca (Panvera), sequencing grade Taq (Promega), and thermostable DNA polymerases from thermoanaerobacter thermohydrosulfuiricus.

An agent that cleaves RNA in an RNA/DNA hybrid (e.g. ribonuclease) is used in the methods and compositions of the invention. Preferably, the agent, which can be ribonuclease, cleaves ribonucleotides regardless of the identity and type of nucleotides adjacent to the ribonucleotide to be cleaved. It is preferred that the agent (e.g. ribonuclease) cleaves independent of sequence identity. Examples of suitable ribonucleases for the methods and compositions of the invention are well known in the art, including ribonuclease H (RNase H), including Hybridase.

The DNA-dependent RNA polymerase for use in the methods and compositions of the invention are known in the art. Either eukaryotic or prokaryotic polymerases may be used. Examples include T7, T3 and SP6 RNA polymerases. Generally, the RNA polymerase selected is capable of transcribing from the promoter sequence provided by the propromoter polynucleotides as described herein. Generally, the RNA polymerase is a DNA-dependent polymerase, which is preferably capable of transcribing from a single stranded DNA template so long as the promoter region is double stranded.

In general, the enzymes used included in the methods and compositions of the invention should not produce substantial degradation of the nucleic acid components of said methods and compositions.

Reaction Conditions and Detection

Appropriate reaction media and conditions for carrying out the methods of the invention are those that permit nucleic acid amplification according to the methods of the invention. Such media and conditions are known to persons of skill in the art, and are described in various publications, such as U.S. Pat. Nos. 5,554,516; 5,716,785; 5,130,238; 5,194,370; 6,090,591; 5,409,818; 5,554,517; 5,169,766; 5,480,784; 5,399,491; 5,679,512; and PCT Pub. No. WO99/42618. For example, a buffer may be Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as $Mg^{2+}$ or $Mn^{2+}$, at a final concentration of free ions that is within the range of from about 0.01 to about 15 mM, and most preferably from about 1 to 10 mM. The reaction medium can also include other salts, such as KCl or NaCl, that contribute to the total ionic strength of the medium. For example, the range of a salt such as KCl is preferably from about 0 to about 125 mM, more preferably from about 0 to about 100 mM, and most preferably from about 0 to about 75 mM. The reaction medium can further include additives that could affect performance of the amplification reactions, but that are not integral to the activity of the enzyme components of the methods. Such additives include proteins such as BSA, single stranded binding protein (for example, T4 gene 32 protein), and non-ionic detergents such as NP40 or Triton. Reagents, such as DTT, that are capable of maintaining enzyme activities can also be included. Such reagents are known in the art. Where appropriate, an RNase inhibitor (such as Rnasin) that does not inhibit the activity of the RNase employed in the method can also be included. Any aspect of the methods of the invention can occur at the same or varying temperatures. Preferably, the amplification reactions (particularly, primer extension and transcription; and generally not the step of denaturing the complex of first and second primer extension products) are performed isothermally, which substantially avoids the cumbersome thermocycling process. The amplification reaction is carried out at a temperature that permits hybridization of the oligonucleotides (primer, and/or PTO) of the invention to the template polynucleotide and that does not substantially inhibit the activity of the enzymes employed. The temperature can be in the range of preferably about 25° C. to about 85° C., more preferably about 30° C. to about 80° C., and most preferably about 37° C. to about 75° C. The temperature for the transcription steps can be lower than the temperature(s) for the preceding steps. The temperature of the transcription steps can be in the range of preferably about 25° C. to about 85° C., more preferably about 30° C. to about 75° C., and most preferably about 37° C. to about 70° C.

Nucleotide and/or nucleotide analogs, such as deoxyribonucleoside triphosphates, that can be employed for synthesis of the primer extension products in the methods of the invention are provided in the amount of from preferably about 50 to about 2500 µM, more preferably about 100 to about 2000 µM, even more preferably about 200 to about 1700 µM, and most preferably about 250 to about 1500 µM.

Nucleotides and/or analogs, such as ribonucleoside triphosphates, that can be employed for synthesis of the RNA transcripts in the methods of the invention are provided in the amount of from preferably about 0.25 to about 6 mM, more preferably about 0.5 to about 5 mM, even more preferably about 0.75 to about 4 mM, and most preferably about 1 to about 3 mM.

The oligonucleotide components of the amplification reactions of the invention are generally in excess of the number of target nucleic acid sequence to be amplified. They can be provided at about or at least about any of the following: 10, $10^2$, $10^4$, $10^6$, $10^8$, $10^{10}$, $10^{12}$ times the amount of target nucleic acid. Primers and PTO can each be provided at about or at least about any of the following concentrations: 50 nM, 100 nM, 500 nM, 1000 nM, 2500 nM, 5000 nM.

In one embodiment, the foregoing components are added simultaneously at the initiation of the amplification process. In another embodiment, components are added in any order prior to or after appropriate timepoints during the amplification process, as required and/or permitted by the amplification reaction. Such timepoints, some of which are noted below, can be readily identified by a person of skill in the art. The enzymes used for nucleic acid amplification according to the methods of the invention can be added to the reaction mixture either prior to the target nucleic acid denaturation step, following the denaturation step, or following hybridization of the primer to the target RNA, as determined by their thermal stability and/or other considerations known to the person of skill in the art. The first strand cDNA (first primer extension product) and the second strand cDNA (second primer extension product) synthesis reactions can be performed consecutively, followed by the amplification steps (for example, binding of propromoter polynucleotide and transcription). In these embodiments, the reaction conditions and components may be varied between the different reactions.

The amplification reactions can be stopped at various timepoints, and resumed at a later time. Said timepoints can be readily identified by a person of skill in the art. One timepoint is at the end of first strand cDNA synthesis. Another timepoint is at the end of second strand cDNA synthesis. Methods for stopping the reactions are known in the art, including, for example, cooling the reaction mixture to a temperature that inhibits enzyme activity or heating the reaction mixture to a temperature that destroys an enzyme. Methods for resuming the reactions are also known in the art, including, for example, raising the temperature of the reaction mixture to a temperature that permits enzyme activity or replenishing a destroyed (depleted) enzyme. In some embodiments, one or more of the components of the reactions is replenished prior to, at, or following the resumption of the reactions. Alternatively, the reaction can be allowed to proceed (i.e., from start to finish) without interruption.

The reaction can be allowed to proceed without purification of intermediate complexes, for example, to remove primer. Products can be purified at various timepoints, which can be readily identified by a person of skill in the art. One timepoint is at the end of first strand cDNA synthesis. Another timepoint is at the end of second strand cDNA synthesis.

The detection of the amplification product is indicative of the presence of the target sequence. Quantitative analysis is also feasible. Direct and indirect detection methods (including quantitation) are well known in the art. For example, by comparing the amount of product amplified from a test sample containing an unknown amount of a polynucleotide containing a target sequence to the product of amplification of a reference sample that has a known quantity of a polynucleotide that contains the target sequence, the amount of target sequence in the test sample can be determined. The amplification methods of the invention can also be extended to analysis of sequence alterations and sequencing of the target nucleic acid. Further, detection could be effected by, for example, examination of translation products from RNA amplification products.

Compositions and Kits of the Invention

The invention also provides compositions and kits used in the methods described herein. The compositions may be any component(s), reaction mixture and/or intermediate described herein, as well as any combination thereof.

For example, the invention provides compositions comprising: (a) a first primer; (b) a second primer (which can be a random primer); and (c) a propromoter polynucleotide (such as a PTO). In some embodiments, the compositions further comprises: (d) a third primer (which can be a random primer). In some embodiments, the second primer and/or third primer is a random primer. In some embodiments, the propromoter polynucleotide ((c), above) is capable of hybridizing to the complement of the 5' portion of the first primer.

The invention also provides compositions comprising a propromoter polynucleotide (such as a PTO) capable of hybridizing to a 3' portion of a second primer extension that is complement of a 5' portion of a first primer used to create first primer extension product.

The invention also provides compositions comprising (a) a first primer; (b) a second primer (which can be a random primer); and (c) a composite primer, wherein the composite primer comprises a 5' RNA portion and a DNA portion. In some embodiments, the composition further comprises one or more of the following: DNA-dependent DNA polymerase, RNA-dependent DNA polymerase, and an agent (generally an enzyme) that cleaves RNA from an RNA/DNA heteroduplex.

The invention also provides compositions comprising a propromoter polynucleotide, wherein the propromoter is hybridizable to a sequence in the second primer extension product comprising the complement of the 5' portion of a first prime, wherein the first primer is extended to form the first primer extension product.

In another aspect, the invention provides complexes and/or reaction intermediates produced (present) in any of the methods described herein. Examples of such complexes are schematically depicted in FIGS. 1,2 and 3. In one example, a complex of the invention is a complex comprising: (a) a second or third primer extension product; and (b) a propromoter polynucleotide (for example, a PTO). In yet another example, the invention provides compositions comprising a complex of (a) a third primer extension product; and (b) a propromoter polynucleotide (which can be a PTO). In yet another example, the invention provides compositions comprising a complex of (a) a second primer extension product, generated by denaturation of a hybridized first and second primer extension product; and (b) a composite primer hybridizable to the second primer extension product.

The invention also provides compositions comprising the amplification products described herein. Accordingly, the invention provides a population of anti-sense RNA molecules which are copies of a target sequence, which are produced by any of the methods described herein. The invention also provides a population of anti-sense polynucleotides (generally DNA) molecules, which are produced by any of the methods described herein.

The compositions are generally in a suitable medium, although they can be in lyophilized form. Suitable media include, but are not limited to, aqueous media (such as pure water or buffers).

The invention provides kits for carrying out the methods of the invention. Accordingly, a variety of kits are provided in suitable packaging. The kits may be used for any one or more of the uses described herein, and, accordingly, may contain instructions for any one or more of the following uses: amplifying a RNA sequence of interest, sequencing, genotyping (nucleic acid mutation detection), preparation of an immobilized nucleic acid (which can be a nucleic acid immobilized on a microarray), characterizing nucleic acids using the amplified nucleic acid products generated by the methods of the invention; gene expression profiling, subtractive hybridization; preparation of probes for subtractive hybridization; and preparing libraries (which can be cDNA and/or differential hybridization libraries).

The kits of the invention comprise one or more containers comprising any combination of the components described herein, and the following are examples of such kits. For example, the invention provides kits that comprise a first primer that comprises a sequence that when introduced into the amplification steps of the methods of the invention results in generation of an intermediate polynucleotide to which a propromoter polynucleotide can hybridize. The invention also provides kits that further comprise a second primer and/or a third primer, either of both of which can be a random primer. The kits can contain further components, such as any of (a) a propromoter polynucleotide (such as a PTO); and (b) any of the enzymes described herein, such as an enzyme which cleaves RNA from an RNA/DNA hybrid (for example, RNaseH), a DNA polymerase (RNA-dependent or DNA-dependent) or an RNA polymerase. With respect to compositions containing a random primer, these compositions may also contain a plurality of random primers (i.e., a population of random primers having different sequences).

Kits may also optionally include any of one or more of the enzymes described herein, as well as deoxynucleoside triphosphates and/or ribonucleoside triphosphates. Kits may also include one or more suitable buffers (as described herein). Kits useful for nucleic acid sequencing may optionally include labeled or unlabeled nucleotide analogs that upon incorporation into a primer extension product effect termination of nucleotide polymerization. One or more reagents in the kit can be provided as a dry powder, usually lyophilized, including excipients, which on dissolution will provide for a reagent solution having the appropriate concentrations for performing any of the methods described herein. Each component can be packaged in separate containers or some components can be combined in one container where cross-reactivity and shelf life permit.

The kits of the invention may optionally include a set of instructions, generally written instructions, although electronic storage media (e.g., magnetic diskette or optical disk) containing instructions are also acceptable, relating to the use of components of the methods of the invention for the intended nucleic acid amplification, and/or, as appropriate, for using the amplification products for purposes such as nucleic acid sequencing and detection of sequence mutation. The instructions included with the kit generally include information as to reagents (whether included or not in the kit) necessary for practicing the methods of the invention, instructions on how to use the kit, and/or appropriate reaction conditions. For example, the invention provides kits that comprise a first primer that comprises a sequence the complement of which is hybridizable by a propromoter polynucleotide, and instructions for using the primer to amplify RNA. In another example, kits can further comprise a second primer and/or a third primer, and optionally instructions for using the primers to amplify RNA. In other examples, the kits can contain further components, such as any of (a) a propromoter polynucleotide (such as a PTO); and (b) any of the enzymes described herein, such as an enzyme which cleaves RNA from an RNA/DNA hybrid (for example, RNaseH), DNA polymerase (RNA-dependent or DNA-dependent) and RNA polymerase. In another example, a kit comprises (a) a composite primer; and (b) instructions for amplifying RNA according to any of the methods described herein. In some embodiments, said kit further comprises a PTO. In other embodiments, said kit further comprises one or more of the following components: (a) a first primer; (b) a second primer; (c) an agent (generally RNase H) capable of cleaving RNA from RNA/DNA heteroduplexes; DNA-dependent DNA polymerase; and RNA-dependent DNA-polymerase. Any of these kits can further comprise instructions for using the components to amplify RNA.

The component(s) of the kit may be packaged in any convenient, appropriate packaging. The components may be packaged separately, or in one or multiple combinations. Where kits are provided for practicing amplification methods of the invention, the RNA polymerase (if included) is preferably provided separately from the components used in the steps prior to the transcription steps.

The relative amounts of the various components in the kits can be varied widely to provide for concentrations of the reagents that substantially optimize the reactions that need to occur to practice the methods disclosed herein and/or to further optimize the sensitivity of any assay.

The invention also provides systems for effecting the methods described herein. These systems comprise various combinations of the components discussed above. For example, the invention provides systems for amplifying a target RNA, comprising: (a) a first primer; (b) a second primer (which can be a random primer); (c) an RNA-dependent DNA polymerase; (d) a DNA-dependent DNA polymerase; (e) a propromoter polynucleotide; and (f) an enzyme that cleaves RNA from an RNA/DNA hybrid. The system may further comprise: (g) a third primer (which can be a random primer). The system may also further comprise a composite primer that hybridizes to a second strand cDNA. A system generally includes one or more apparatuses for performing the amplification methods of the invention. Such apparatuses include, for example, heating devices (such as heating blocks or water baths) and apparatuses which effect automation of one or more steps of the methods described herein.

The invention also provides reaction mixtures (or compositions comprising reaction mixtures) which contain various combinations of components described herein. An example of a reaction mixture is (a) a complex of a first primer extension product and a second primer extension product; (b) a polynucleotide comprising a propromoter sequence (for example, a PTO); and (c) RNA polymerase. Other reaction mixtures are described herein and are encompassed by the invention.

Methods Using the Amplification Methods and Compositions of the Invention

The methods and compositions of the invention can be used for a variety of purposes. For purposes of illustration, methods of sequencing, genotyping (nucleic acid mutation detection), preparation of an immobilized nucleic acid (which can be a nucleic acid immobilized on a microarray), and characterizing nucleic acids using the amplified nucleic acid products generated by the methods of the invention, are described. Methods of expression profiling, methods of subtractive hybridization and the preparation of probes for subtractive hybridization, and methods of preparing libraries (which can be cDNA and/or differential hybridization libraries) are also described.

Sequencing of RNA Targets Using the Methods of the Invention

The amplification methods of the invention are useful, for example, for sequencing of an RNA sequence of interest. The sequencing process is carried out as described for the amplification methods described herein.

The amplification methods of the invention are useful, for example, for sequencing of an RNA sequence of interest. The sequencing process is carried out by amplifying a target RNA containing the sequence of interest by any of the methods described herein. Addition of nucleotides during primer extension is analyzed using methods known in the art, for example, incorporation of a terminator nucleotide or sequencing by synthesis (e.g. pyrosequencing).

In embodiments wherein the end product is in the form of displaced DNA primer extension products, in addition to the nucleotides, such as natural deoxyribonucleotide triphosphates (dNTPs), that are used in the amplification methods, appropriate nucleotide triphosphate analogs, which may be labeled or unlabeled, that upon incorporation into a primer extension product effect termination of primer extension, may be added to the reaction mixture. Preferably, the dNTP analogs are added after a sufficient amount of reaction time has elapsed since the initiation of the amplification reaction such that a desired amount of second primer extension product or fragment extension product has been generated. Said amount of the time can be determined empirically by one skilled in the art.

In embodiments wherein the end product is in the form of RNA products, sequencing can be based on premature (deliberate) termination of RNA transcription. The inclusion of rNTP analogs, which may be labeled or unlabeled, that upon incorporation into an RNA transcript effects termination of rNTP polymerization in the reaction mixture, will result in production of truncated RNA products, which result from blocking of the RNA polymerase at sites of incorporation of the analogs.

Suitable analogs (dNTP and rNTP) include those commonly used in other sequencing methods and are well known in the art. Examples of dNTP analogs include dideoxyribonucleotides. Examples of rNTP analogs (such as RNA polymerase terminators) include 3'-dNTP. Sasaki et al., Biochemistry (1998) 95:3455–3460. These analogs may be labeled, for example, with fluorochromes or radioisotopes. The labels may also be labels which are suitable for mass spectroscopy. The label may also be a small molecule which is a member of a specific binding pair, and can be detected following binding of the other member of the specific binding pair, such as biotin and streptavidin, respectively, with the last member of the binding pair conjugated to an enzyme that catalyzes the generation of a detectable signal that could be detected by methods such as colorimetry, fluorometry or chemiluminescence. All of the above examples are well known in the art. These are incorporated into the primer extension product or RNA transcripts by the polymerase and serve to stop further extension along a template sequence. The resulting truncated polymerization products are labeled. The accumulated truncated products vary in length, according to the site of incorporation of each of the analogs, which represent the various sequence locations of a complementary nucleotide on the template sequence.

Analysis of the reaction products for elucidation of sequence information can be carried out using any of various methods known in the art. Such methods include gel electrophoresis and detection of the labeled bands using appropriate scanner, sequencing gel electrophoresis and detection of the radiolabeled band directly by phosphorescence such as Molecular Dynamics reader, capillary electrophoresis adapted with a detector specific for the labels used in the reaction, and the like. The label can also be a ligand for a binding protein which is used for detection of the label in combination with an enzyme conjugated to the binding protein, such as biotin-labeled chain terminator and streptavidin conjugated to an enzyme. The label is detected by the enzymatic activity of the enzyme, which generates a detectable signal. As with other sequencing methods known in the art, the sequencing reactions for the various nucleotide types (A, C, G, T or U) are carried out either in a single reaction vessel, or in separate reaction vessels (each representing one of the various nucleotide types). The choice of method to be used is dependent on practical considerations readily apparent to one skilled in the art, such as the nucleotide triphosphate analogs and/or label used. Thus, for example, when each of the analogs is differentially labeled, the sequencing reaction can be carried out in a single vessel. The considerations for choice of reagent and reaction conditions for optimal performance of sequencing analysis according to the methods of the invention are similar to those for other previously described sequencing methods. The reagent and reaction conditions should be as described above for the nucleic acid amplification methods of the invention.

Mutation Detection, Including Mutation Detection Based on Single Stranded Conformation Polymorphism Utilizing the Amplification Methods of the Invention The polynucleotide (generally, RNA and DNA) amplification products generated according to the methods of the invention are also suitable for analysis for the detection of any alteration in the target nucleic acid sequence, as compared to a reference nucleic acid sequence which is identical to the target nucleic acid sequence other than the sequence alteration. The sequence alterations may be sequence alterations present in the genomic sequence or may be sequence alterations which are not reflected in the genomic DNA sequences, for example, alterations due to post transcriptional alterations, and/or mRNA processing, including splice variants.

The RNA and DNA products of the amplification methods are suitable for single stranded conformation polymorphism (rSSCP) based mutation detection. The amplification methods of the invention can be directly linked to appropriate means for detecting single stranded conformation polymorphism, such as an electrophoretic separation method for the identification of specific mobility pattern of the single stranded RNA or DNA products for the elucidation of the presence of specific sequence feature(s), and/or the presence of any difference in a test nucleic acid as compared to a reference nucleic acid.

Methods based on gel electrophoresis or capillary electrophoresis can be used for the detection and analysis of the various single stranded conformational isomers. Alternatively, it is also likely that cleavage of the single stranded RNA product using nucleases which recognize sequence dependent secondary structures may be useful for the determination of sequence specific conformation polymorphism. Such nucleases are known in the art, such as the Cleavase assay (Third Wave). The electrophoretic methods are potentially more suitable for high throughput mutation, or genotyping, detection methods.

The determination of sequence specific electrophoretic pattern for a given nucleic acid sequence is useful for, for example, the detection of specific alleles of a test sequence. Furthermore, it is expected that an electrophoretic mobility pattern for the various alleles could be well differentiated, thus allowing the detection of two alleles in a nucleic acid sample from a single individual, as required for heterozygous genotype, or multiple alleles. Any alteration in the test nucleic acid sequence, such as base substitution, insertions or deletion, could be detected using this method. The method is expected to be useful for detection of specific single base polymorphism, SNP, and the discovery of new SNPs. Thus, the invention also provides methods for detecting a polynucleotide comprising a single nucleotide polymorphism, comprising: (a) amplifying a target polynucleotide using any of the methods described herein; and (b) analyzing the amplification products for single stranded conformation, wherein a difference in conformation as compared to a reference single stranded polynucleotide indicates a single nucleotide polymorphism in the target polynucleotide, whereby a polynucleotide comprising a single nucleotide polymorphism is detected.

Other art recognized methods of analysis for the detection of any alteration in the target nucleic acid sequence, as compared to a reference nucleic acid sequence, are suitable for use with the single stranded nucleic acid products of the amplification methods of the invention. Such methods are well-known in the art, and include various methods for the detection of specific defined sequences including methods based on allele specific primer extension, allele specific probe ligation, differential probe hybridization, and limited primer extension. See, for example, Kurn et al, U.S. Pat. No. 6,251,639 B1; U.S. Pat. Nos. 5,888,819; 6,004,744; 5,882,867; 5,854,033; 5,710,028; 6,027,889; 6,004,745; 5,763,178; 5,011,769; 5,185,243; 4,876,187; 5,882,867; 5,731,146; WO US88/02746; WO 99/55912; WO 92/15712; WO 00/09745; WO 97/32040; WO 00/56925; and U.S. Pat. No. 5,660,988. Thus, the invention also provides methods for detection of a mutation in an RNA sequence of interest comprising a single nucleotide polymorphism, comprising: (a) amplifying a target RNA using any of the methods described herein; and (b) analyzing the amplification products for presence of an alteration (mutation) as compared to a reference single stranded polynucleotide.

Method of Immobilizing Single Stranded Nucleic Acids

The single stranded polynucleotide (generally RNA and DNA) products of some of the amplification methods of the invention are suitable for immobilizing to a surface. The single stranded products are particularly suitable for preparing microarrays comprising the single stranded amplification products.

Amplification products can be immobilized and/or attached to a solid or semi-solid support or surface, which may be made, e.g., from glass, plastic (e.g., polypropylene, nylon), polyacrylamide, nitrocellulose, or other materials.

Several techniques are well-known in the art for immobilizing nucleic acids to a solid substrate such as a glass slide. One method is to incorporate modified bases or analogs that contain a moiety that is capable of attachment to a solid substrate, such as an amine group, a derivative of an amine group or another group with a positive charge, into the amplified nucleic acids. The amplified product is then contacted with a solid substrate, such as a glass slide, which is coated with an aldehyde or another reactive group which will form a covalent link with the reactive group that is on the amplified product and become covalently attached to the glass slide. Microarrays comprising the amplified products can be fabricated using a Biodot (BioDot, Inc. Irvine, Calif.) spotting apparatus and aldehyde-coated glass slides (GEL Associates, Houston, Tex.). Amplification products can be spotted onto the aldehyde-coated slides, and processed according to published procedures (Schena et al., *Proc. Natl. Acad. Sci. U.S.A.* (1996), 93: 10614–10619). Arrays can also be printed by robotics onto glass, nylon (Ramsay, G., *Nature Biotechnol.* (1998), 16:40–44), polypropylene (Matson, et al., *Anal Biochem*. (1995), 224(1):110–6), and silicone slides (Marshall, A. and Hodgson, J., *Nature Biotechnol.* (1998), 16:27–31). Other approaches to array assembly include fine micropipetting within electric fields (Marshall and Hodgson, supra), and spotting the polynucleotides directly onto positively coated plates. Methods such as those using amino propyl silicon surface chemistry are also known in the art, as disclosed at www.cmt.corning.com and cmm.stanford.edu/pbrown/.

One method for making microarrays is by making high-density polynucleotide arrays. Techniques are known for rapid deposition of polynucleotides (Blanchard et al., *Biosensors & Bioelectronics,* 11:687–690). Other methods for making microarrays, e.g., by masking (Maskos and Southern, *Nuc. Acids. Res.* (1992), 20:1679–1684), may also be used. In principle, and as noted above, any type of array, for example, dot blots on a nylon hybridization membrane, could be used. However, as will be recognized by those skilled in the art, very small arrays will frequently be preferred because hybridization volumes will be smaller.

The amplified polynucleotides may be spotted as a matrix on substrates comprising paper, glass, plastic, polypropylene, nylon, polyacrylamide, nitrocellulose, silicon, optical fiber or any other suitable solid or semi-solid (e.g., thin layer of polyacrylamide gel (Khrapko, et al., *DNA Sequence* (1991), 1:375–388) surface.

An array may be assembled as a two-dimensional matrix on a planar substrate or may have a three-dimensional configuration comprising pins, rods, fibers, tapes, threads, beads, particles, microtiter wells, capillaries, cylinders and any other arrangement suitable for hybridization and detection of target molecules. In one embodiment the substrate to which the amplification products are attached is magnetic beads or particles. In another embodiment, the solid substrate comprises an optical fiber. In yet another embodiment, the amplification products are dispersed in fluid phase within a capillary which, in turn, is immobilized with respect to a solid phase.

Characterization of Nucleic Acids

The methods of the invention are particularly amenable to quantitative analysis, as sufficient single stranded polynucleotide (generally, DNA and RNA) products are produced which accurately reflect the representation of the various mRNA in the starting material. The amplified products can be analyzed using, for example, probe hybridization techniques known in the art, such as Northern blotting, and hybridizing to probe arrays. In addition, the single stranded polynucleotide products may serve as starting material for other starting material for other analytical and/or quantification methods known in the art, such as real time PCR, quantitative TaqMan, quantitative PCR using molecular beacons, methods described in Kurn, U.S. Pat. No. 6,251,639, etc. Thus, the invention includes those further analytical and/or quantification methods as applied to any of the products of the methods herein.

In another embodiment, the amplification methods of the invention are utilized to generate multiple copies of single stranded polynucleotide (DNA or RNA) products that are labeled by the incorporation of labeled nucleotides during DNA or RNA polymerization. For example, amplification according to the methods of the invention can be carried out with suitable labeled dNTPs or rNTPs. These labeled nucleotides can be directly attached to a label, or can comprise a moiety which could be attached to a label. The label may be attached covalently or non-covalently to the amplification products. Suitable labels are known in the art, and include, for example, a ligand which is a member of a specific binding pair which can be detected/quantified using a detectable second member of the binding pair. Thus, amplification of total mRNA according to the methods of the invention in the presence of, for example, Cy3-dUTP or Cy5-dUTP results in the incorporation of these nucleotides into the amplification products.

The labeled amplified products are particularly suitable for analysis (for example, detection and/or quantification) by contacting them with, for example, microarrays (of any suitable surface, which includes glass, chips, plastic), beads, or particles, that comprise suitable probes such as cDNA and/or oligonucleotide probes. Thus, the invention provides methods to characterize (for example, detect and/or quantify) an RNA sequence of interest by generating labeled polynucleotide (generally, DNA or RNA) products using amplification methods of the invention, and analyzing the labeled products. Analysis of labeled products can be performed by, for example, hybridization of the labeled amplification products to, for example, probes immobilized at, for example, specific locations on a solid or semi-solid substrate, probes immobilized on defined particles, or probes immobilized on blots (such as a membrane), for example arrays, which have been described above. Other methods of analyzing labeled products are known in the art, such as, for example, by contacting them with a solution comprising probes, followed by extraction of complexes comprising the labeled amplification products and probes from solution. The identity of the probes provides characterization of the sequence identity of the amplified products, and thus by extrapolation the identity of the target RNA present in a sample. Hybridization of the labeled products is detectable, and the amount of specific labels that are detected is proportional to the amount of the labeled amplification products of a specific RNA sequence of interest. This measurement is useful for, for example, measuring the relative amounts of the various RNA species in a sample, which are related to the relative levels of gene expression, as described herein. The amount of labeled products (as indicated by, for example, detectable signal associated with the label) hybridized at defined locations on an array can be indicative of the detection and/or quantification of the corresponding target RNA species in the sample.

The labeled amplified products are particularly suitable for analysis (for example, detection and/or quantification and/or determining presence or absence of) by contacting them with, for example, microarrays that comprise suitable probes such as cDNA and/or oligonucleotide probes. Thus, the invention provides methods to characterize (for example, detect and/or quantify and/or determine presence or absence of) an RNA sequence of interest by generating labeled polynucleotide (generally, RNA or DNA) products using amplification methods of the invention, and analyzing the labeled products. Analysis of labeled products can be performed by, for example, hybridization of the labeled amplification products to, for example, probes immobilized at, for example, specific locations on a solid or semi-solid substrate, probes immobilized on defined particles, or probes immobilized on blots (such as a membrane), for example arrays, which have been described above. Other methods of analyzing labeled products are known in the art, such as, for example, by contacting them with a solution comprising probes, followed by extraction of complexes comprising the labeled amplification products and probes from solution. The identity of the probes provides characterization of the sequence identity of the amplified products, and thus by extrapolation the identity of the target RNA present in a sample. Hybridization of the labeled products is detectable, and the amount of specific labels that are detected is proportional to the amount of the labeled amplification products of a specific RNA sequence of interest. This measurement is useful for, for example, measuring the relative amounts of the various RNA species in a sample, which are related to the relative levels of gene expression. The amount of labeled products (as indicated by, for example, detectable signal associated with the label) hybridized at defined locations on an array can be indicative of the detection and/or quantification and/or presence or absence of the corresponding target RNA species in the sample.

Determination of Gene Expression Profile

The amplification methods of the invention are particularly suitable for use in determining the levels of expression of multiple genes in a sample since the methods described herein are capable of amplifying multiple target RNAs in the same sample. As described above, amplification products can be detected and quantified by various methods, as described herein and/or known in the art. Since RNA is a product of gene expression, the levels of the various RNA species, such as mRNAs, in a sample is indicative of the relative expression levels of the various genes (gene expression profile). Thus, determination of the amount of RNA sequences of interest present in a sample, as determined by quantifying amplification products of the sequences, provides for determination of the gene expression profile of the sample source.

Accordingly, the invention provides methods of determining gene expression profile in a sample, said method comprising: amplifying single stranded product from at least one RNA sequence of interest in the sample, using any of the methods described herein; and determining amount of amplification products of each RNA sequence of interest, wherein each said amount is indicative of amount of each RNA sequence of interest in the sample, whereby the expression profile in the sample is determined. Generally, labeled products are generated. In one embodiment, the target RNA is mRNA. It is understood that amount of amplification product may be determined using quantitative and/or qualitative methods. Determining amount of amplification product includes determining whether amplification product is present or absent. Thus, an expression profile can includes information about presence or absence of one or more RNA sequence of interest. "Absent" or "absence" of product, and "lack of detection of product" as used herein includes insignificant, or de minimus levels.

The methods of expression profiling are useful in a wide variety of molecular diagnostic, and especially in the study of gene expression in essentially any mammalian cell (including a single cell) or cell population. A cell or cell population (e.g. a tissue) may be from, for example, blood, brain, spleen, bone, heart, vascular, lung, kidney, pituitary, endocrine gland, embryonic cells, tumors, or the like. Expression profiling is also useful for comparing a control (normal) sample to a test sample, including test samples collected at different times, including before, after, and/or during development, a treatment, and the like.

Method of Preparing a Library

The single stranded polynucleotides (generally DNA and RNA) products of the methods of the invention are useful in preparing libraries, including cDNA libraries and subtractive hybridization libraries. Using the methods of the invention, libraries may be prepared from limited amount of starting material, for example, mRNA extracted from limited amount of tissue or even single cells. Accordingly, in one aspect, the methods of the invention provides preparing a library from the single stranded DNA or RNA products of the invention. In still another aspect, the invention provides methods for making a library, said method comprising: preparing a subtractive hybridization probe using any of the methods described herein.

Accordingly, in one aspect, the methods of the invention provides preparing a library from the single stranded DNA or RNA products of the invention. In some embodiments, the library is a cDNA library.

Methods of Subtractive Hybridization

The amplification methods of the invention are particularly suitable for use in subtractive hybridization methods, since the methods described herein are capable of amplifying multiple target RNAs in the same sample, and the methods of the invention are suitable for producing large amounts of single stranded anti-sense DNA and RNA product suitable for use as "driver" in subtractive hybridization. For example, two nucleic acid populations, one sense and one antisense, can be allowed to mix together with one population present in molar excess ("driver"). Sequence present in both populations will form hybrids, while sequences present in only one population remain single-stranded. Thereafter, various well known techniques are used to separate the unhybridized molecules representing differentially expressed sequences. See, e.g., Hamson et al., U.S. Pat. No. 5,589,339; Van Gelder, U.S. Pat. No. 6,291,170;

Accordingly, the invention provides methods for performing subtractive hybridization, said methods comprising: (a) preparing multiple copies (generally, DNA) of the complement of at least one RNA sequences of interest from a first RNA population using any of the amplification methods described herein; and (b) hybridizing the multiple copies to a second mRNA population, whereby a subpopulation of the second mRNA population forms a complex with a nucleotide DNA copy. The invention also provides methods for performing subtractive hybridization, said methods comprising: hybridizing multiple copies of the complement of at least one RNA sequences of interest from a first RNA population using any of the amplification methods described herein to a second mRNA population, whereby a subpopulation of the second mRNA population forms a complex with a copy. In some embodiments, "driver" single stranded anti-sense DNA product of the methods of the invention is combined with tester (sense) mRNA species. In another aspect, the invention provides methods of differential amplification in which single stranded driver (antisense) DNA sequences that hybridize with tester mRNA sequence are subjected to cleavage by an agent that cleaves RNA present in a DNA/RNA hybrid, such as RNase H. Cleavage of the mRNA results in the inability to generate single stranded DNA product from the test mRNA strands. Conversely, non-cleaved tester (i.e., tester mRNA that did not hybridize to driver DNA molecules) may serve as a substrate for subsequent amplification. Amplified differentially expressed products have many uses, including as a differential expression probe, to produce differential expression libraries Accordingly, in another aspect, the invention provides methods comprising hybridizing multiple polynucleotide (generally, DNA) copies of the complement of at least one RNA sequences of interest from a first RNA population using any of the amplification methods described herein to a second mRNA population, whereby a subpopulation of the second mRNA population forms a complex with a DNA copy; (b) cleaving RNA in the complex of step (a) with an enzyme that cleaves RNA from an RNA/DNA hybrid; and (c) amplifying an unhybridized subpopulation of the second mRNA population, whereby multiple copies of single stranded polynucleotide (generally, DNA) complementary to the unhybridized subpopulation of the second mRNA population are generated.

The following Examples are provided to illustrate, but not limit, the invention.

EXAMPLES

Example 1

Amplification of Total mRNA 0.1 μg of total mRNA is combined with primer 1 (provided at a concentration of from 0.1 to 1 μM), PTO oligonucleotide (provided at a concentration of from 0.1 to 1 μM), primer 2 (provided at a concentration of from 0.1 to 1 μM) in a total volume of about 10 μ in a buffer containing 40 mM Tris, pH 8.5, 5 mM DTT, 12 MM $MgCl_2$, 70 mM KCl, 108.8 μg/ml BSA; 1 mM of each dNTP, 2 mM each of rATP, rUTP, rCTP, 1.5 mM rGTP, and 0.5 mM rITP). The mixture is incubated at 65° C. for 2 minutes, and cooled down to 37° C. (or 42° C.). 10 μl of an enzyme mixture containing T7 RNA polymerase (40 to 80 U), MMLV reverse transcriptase (10 to 30 U), and RNase H (1 to 3 U), is added to the reaction mixture, and the mixture is further incubated for 0.5 to 3 hours.

Aliquots of the reaction mixture are analyzed by gel electrophoresis (5 to 20% PAGE, Novex) for generation of amplification products.

Primer 1 sequence:
GACGGATGCGGTCTTTTTTTN (SEQ NO:1)
"N" denotes a degenerate nucleotide (i.e., it can be A, T, C or G).
Primer 2:
Random hexamer
PTO.
ggAATTCTAATACgACTCACTATAgggAgAgCGAC GGATGCGGTCT-biotin (SEQ ID NO:2)
wherein bold letters denote the sequence complementary to the 3'-end of the second primer extension product.
Primer 3:
Primer 3 is the same as primer 1.

Example 2

Amplification of Specific mRNA

The experiment of Example 1 is performed, except that primer 2 is substituted with a primer specific for a sequence of a defined mRNA species to be amplified. For example, the amplification of a sequence of GAPDH mRNA is carried out with a primer that hybridizes to a site on the first cDNA strand (first primer extension product) generated from GAPDH mRNA.

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

What is claimed is:

1. A method of generating multiple copies of the complementary sequence of an RNA sequence of interest, said method comprising the steps of:

(a) extending a first primer hybridized to a target RNA with an RNA-dependent DNA polymerase, whereby a complex comprising a first primer extension product and the target RNA is produced;

(b) cleaving RNA in the complex of step (a) with an enzyme that cleaves RNA from an RNA/DNA hybrid;

(c) extending a second primer hybridized to the first primer extension product with a DNA-dependent DNA polymerase, whereby a complex comprising the first primer extension product and a second primer extension product is produced;

(d) denaturing the complex of step (c); and (e) hybridizing to the second primer extension product a propromoter polynucleotide comprising a propromoter and a region which hybridizes to the second primer extension product under conditions which allow transcription to occur by RNA polymerase, such that RNA transcripts are produced comprising sequences complementary to the target RNA;

whereby multiple copies of the complementary sequence of the RNA sequence of interest are generated.

2. A method of generating multiple copies of the complementary sequence of an RNA sequence of interest, said method comprising the steps of:
(a) extending a first primer hybridized to a target RNA with an RNA-dependent DNA polymerase, whereby a complex comprising a first primer extension product and the target RNA is produced;
(b) cleaving RNA in the complex of step (a) with an enzyme that cleaves RNA from an RNA/DNA hybrid;
(c) extending a second primer hybridized to the first primer extension product with a DNA-dependent DNA polymerase, whereby a complex comprising the first primer extension product and a second primer extension product is produced;
(d) denaturing the complex of step (c);
(e) hybridizing to the second primer extension product a first propromoter polynucleotide comprising a propromoter and a region which hybridizes to the second primer extension product under conditions which allow transcription to occur by RNA polymerase, such that RNA transcripts are produced comprising sequences complementary to the target RNA;
(f) extending an exponential amplification primer hybridized to said RNA transcripts with an RNA-dependent DNA polymerase, whereby a complex comprising an exponential amplification primer extension product and an RNA transcript is produced;
(g) cleaving RNA in the complex of step (f) with an enzyme that cleaves RNA from an RNA/DNA hybrid;
(h) hybridizing a second propromoter polynucleotide comprising a propromoter and a region which hybridizes to a single stranded exponential amplification primer extension product under conditions which allow transcription to occur by RNA polymerase, such that RNA transcripts are produced comprising sequences complementary to the target RNA;
(i) optionally repeating steps (f) to (h);
whereby multiple copies of the complementary sequence of the RNA sequence of interest are produced.

3. A method of generating multiple copies of the complementary sequence of an RNA sequence of interest comprising incubating a reaction mixture, said reaction mixture comprising:
(a) a single stranded second primer extension product resulting from step (d) of claim 1;
(b) a propromoter polynucleotide comprising a propromoter and a region which is hybridizable to the single stranded second primer extension product; and
an RNA polymerase;
wherein the incubation is under conditions that permit propromoter polynucleotide hybridization and RNA transcription, whereby multiple copies of the complementary sequence of the RNA sequence of interest are generated.

4. A method of generating multiple copies of the complementary sequence of an RNA sequence of interest comprising incubating a reaction mixture, said reaction mixture comprising:

(a) a single stranded second primer extension product resulting from step (d) of claim 1;
(b) an exponential amplification primer comprising a sequence hybridizable to an RNA transcript comprising a sequence complementary to the target RNA;
(c) a first propromoter polynucleotide comprising a propromoter and a region which is hybridizable to a single stranded second primer extension product;
(d) a second propromoter polynucleotide comprising a propromoter and a region which is hybridizable to a single stranded exponential amplification extension product;
(e) an enzyme that cleaves RNA from an RNA/DNA hybrid; and
(f) an RNA polymerase;
wherein the incubation is under conditions that permit primer extension, RNA cleavage, propromoter polynucleotide hybridization and RNA transcription, whereby multiple copies of the complementary sequence of the RNA sequence of interest are generated.

5. A method of generating multiple copies of the complementary sequence of an RNA sequence of interest, said method comprising incubating a reaction mixture, said reaction mixture comprising:
(a) an RNA transcript from step (e) of claim 1;
(b) an exponential amplification primer comprising a sequence hybridizable to the RNA transcript;
(c) a propromoter polynucleotide comprising a propromoter and a region which is hybridizable to a single stranded exponential amplification primer extension product;
(d) an enzyme that cleaves RNA from an RNA/DNA hybrid; and
(e) an RNA polymerase;
wherein the incubation is under conditions that permit primer extension, RNA cleavage, propromoter polynucleotide hybridization and RNA transcription, whereby multiple copies of the complementary sequence of the RNA sequence of interest are generated.

6. A method of generating multiple copies of the complementary sequence of an RNA sequence of interest, said method comprising incubating a reaction mixture, said reaction mixture comprising:
(a) a target RNA;
(b) a first primer comprising a sequence that is hybridizable to the target RNA;
(c) a second primer comprising a sequence hybridizable to an extension product of the first primer;
(d) a propromoter polynucleotide comprising a propromoter and a region which is hybridizable to a single stranded second primer extension product;
(e) an RNA-dependent DNA polymerase;
(f) a DNA-dependent DNA polymerase;
(g) an RNA polymerase; and
(h) an enzyme that cleaves RNA from an RNA/DNA hybrid;
wherein the incubation is under conditions that permit primer hybridization, primer extension, RNA cleavage, propromoter polynucleotide hybridization, and RNA transcription, whereby multiple copies of the complementary sequence of the RNA sequence of interest are generated.

7. A method of generating multiple copies of the complementary sequence of an RNA sequence of interest, said method comprising incubating a reaction mixture, said reaction mixture comprising:

(a) a target RNA;

(b) a first primer comprising a sequence that is hybridizable to the target RNA;

(c) a second primer comprising a sequence hybridizable to an extension product of the first primer;

(d) an exponential amplification primer comprising a sequence hybridizable to an RNA transcript comprising a sequence complementary to the target RNA;

(e) a first propromoter polynucleotide comprising a propromoter and a region which is hybridizable to a single stranded second primer extension product;

(f) a second propromoter polynucleotide comprising a propromoter and a region which is hybridizable to a single stranded exponential amplification primer extension product;

(g) an RNA-dependent DNA polymerase;

(h) a DNA-dependent DNA polymerase;

(i) an RNA polymerase; and (j) an enzyme that cleaves RNA from an RNA/DNA hybrid;

wherein the incubation is conditions that permit primer hybridization, primer extension, RNA cleavage, propromoter polynucleotide hybridization, and RNA transcription, whereby multiple copies of the complementary sequence of the RNA sequence of interest are generated.

8. A method of generating multiple copies of the complementary sequence of an RNA sequence of interest, said method comprising incubating a reaction mixture, said reaction mixture comprising:

(a) a target RNA;

(b) a first primer comprising a sequence that is hybridizable to the target RNA;

(c) a propromoter polynucleotide comprising a propromoter and a region which is hybridizable to a single stranded second strand cDNA, said second strand cDNA complementary to an extension product of the first primer;

(d) an RNA-dependent DNA polymerase;

(e) a DNA-dependent DNA polymerase;

(f) an RNA polymerase; and (g) an enzyme that cleaves RNA from an RNA/DNA hybrid, wherein the incubation is under conditions that permit primer hybridization, primer extension, RNA cleavage, propromoter polynucleotide hybridization, and RNA transcription, whereby multiple copies of the complementary sequence of the RNA sequence of interest are generated.

9. A method of generating multiple copies of the complementary sequence of an RNA sequence of interest, said method comprising incubating a reaction mixture, said reaction mixture comprising:

(a) a target RNA;

(b) a first primer comprising a sequence that is hybridizable to the target RNA;

(c) an exponential amplification primer comprising a sequence hybridizable to an RNA transcript comprising a sequence complementary to the target RNA;

(d) a propromoter polynucleotide comprising a propromoter and a region which is hybridizable to a single stranded second strand cDNA, said second strand cDNA complementary to an extension product of the first primer;

(e) a propromoter polynucleotide comprising a propromoter and a region which is hybridizable to a single stranded exponential amplification primer extension product;

(f) an RNA-dependent DNA polymerase;

(g) a DNA-dependent DNA polymerase;

(h) an RNA polymerase; and (i) an enzyme that cleaves RNA from an RNA/DNA hybrid, wherein the incubation is conditions that permit primer hybridization, primer extension, RNA cleavage, propromoter polynucleotide hybridization, and RNA transcription, whereby multiple copies of the complementary sequence of the RNA sequence of interest are generated.

10. A method of generating multiple copies of the complementary sequence of an RNA sequence of interest, said method comprising the steps of:

(a) synthesizing a first primer extension product by extending a first primer hybridized to a target RNA, whereby a complex comprising the first primer extension product and the target RNA is produced;

(b) synthesizing a second primer extension product by extending a second primer hybridized to the first primer extension product, whereby a complex comprising the first primer extension product and the second primer extension product is produced;

(c) denaturing the complex of step (b);

(d) hybridizing to the second primer extension product a propromoter polynucleotide comprising a propromoter and a region which hybridizes to the second primer extension product; and (e) synthesizing RNA transcripts comprising sequences complementary to the target RNA, whereby multiple copies of the complementary sequence of the RNA sequence of interest are generated.

11. A method of generating multiple copies of the complementary sequence of an RNA sequence of interest, said method comprising the steps of:

(a) synthesizing a first primer extension product by extending a first primer hybridized to a target RNA, whereby a complex comprising the first primer extension product and the target RNA is produced;

(b) synthesizing a second primer extension product by extending a second primer hybridized to the first primer extension product, whereby a complex comprising the first primer extension product and the second primer extension product is produced;

(c) denaturing the complex of step (b);

(d) hybridizing to the second primer extension product a first propromoter polynucleotide comprising a propromoter and a region which hybridizes to the second primer extension product;

(e) synthesizing RNA transcripts comprising sequences complementary to the target RNA, such that RNA transcripts are produced comprising sequences complementary to the target RNA;

(f) synthesizing a single stranded exponential amplification primer extension product by extending an exponential amplification primer hybridized to said RNA transcripts, whereby a complex comprising an exponential amplification primer extension product and an RNA transcript is produced;

(g) synthesizing RNA transcripts comprising sequences complementary to the target RNA by hybridizing a second propromoter polynucleotide comprising a propromoter and a region which hybridizes to the single stranded exponential amplification primer extension product under conditions which allow transcription to occur by RNA polymerase, such that RNA transcripts are produced comprising sequences complementary to the target RNA; and (h) optionally repeating steps (f) to (g);

whereby multiple copies of the complementary sequence of the RNA sequence of interest are produced.

12. The method of claim 2, wherein the first primer comprises a 5' portion that is not hybridizable to the target RNA.

13. The method of claim 12, wherein said 5' portion comprises a sequence the complement of which is hybridizable by the propromoter polynucleotide in step (e) or (h).

14. The method of claim 1 or 2, wherein the target RNA is mRNA.

15. The method of claim 1 or 2, wherein the first primer comprises a poly-T sequence.

16. The method of claim 2, wherein the first primer comprises a 5' portion that is not hybridizable to the target RNA, and wherein said 5' portion comprises a sequence the complement of which is hybridizable by the propromoter polynucleotide in step (e) or (h).

17. The method of claim 2, wherein the second primer and the exponential amplification primer are the same.

18. The method of claim 2, wherein the second primer and the exponential amplification primer are different.

19. The method of claim 18, wherein the second primer and the exponential amplification primer hybridize to different complementary sequences.

20. The method of claim 1 or 2, wherein at least one type of rNTP used is a labeled rNTP, whereby labeled products are generated.

21. The method of claim 1 or 2, wherein the first primer is a random primer.

22. The method of claim 1 or 2, wherein the second primer comprises DNA.

23. The method of claim 1 or 2, wherein the second primer comprises a fragment of the target RNA hybridized to the primer extension product, said fragment generated by cleaving RNA in the complex of step (b) with an enzyme that cleaves RNA from an RNA/DNA hybrid.

24. The method of claims 1 or 2, wherein said method comprises generating multiple copies of two or more different sequences of interest.

25. The method of claim 24, wherein said method comprises at least two different first primers.

26. The method of any of claims 6, 7, 8, and 9, wherein the first primer comprises a 5' sequence that is not hybridizable to the target RNA.

27. The method of claim 26, wherein the 5' sequence comprises a sequence the complement of which is hybridizable by a propromoter polynucleotide.

28. The method of any of claims 6, 7, 8, and 9, wherein the first primer comprises a poly-T sequence; and the target RNA is mRNA.

29. The method of claim 7, wherein the second primer and the exponential amplification primer are the same.

30. The method of claim 7, wherein the second primer and the exponential amplification primer are different.

31. The method of claim 30, wherein the second primer and the exponential amplification primer hybridize to different complementary sequences.

32. The method of claims 1, 2, 4, 5, 6, 7, 8 and 9, wherein the enzyme that cleaves RNA is RNase H.

33. The method of any of claims 1, 2, 6, 7, 8, and 9, wherein the RNA-dependent DNA polymerase and DNA-dependent DNA polymerase are one enzyme.

34. The method of any of claims 1, 2, 6, 7, 8, and 9, wherein the RNA-dependent DNA polymerase and enzyme that cleaves RNA from an RNA/DNA hybrid are the same enzyme.

35. The method of any of claims 1, 2, 6, 7, 8, and 9, wherein the DNA-dependent DNA polymerase and enzyme that cleaves RNA from an RNA/DNA hybrid are the same enzyme.

36. The method of any of claims 1, 2, 6, 7, 8, and 9, wherein the DNA-dependent DNA polymerase, the RNA-dependent DNA polymerase and the enzyme that cleaves RNA from an RNA/DNA hybrid are the same enzyme.

37. The method of any of claims 1, 6, and 8, wherein the propromoter polynucleotide comprises a region at the 3' end which hybridizes to the second primer extension product, whereby DNA polymerase extension of the second primer extension product produces a double stranded promoter from which transcription occurs.

38. The method of claim 37, wherein the propromoter polynucleotide is a propromoter template oligonucleotide.

39. The method of any of claims 2, 7, and 9, wherein the propromoter polynucleotide comprises a region at the 3' end which hybridizes to the exponential amplification primer extension product, whereby DNA polymerase extension of the second primer extension product produces a double stranded promoter from which transcription occurs.

40. The method of claim 39, wherein the propromoter polynucleotide is a propromoter template oligonucleotide.

41. The method of any of claims 6, 7, 8, and 9, wherein at least one type of rNTP used is a labeled rNTP, whereby labeled products are generated.

42. A method of sequencing an RNA sequence of interest, said method comprising analyzing amplification products to determine sequence, said amplification products produced by the method of any of claims 1, 6, 7, and 10 in the presence of a mixture of rNTPs and rNTP analogs such that transcription is terminated upon incorporation of an rNTP analog.

43. The method of claim 42, wherein the target RNA is mRNA.

44. A method of sequencing an RNA sequence of interest, said method comprising analyzing amplification products to determine sequence, said amplification products produced by the method of any of claims 2, 7, 9, and 11, wherein RNA transcripts generated from the second primer extension product are amplified in the presence of a mixture of rNTPs and rNTP analogs such that transcription is terminated upon incorporation of an rNTP analog.

45. The method of claim 44, wherein the target RNA is mRNA.

46. A method of detecting a mutation in a target RNA, comprising analyzing sequences of amplification products for the presence of a mutation as compared to a reference polynucleotide sequence, said amplification products produced by the method of any of claims 1, 2, 6, 7, 8, 9, and 10.

47. The method of claim 46, wherein the target RNA is mRNA.

48. A method of detecting a mutation in a target RNA by single stranded conformation polymorphism, comprising analyzing amplification products for single stranded conformation, said amplification products produced by the method of any of claims 1, 2, 6, 7, 8, 9, 10, and 11, wherein a difference in conformation as compared to a reference single stranded polynucleotide indicates a mutation in the target polynucleotide.

49. The method of claim 48, wherein the target RNA is mRNA.

50. A method of producing a nucleic acid immobilized to a substrate comprising immobilizing amplification products on a substrate, said amplification products produced by the method of any of claims 1, 2, 6, 7, 8, 9, 10, and 11.

51. The method of claim 50, wherein the target RNA is mRNA.

52. The method of claim 50, wherein the substrate is a microarray.

53. A method of characterizing an RNA sequence of interest, comprising analyzing labeled RNA products, said labeled RNA products produced by amplifying a target RNA by the method of claim 20.

54. The method of claim 53, wherein analyzing comprises contacting the labeled RNA products with at least one probe sequence.

55. The method of claim 54, wherein the at least one probe sequence is provided as a microarray.

56. The method of claim 55, wherein the microarray comprises at least one probe immobilized on a substrate fabricated from a material selected from the group consisting of paper, ceramic, glass, plastic, polypropylene, polystyrene, nylon, polyacrylamide, nitrocellulose, silicon, and optical fiber.

57. The method of claim 56, wherein the probe is immobilized on the substrate in a two-dimensional configuration or a three-dimensional configuration comprising pins, rods, fibers, tapes, threads, beads, particles, microtiter wells, capillaries, and cylinders.

58. The method of claim 53, wherein the target RNA is mRNA.

59. The method of claim 53, wherein analyzing the labeled RNA products comprises determining amount of said products, whereby the amount of the RNA sequence of interest present in a sample is quantified.

60. A method of characterizing an RNA sequence of interest, comprising analyzing labeled RNA products, said labeled RNA products produced by amplifying a target RNA by the method of claim 41.

61. The method of claim 60, wherein analyzing comprises contacting the labeled DNA products with at least one probe.

62. The method of claim 61, wherein the at least one probe is provided as a microarray.

63. The method of claim 62, wherein the microarray comprises at least one probe immobilized on a substrate fabricated from a material selected from the group consisting of paper, glass, plastic, polypropylene, nylon, polyacrylamide, nitrocellulose, silicon, and optical fiber.

64. The method of claim 63, wherein the probe is immobilized on the substrate in a two-dimensional configuration or a three-dimensional configuration comprising pins, rods, fibers, tapes, threads, beads, particles, microtiter wells, capillaries, and cylinders.

65. The method of claim 60, wherein the target RNA is mRNA.

66. The method of claim 60, wherein analyzing the labeled RNA products comprises determining amount of said products, whereby the amount of the RNA sequence of interest present in a sample is quantified.

67. A method of determining gene expression profile in a sample, said method comprising determining amounts of amplification products of each of at least two RNA sequences of interest, said amplification products amplified by the method of any of claims 1, 2, 6, 7, 8, 9, 10, and 11, wherein each said amount is indicative of amount of each RNA sequence of interest in the sample, whereby the gene expression profile in the sample is determined.

68. The method of claim 67, wherein each target RNA is mRNA.

69. A method of preparing a library, said method comprising: preparing a library from amplified single stranded DNA or RNA product, said amplified single stranded DNA or RNA product amplified by amplifying at least two RNA sequences of interest using the method of any one of claims 1, 2, 6, 7, 8, 9, 10, and 11.

70. The method of claim 69, wherein the first primer is a random primer.

71. The method of claim 69, wherein the first primer comprises a poly-T portion.

72. A method for generating multiple copies of a sequence complementary to an RNA sequence of interest comprising:
(a) hybridizing to a single stranded second primer extension product, a propromoter polynucleotide comprising a propromoter and a region which hybridizes to the second primer extension product; and
(b) synthesizing RNA transcripts comprising sequences complementary to the target RNA whereby multiple copies of the sequence complementary to the RNA sequence of interest are generated,
wherein the second primer extension product is prepared by synthesizing a first primer extension product by extending a first primer hybridized to the RNA sequence of interest, whereby a first complex comprising the first primer extension product and the RNA sequence of interest is produced, then synthesizing a second primer extension product by extending a second primer hybridized to the first primer extension product, whereby a second complex comprising the first primer extension product and the second primer extension product is produced, and denaturing the second complex.

73. A method of performing subtractive hybridization, said method comprising: hybridizing multiple DNA copies of the complement of one or more RNA sequences of interest from a first RNA population to a second mRNA population, said multiple DNA copies prepared using the method of claim 72 whereby a subpopulation of the second mRNA population forms a complex with the DNA copies.

74. A method of performing subtractive hybridization, said method comprising: (a) hybridizing multiple DNA copies of the complement of at least two RNA sequences of interest to a second mRNA population, said multiple DNA copies prepared from a first RNA population using the method of claim 72; whereby a subpopulation of the second mRNA population forms a complex with a DNA copy; (b) cleaving RNA in the complex of step (a) with an enzyme that cleaves RNA from an RNA/DNA hybrid; and (c) amplifying the unhybridized subpopulation of the second mRNA population, whereby multiple copies of single stranded DNA complementary to the unhybridized subpopulation of the second mRNA population are generated.

75. The method of claim 1, wherein the first primer comprises a 5' portion that is not hybridizable to the target RNA.

76. The method of claim 10 or 11, wherein the first primer comprises a 5' portion that is not hybridizable to the target RNA.

77. The method of claim 76, wherein said 5' portion comprises a sequence the complement of which is hybridizable to one or more of the propromoter polynucleotides of steps (d) and (g).

78. The method of claim 10 or 11, wherein the target RNA is mRNA.

79. The method of claim 72, wherein the first primer comprises a poly-dT sequence.

80. The method of claim 11, wherein the first primer comprises a 5' portion that is not hybridizable to the target RNA, and wherein said 5' portion comprises a sequence the complement of which is hybridizable to one or more of the propromoter polynucleotides of steps (d) and (g).

81. The method of claim 11, wherein the second primer and the exponential amplification primer are the same.

82. The method of claim 11, wherein the second primer and the exponential amplification primer are different.

83. The method of claim 82, wherein the second primer and the exponential amplification primer hybridize to different complementary sequences.

84. The method of claim 10 or 11, wherein the synthesizing of RNA transcripts is carried out in the presence of at least one type of labeled rNTP, whereby labeled products are generated.

85. The method of claim 10 or 11, wherein the first primer is a random primer.

86. The method of claim 10 or 11, wherein the second primer comprises DNA.

87. The method of claim 10 or 11, wherein the second primer comprises a fragment of the target RNA hybridized to the primer extension product, said fragment generated by cleaving RNA in the complex of step (a).

88. The method of claim 10 or 11, wherein said method comprises generating multiple copies of two or more different RNA sequences of interest.

89. The method of claim 88, wherein said method comprises at least two different first primers.

90. The method of claim 85, wherein the first and second propromoter polynucleotides are the same.

91. The method of claim 85, wherein the first and second propromoter polynucleotides are different.

92. The method of claim 72, wherein the first primer comprises a 5' portion that is not hybridizable to the RNA sequence of interest.

93. The method of claim 72, wherein the RNA sequence of interest is mRNA.

94. The method of claim 93, wherein the first primer comprises a poly-dT sequence.

95. The method of claim 72, wherein the synthesis of RNA transcripts is carried out in the presence of at least one type of labeled rNTP, whereby labeled products are generated.

96. The method of claim 72, wherein the first primer is a random primer.

97. The method of claim 72, wherein said method comprises generating multiple copies of two or more different RNA sequences of interest.

98. The method of claim 97, wherein said method comprises at least two different first primers.

* * * * *

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 22
<223> OTHER INFORMATION: n = A,T,C or G
<220> FEATURE:
<221> NAME/KEY: misc_feature
<222> LOCATION: 22
<223> OTHER INFORMATION: n = A,T,C or G

<400> SEQUENCE: 1
gacggatgcg gtctttttttt tn                                              22

<210> SEQ ID NO 2
<211> LENGTH: 46
<212> TYPE: DNA
<213> ORGANISM: Artificial Sequence
<220> FEATURE:
<223> OTHER INFORMATION: Primer (thymine has biotin attached)

<400> SEQUENCE: 2
ggaattctaa tacgactcac tatagggaga gcgacggatg cggtct                     46

<210> SEQ ID NO 3
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 1
<223> OTHER INFORMATION: n = A,T,C or G

<400> SEQUENCE: 3
naaaaaaaaa aaaaaaaaa                                                   19

<210> SEQ ID NO 4
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 1
<223> OTHER INFORMATION: n = A,T,C or G

<400> SEQUENCE: 4
naaaaaaaaa aaaaaaaaa a                                                 21